(12) United States Patent
Look et al.

(10) Patent No.: US 12,002,065 B2
(45) Date of Patent: Jun. 4, 2024

(54) SYSTEMS AND METHODS FOR MANAGEMENT OF THROMBOSIS

(71) Applicant: INCUVATE, LLC, Irvine, CA (US)

(72) Inventors: David M. Look, Newport Beach, CA (US); Bradley S. Culbert, Mission Viejo, CA (US)

(73) Assignee: Incuvate, LLC, Irvine, CA (US)

( * ) Notice: Subject to any disclaimer, the term of this patent is extended or adjusted under 35 U.S.C. 154(b) by 383 days.

(21) Appl. No.: 17/130,586

(22) Filed: Dec. 22, 2020

(65) Prior Publication Data

US 2021/0110419 A1    Apr. 15, 2021

Related U.S. Application Data

(63) Continuation of application No. 16/215,289, filed on Dec. 10, 2018, now Pat. No. 10,922,704, which is a
(Continued)

(51) Int. Cl.
*A61B 17/221*    (2006.01)
*A61B 17/22*    (2006.01)
(Continued)

(52) U.S. Cl.
CPC ......... *G06Q 30/0207* (2013.01); *A61B 17/22* (2013.01); *A61B 17/32037* (2013.01);
(Continued)

(58) Field of Classification Search
CPC ... A61B 17/22; A61B 17/221; A61B 17/3203; A61B 17/32037; A61B 2017/00022;
(Continued)

(56) References Cited

U.S. PATENT DOCUMENTS

| 1,114,268 A | 10/1914 | Kells |
| 1,148,093 A | 7/1915 | Kells |

(Continued)

FOREIGN PATENT DOCUMENTS

| DE | 3715418 A1 | 11/1987 |
| EP | 806213 A1 | 11/1997 |

(Continued)

OTHER PUBLICATIONS

PCT International Search Report and Written Opinion for PCT/US2015/024569, Applicant: Incuvate, LLC, Forms PCT/ISA/220, 210, and 237 dated Jun. 29, 2015 (14 pages).

(Continued)

*Primary Examiner* — Vi X Nguyen
(74) *Attorney, Agent, or Firm* — BLAIR WALKER IP SERVICES, LLC

(57) ABSTRACT

An aspiration system includes an elongate tubular member having a lumen; an aspiration catheter configured to be inserted through the lumen of the elongate tubular member, and including a tubular aspiration member having a proximal end, a distal end, and a lumen, and configured to at least partially extend out of the lumen of the elongate tubular member at the distal end of the elongate tubular member; an elongate support member coupled to the tubular aspiration member and extending between a proximal end of the aspiration catheter and the proximal end of the tubular aspiration member; and an annular sealing member coupled to the tubular aspiration member and configured to create a seal against an inner surface of the elongate tubular member, when a vacuum sufficient to cause aspiration is actively applied to the lumen of the elongate tubular member.

20 Claims, 36 Drawing Sheets

Related U.S. Application Data continuation of application No. 15/881,529, filed on Jan. 26, 2018, now Pat. No. 10,192,230, which is a continuation of application No. 15/209,989, filed on Jul. 14, 2016, now Pat. No. 9,913,936, which is a continuation of application No. 14/680,017, filed on Apr. 6, 2015, now Pat. No. 9,433,427.

(60) Provisional application No. 62/090,822, filed on Dec. 11, 2014, provisional application No. 62/069,817, filed on Oct. 28, 2014, provisional application No. 61/976,975, filed on Apr. 8, 2014.

(51) Int. Cl.
| | |
|---|---|
| *A61B 17/3203* | (2006.01) |
| *A61M 1/00* | (2006.01) |
| *G06Q 30/02* | (2023.01) |
| *G06Q 30/0207* | (2023.01) |
| *G06Q 30/0601* | (2023.01) |
| *A61B 17/00* | (2006.01) |

(52) U.S. Cl.
CPC .............. *A61M 1/90* (2021.05); *G06Q 30/02* (2013.01); *G06Q 30/0601* (2013.01); *A61B 2017/00022* (2013.01); *A61B 2017/00119* (2013.01); *A61B 2017/22001* (2013.01); *A61B 2017/22039* (2013.01); *A61B 2017/22067* (2013.01); *A61B 2017/22079* (2013.01); *A61B 2017/22094* (2013.01); *A61B 2217/005* (2013.01)

(58) Field of Classification Search
CPC .......... A61B 2017/22001; A61B 2017/22079; A61B 2017/2212; A61B 2017/2215; G06Q 30/02
See application file for complete search history.

(56) References Cited

U.S. PATENT DOCUMENTS

| | | |
|---|---|---|
| 2,804,075 A | 8/1957 | Borden |
| 3,429,313 A | 2/1969 | Romanelli |
| 3,693,613 A | 9/1972 | Kelman |
| 3,707,967 A | 1/1973 | Kitrilakis et al. |
| 3,916,892 A | 11/1975 | Latham, Jr. |
| 3,930,505 A | 1/1976 | Wallach |
| 3,955,573 A | 5/1976 | Hansen et al. |
| 4,299,221 A | 11/1981 | Phillips et al. |
| 4,465,470 A | 8/1984 | Keiman |
| 4,574,812 A | 3/1986 | Arkans |
| 4,606,347 A | 8/1986 | Fogarty et al. |
| 4,638,539 A | 1/1987 | Palmer |
| 4,690,672 A | 9/1987 | Veltrup |
| 4,832,685 A | 5/1989 | Haines |
| 4,875,897 A | 10/1989 | Lee |
| 4,898,574 A | 2/1990 | Uchiyama et al. |
| 4,998,919 A | 3/1991 | Schnepp-Pesch et al. |
| 5,057,098 A | 10/1991 | Zelman |
| 5,064,428 A | 11/1991 | Cope et al. |
| 5,066,282 A | 11/1991 | Wijay et al. |
| 5,073,164 A | 12/1991 | Hollister et al. |
| 5,073,168 A | 12/1991 | Danforth |
| 5,078,681 A | 1/1992 | Kawashima |
| 5,125,893 A | 6/1992 | Dryden |
| 5,135,482 A | 8/1992 | Neracher |
| 5,141,518 A | 8/1992 | Hess et al. |
| 5,197,951 A | 3/1993 | Mahurkar |
| 5,234,407 A | 8/1993 | Teirstein et al. |
| 5,248,297 A | 9/1993 | Takase |
| 5,259,839 A | 11/1993 | Burns |
| 5,273,047 A | 12/1993 | Tripp et al. |
| 5,273,052 A | 12/1993 | Kraus et al. |
| 5,281,203 A | 1/1994 | Ressemann |
| 5,290,247 A | 3/1994 | Crittenden |
| 5,318,518 A | 6/1994 | Plechinger et al. |
| 5,320,604 A | 6/1994 | Walker et al. |
| 5,322,504 A | 6/1994 | Doherty et al. |
| 5,324,263 A | 6/1994 | Kraus et al. |
| 5,342,293 A | 8/1994 | Zanger |
| 5,342,306 A | 8/1994 | Don Michael |
| 5,368,555 A | 11/1994 | Sussman et al. |
| 5,378,238 A | 1/1995 | Peters et al. |
| 5,380,282 A | 1/1995 | Burns |
| 5,383,890 A | 1/1995 | Miraki et al. |
| 5,385,562 A | 1/1995 | Adams et al. |
| 5,395,315 A | 3/1995 | Griep |
| 5,403,274 A | 4/1995 | Cannon |
| 5,413,561 A | 5/1995 | Fischell et al. |
| 5,419,772 A | 5/1995 | Teitz et al. |
| 5,421,826 A | 6/1995 | Crocker et al. |
| 5,423,742 A | 6/1995 | Theron |
| 5,454,788 A | 10/1995 | Walker et al. |
| 5,468,225 A | 11/1995 | Teirstein |
| 5,484,412 A | 1/1996 | Pierpont |
| 5,486,183 A | 1/1996 | Middleman et al. |
| 5,490,837 A | 2/1996 | Blaeser et al. |
| 5,496,267 A | 3/1996 | Drasler et al. |
| 5,522,818 A | 6/1996 | Keith et al. |
| 5,527,274 A | 6/1996 | Zakko |
| 5,533,968 A | 7/1996 | Muni et al. |
| 5,536,242 A | 7/1996 | Willard et al. |
| 5,538,002 A | 7/1996 | Boussignac et al. |
| 5,567,203 A | 10/1996 | Euteneuer et al. |
| 5,577,674 A | 11/1996 | Altonji et al. |
| 5,581,038 A | 12/1996 | Lampropoulos et al. |
| 5,606,968 A | 3/1997 | Mang |
| 5,624,394 A | 4/1997 | Barnitz et al. |
| 5,647,847 A | 7/1997 | Lafontaine et al. |
| 5,658,251 A | 8/1997 | Ressemann et al. |
| 5,676,654 A | 10/1997 | Ellis et al. |
| 5,702,413 A | 12/1997 | LaFontaine |
| 5,713,849 A | 2/1998 | Bosma et al. |
| 5,713,851 A | 2/1998 | Boudewijn et al. |
| 5,713,878 A | 2/1998 | Moutafis et al. |
| 5,720,724 A | 2/1998 | Ressemann et al. |
| 5,730,717 A | 3/1998 | Gelbfish |
| 5,749,852 A | 5/1998 | Schwab et al. |
| 5,762,631 A | 6/1998 | Klein |
| 5,772,674 A | 6/1998 | Nakhjavan |
| 5,785,685 A | 7/1998 | Kugler et al. |
| 5,795,322 A | 8/1998 | Boudewijn |
| 5,827,229 A | 10/1998 | Auth et al. |
| 5,827,243 A | 10/1998 | Palestrant |
| 5,833,706 A | 11/1998 | St. Germain et al. |
| 5,843,022 A | 12/1998 | Willard et al. |
| 5,843,051 A | 12/1998 | Adams et al. |
| 5,855,567 A | 1/1999 | Ressemann |
| 5,863,284 A | 1/1999 | Klein |
| 5,868,702 A | 2/1999 | Stevens et al. |
| 5,871,462 A | 2/1999 | Yoder et al. |
| 5,885,238 A | 3/1999 | Stevens et al. |
| 5,885,244 A | 3/1999 | Leone et al. |
| 5,895,399 A | 4/1999 | Barbut et al. |
| 5,910,252 A | 6/1999 | Truitt et al. |
| 5,916,192 A | 6/1999 | Nita et al. |
| 5,921,958 A | 7/1999 | Ressemann et al. |
| 5,938,645 A | 8/1999 | Gordon |
| 5,941,871 A | 8/1999 | Adams et al. |
| 5,944,686 A | 8/1999 | Patterson et al. |
| 5,957,901 A | 9/1999 | Mottola et al. |
| 5,976,107 A | 11/1999 | Mertens et al. |
| 5,989,210 A | 11/1999 | Morris et al. |
| 6,001,112 A | 12/1999 | Taylor |
| 6,019,728 A | 2/2000 | Iwata et al. |
| 6,022,336 A | 2/2000 | Zadno-Azizi et al. |
| 6,096,001 A | 8/2000 | Drasler et al. |
| 6,096,009 A | 8/2000 | Windheuser et al. |
| 6,126,635 A | 10/2000 | Simpson et al. |
| 6,129,697 A | 10/2000 | Drasler et al. |
| 6,129,698 A | 10/2000 | Beck |
| 6,146,396 A | 11/2000 | Kónya et al. |

(56) References Cited

U.S. PATENT DOCUMENTS

| | | |
|---|---|---|
| 6,159,230 A | 12/2000 | Samuels |
| 6,176,844 B1 | 1/2001 | Lee |
| 6,179,851 B1 | 1/2001 | Barbut et al. |
| 6,190,357 B1 | 2/2001 | Ferrari et al. |
| 6,196,989 B1 | 3/2001 | Padget et al. |
| 6,216,573 B1 | 4/2001 | Moutafis et al. |
| 6,224,570 B1 | 5/2001 | Le et al. |
| 6,241,703 B1 | 6/2001 | Levin et al. |
| 6,258,061 B1 | 7/2001 | Drasler et al. |
| 6,283,719 B1 | 9/2001 | Frantz et al. |
| 6,293,960 B1 | 9/2001 | Ken |
| 6,375,635 B1 | 4/2002 | Moutafis et al. |
| 6,471,683 B2 | 10/2002 | Drasler et al. |
| 6,481,439 B1 | 11/2002 | Lewis et al. |
| 6,488,672 B1 | 12/2002 | Dance et al. |
| 6,497,698 B1 | 12/2002 | Fonger et al. |
| 6,544,209 B1 | 4/2003 | Drasler et al. |
| 6,558,401 B1 | 5/2003 | Azizi |
| 6,569,148 B2 | 5/2003 | Bagaoisan et al. |
| 6,572,578 B1 | 6/2003 | Blanchard |
| 6,579,270 B2 | 6/2003 | Sussman et al. |
| 6,585,705 B1 | 7/2003 | Maginot et al. |
| 6,599,271 B1 | 7/2003 | Easley |
| 6,610,046 B1 | 8/2003 | Usami et al. |
| 6,616,679 B1 | 9/2003 | Khosravi et al. |
| 6,622,367 B1 | 9/2003 | Bolduc et al. |
| 6,635,070 B2 | 10/2003 | Leeflang et al. |
| 6,669,710 B2 | 12/2003 | Moutafis et al. |
| 6,676,637 B1 | 1/2004 | Bonnette et al. |
| 6,706,018 B2 | 3/2004 | Westlund et al. |
| 6,719,717 B1 | 4/2004 | Johnson et al. |
| 6,723,081 B1 | 4/2004 | Hektner |
| 6,755,803 B1 | 6/2004 | Le |
| 6,755,812 B2 | 6/2004 | Peterson et al. |
| 6,818,001 B2 | 11/2004 | Wulfman et al. |
| 6,899,712 B2 | 5/2005 | Moutafis et al. |
| 6,926,726 B2 | 8/2005 | Drasler et al. |
| 6,958,059 B2 | 10/2005 | Zadno-Azizi |
| 6,986,778 B2 | 1/2006 | Zadno-Azizi |
| 6,991,625 B1 | 1/2006 | Gately et al. |
| 7,008,434 B2 | 3/2006 | Kurz et al. |
| 7,044,958 B2 | 5/2006 | Douk et al. |
| 7,232,452 B2 | 6/2007 | Adams et al. |
| 7,241,273 B2 | 7/2007 | Maguire et al. |
| 7,244,243 B2 | 7/2007 | Lary |
| 7,267,660 B2 | 9/2007 | Fonger et al. |
| 7,294,124 B2 | 11/2007 | Eidenschink |
| 7,344,515 B2 | 3/2008 | Coyle |
| 7,374,560 B2 | 5/2008 | Ressemann et al. |
| 7,479,147 B2 | 1/2009 | Honeycutt et al. |
| 7,481,222 B2 | 1/2009 | Reissmann |
| 7,503,904 B2 | 3/2009 | Choi |
| 7,588,033 B2 | 9/2009 | Wondka |
| 7,591,816 B2 | 9/2009 | Wang et al. |
| 7,604,612 B2 | 10/2009 | Ressemann et al. |
| 7,621,886 B2 | 11/2009 | Burnett |
| 7,666,161 B2 | 2/2010 | Nash et al. |
| 7,678,081 B2 | 3/2010 | Whiting et al. |
| 7,699,804 B2 | 4/2010 | Barry et al. |
| 7,717,685 B2 | 5/2010 | Moutafis et al. |
| 7,717,898 B2 | 5/2010 | Gately et al. |
| 7,736,355 B2 | 6/2010 | Itou et al. |
| 7,753,868 B2 | 7/2010 | Hoffa |
| 7,753,880 B2 | 7/2010 | Malackowski |
| 7,763,012 B2 | 7/2010 | Petrick et al. |
| 7,776,005 B2 | 8/2010 | Haggstrom et al. |
| 7,798,996 B1 | 9/2010 | Haddad et al. |
| 7,798,999 B2 | 9/2010 | Bailey et al. |
| 7,806,864 B2 | 10/2010 | Haddad et al. |
| 7,833,239 B2 | 11/2010 | Nash |
| 7,846,175 B2 | 12/2010 | Bonnette et al. |
| 7,867,192 B2 | 1/2011 | Bowman et al. |
| 7,875,004 B2 | 1/2011 | Yodfat et al. |
| 7,879,022 B2 | 2/2011 | Bonnette et al. |
| 7,887,510 B2 | 2/2011 | Karpowicz et al. |
| 7,905,710 B2 | 3/2011 | Wang et al. |
| 7,909,810 B2 | 3/2011 | Noone |
| 7,914,482 B2 | 3/2011 | Urich et al. |
| 7,914,549 B2 | 3/2011 | Morsi |
| 7,918,654 B2 | 4/2011 | Adahan |
| 7,918,822 B2 | 4/2011 | Kumar et al. |
| 7,918,835 B2 | 4/2011 | Callahan et al. |
| 7,935,077 B2 | 5/2011 | Thor et al. |
| 7,951,073 B2 | 5/2011 | Freed |
| 7,951,107 B2 | 5/2011 | Staid et al. |
| 7,951,112 B2 | 5/2011 | Patzer |
| 7,959,603 B2 | 6/2011 | Wahr et al. |
| 7,981,129 B2 | 7/2011 | Nash et al. |
| 7,988,705 B2 | 8/2011 | Galdonik et al. |
| 7,998,114 B2 | 8/2011 | Lombardi |
| 8,007,490 B2 | 8/2011 | Schaeffer et al. |
| 8,012,766 B2 | 9/2011 | Graham |
| 8,021,351 B2 | 9/2011 | Boldenow et al. |
| 8,034,018 B2 | 10/2011 | Lutwyche |
| 8,043,313 B2 | 10/2011 | Krolik et al. |
| 8,062,246 B2 | 11/2011 | Moutafis et al. |
| 8,062,257 B2 | 11/2011 | Moberg et al. |
| 8,065,096 B2 | 11/2011 | Moberg et al. |
| 8,066,677 B2 | 11/2011 | Lunn et al. |
| 8,070,694 B2 | 12/2011 | Galdonik et al. |
| 8,075,546 B2 | 12/2011 | Carlisle et al. |
| 8,092,483 B2 | 1/2012 | Galdonik et al. |
| 8,114,057 B2 | 2/2012 | Gerdts et al. |
| 8,123,778 B2 | 2/2012 | Brady et al. |
| 8,140,146 B2 | 3/2012 | Kim et al. |
| 8,152,782 B2 | 4/2012 | Jang et al. |
| 8,152,951 B2 | 4/2012 | Zawacki et al. |
| 8,157,787 B2 | 4/2012 | Nash et al. |
| 8,162,877 B2 | 4/2012 | Bonnette et al. |
| 8,177,739 B2 | 5/2012 | Cartledge et al. |
| 8,182,462 B2 | 5/2012 | Istoc et al. |
| 8,187,228 B2 | 5/2012 | Bikovsky |
| 8,202,243 B2 | 6/2012 | Morgan |
| 8,209,060 B2 | 6/2012 | Ledford |
| 8,221,348 B2 | 7/2012 | Hackett et al. |
| 8,246,573 B2 | 8/2012 | Ali et al. |
| 8,246,574 B2 | 8/2012 | Jacobs et al. |
| 8,246,580 B2 | 8/2012 | Hopkins et al. |
| 8,257,298 B2 | 9/2012 | Hamboly |
| 8,257,343 B2 | 9/2012 | Chan et al. |
| 8,262,645 B2 | 9/2012 | Bagwell et al. |
| 8,267,893 B2 | 9/2012 | Moberg et al. |
| 8,287,485 B2 | 10/2012 | Kimura et al. |
| 8,291,337 B2 | 10/2012 | Gannin et al. |
| 8,292,841 B2 | 10/2012 | Gregersen |
| 8,313,478 B2 | 11/2012 | Tockman et al. |
| 8,317,739 B2 | 11/2012 | Kuebler |
| 8,317,770 B2 | 11/2012 | Miesel et al. |
| 8,317,773 B2 | 11/2012 | Appling et al. |
| 8,317,786 B2 | 11/2012 | Dahla et al. |
| 8,323,268 B2 | 12/2012 | Ring et al. |
| 8,337,175 B2 | 12/2012 | Dion et al. |
| 8,343,131 B2 | 1/2013 | Vinten-Johansen |
| 8,348,896 B2 | 1/2013 | Wagner |
| 8,353,858 B2 | 1/2013 | Kozak et al. |
| 8,353,860 B2 | 1/2013 | Boulais et al. |
| 8,357,138 B2 | 1/2013 | Pierpont et al. |
| 8,372,038 B2 | 2/2013 | Urich et al. |
| 8,398,581 B2 | 3/2013 | Panotopoulos |
| 8,398,582 B2 | 3/2013 | Gordon et al. |
| 8,414,521 B2 | 4/2013 | Baker et al. |
| 8,414,522 B2 | 4/2013 | Kamen et al. |
| 8,419,709 B2 | 4/2013 | Haddad et al. |
| 8,425,458 B2 | 4/2013 | Scopton |
| 8,430,837 B2 | 4/2013 | Jenson et al. |
| 8,430,845 B2 | 4/2013 | Wahr et al. |
| 8,430,861 B2 | 4/2013 | Schwartz et al. |
| 8,439,876 B2 | 5/2013 | Spohn et al. |
| 8,444,625 B2 | 5/2013 | Stalker et al. |
| 8,454,557 B1 | 6/2013 | Qi et al. |
| 8,465,456 B2 | 6/2013 | Stivland |
| 8,465,867 B2 | 6/2013 | Kim |
| 8,480,697 B2 | 7/2013 | Kucharczyk et al. |
| 8,483,980 B2 | 7/2013 | Moberg et al. |

(56) References Cited

U.S. PATENT DOCUMENTS

| | | |
|---|---|---|
| 8,491,523 B2 | 7/2013 | Thor et al. |
| 8,506,537 B2 | 8/2013 | Torstensen et al. |
| 8,523,801 B2 | 9/2013 | Nash et al. |
| 8,535,272 B2 | 9/2013 | Wang et al. |
| 8,545,514 B2 | 10/2013 | Ferrera |
| 8,562,555 B2 | 10/2013 | MacMahon et al. |
| 8,597,238 B2 | 12/2013 | Bonnette et al. |
| 8,608,699 B2 | 12/2013 | Blomquist |
| 8,613,618 B2 | 12/2013 | Brokx |
| 8,613,724 B2 | 12/2013 | Lanier, Jr. et al. |
| 8,617,110 B2 | 12/2013 | Moberg et al. |
| 8,617,127 B2 | 12/2013 | Woolston et al. |
| 8,623,039 B2 | 1/2014 | Seto et al. |
| 8,641,671 B2 | 2/2014 | Michaud et al. |
| 8,647,294 B2 | 2/2014 | Bonnette et al. |
| 8,652,086 B2 | 2/2014 | Gerg et al. |
| 8,657,777 B2 | 2/2014 | Kozak et al. |
| 8,657,785 B2 | 2/2014 | Torrance et al. |
| 8,657,845 B2 | 2/2014 | Lentz |
| 8,668,464 B2 | 3/2014 | Kensy et al. |
| 8,668,665 B2 | 3/2014 | Gerg et al. |
| 8,670,836 B2 | 3/2014 | Aeschlimann et al. |
| 8,672,876 B2 | 3/2014 | Jacobson et al. |
| 8,681,010 B2 | 3/2014 | Moberg et al. |
| 8,721,674 B2 | 5/2014 | Kusleika |
| 8,734,399 B2 | 5/2014 | Nelson |
| 8,740,874 B2 | 6/2014 | Ravenscroft |
| 8,758,325 B2 | 6/2014 | Webster et al. |
| 8,771,305 B2 | 7/2014 | Shriver |
| 8,783,151 B1 | 7/2014 | Janardhan et al. |
| 8,803,030 B1 | 8/2014 | Janardhan et al. |
| 8,808,270 B2 | 8/2014 | Dann et al. |
| 8,814,847 B2 | 8/2014 | Hoffman et al. |
| 8,814,892 B2 | 8/2014 | Galdonik et al. |
| 8,851,866 B2 | 10/2014 | Moutafis et al. |
| 8,852,219 B2 | 10/2014 | Wulfman et al. |
| 8,926,525 B2 | 1/2015 | Hulvershorn et al. |
| RE45,760 E | 10/2015 | Root et al. |
| RE45,776 E | 10/2015 | Root et al. |
| 10,456,555 B2 | 10/2019 | Garrison et al. |
| 2001/0051811 A1 | 12/2001 | Bonnette et al. |
| 2002/0068895 A1 | 6/2002 | Beck |
| 2002/0087076 A1 | 7/2002 | Meguro et al. |
| 2002/0133114 A1 | 9/2002 | Itoh et al. |
| 2002/0138095 A1 | 9/2002 | Mazzocchi et al. |
| 2002/0165575 A1 | 11/2002 | Saleh |
| 2002/0173819 A1 | 11/2002 | Leeflang et al. |
| 2002/0176788 A1 | 11/2002 | Moutafis et al. |
| 2003/0032918 A1 | 2/2003 | Quinn |
| 2003/0069549 A1 | 4/2003 | MacMahon et al. |
| 2003/0088209 A1 | 5/2003 | Chiu et al. |
| 2003/0144688 A1 | 7/2003 | Brady et al. |
| 2003/0212384 A1 | 11/2003 | Hayden |
| 2003/0216760 A1 | 11/2003 | Welch et al. |
| 2003/0220556 A1 | 11/2003 | Porat et al. |
| 2003/0236533 A1 | 12/2003 | Wilson et al. |
| 2004/0049225 A1 | 3/2004 | Denison |
| 2004/0087988 A1 | 5/2004 | Heitzmann et al. |
| 2004/0147871 A1 | 7/2004 | Burnett |
| 2004/0158136 A1 | 8/2004 | Gough et al. |
| 2004/0167463 A1 | 8/2004 | Zawacki |
| 2004/0193046 A1 | 9/2004 | Nash et al. |
| 2004/0199201 A1 | 10/2004 | Kellet et al. |
| 2004/0243157 A1 | 12/2004 | Connor et al. |
| 2005/0065426 A1 | 3/2005 | Porat et al. |
| 2005/0102165 A1 | 5/2005 | Oshita et al. |
| 2005/0159716 A1 | 7/2005 | Kobayashi et al. |
| 2005/0196748 A1 | 9/2005 | Ericson |
| 2005/0240146 A1 | 10/2005 | Nash et al. |
| 2005/0283150 A1 | 12/2005 | Moutafis et al. |
| 2006/0009785 A1 | 1/2006 | Maitland et al. |
| 2006/0058836 A1 | 3/2006 | Bose et al. |
| 2006/0063973 A1 | 3/2006 | Makower et al. |
| 2006/0064123 A1 | 3/2006 | Bonnette et al. |
| 2006/0142630 A1 | 6/2006 | Meretei |
| 2007/0073233 A1 | 3/2007 | Thor et al. |
| 2007/0073268 A1 | 3/2007 | Goble et al. |
| 2007/0078438 A1 | 4/2007 | Okada |
| 2007/0197956 A1 | 8/2007 | Le et al. |
| 2007/0197963 A1 | 8/2007 | Griffiths et al. |
| 2007/0225739 A1 | 9/2007 | Pintor et al. |
| 2008/0009784 A1 | 1/2008 | Leedle et al. |
| 2008/0086110 A1 | 4/2008 | Galdonik et al. |
| 2008/0097339 A1 | 4/2008 | Ranchod et al. |
| 2008/0097563 A1 | 4/2008 | Petrie et al. |
| 2008/0195139 A1 | 8/2008 | Donald et al. |
| 2008/0249501 A1 | 10/2008 | Yamasaki |
| 2008/0255596 A1 | 10/2008 | Jenson et al. |
| 2008/0294181 A1 | 11/2008 | Wensel et al. |
| 2008/0306465 A1 | 12/2008 | Bailey et al. |
| 2008/0319376 A1 | 12/2008 | Wilcox et al. |
| 2009/0054825 A1 | 2/2009 | Melsheimer et al. |
| 2009/0105690 A1 | 4/2009 | Schaeffer et al. |
| 2009/0157057 A1 | 6/2009 | Ferren et al. |
| 2009/0292212 A1 | 11/2009 | Ferren et al. |
| 2010/0010524 A1 | 1/2010 | Barrington et al. |
| 2010/0030186 A1* | 2/2010 | Stivland .............. A61M 25/09 604/528 |
| 2010/0094201 A1 | 4/2010 | Mallaby |
| 2010/0204672 A1 | 8/2010 | Lockhart et al. |
| 2010/0217276 A1 | 8/2010 | Garrison et al. |
| 2010/0274191 A1* | 10/2010 | Ting ................. A61B 17/3403 604/116 |
| 2011/0091331 A1 | 4/2011 | Moutafis et al. |
| 2011/0106019 A1 | 5/2011 | Bagwell et al. |
| 2011/0160683 A1 | 6/2011 | Pinotti Barbosa et al. |
| 2011/0263976 A1 | 10/2011 | Hassan et al. |
| 2012/0059340 A1 | 3/2012 | Larsson |
| 2012/0071907 A1 | 3/2012 | Pintor et al. |
| 2012/0123509 A1 | 5/2012 | Merrill et al. |
| 2012/0130415 A1 | 5/2012 | Tal et al. |
| 2012/0165756 A1 | 6/2012 | Root et al. |
| 2012/0259265 A1 | 10/2012 | Salehi et al. |
| 2012/0289910 A1 | 11/2012 | Shtul et al. |
| 2012/0291811 A1 | 11/2012 | Dabney et al. |
| 2013/0069783 A1 | 3/2013 | Caso et al. |
| 2013/0085381 A1 | 4/2013 | Comerota et al. |
| 2013/0116701 A1 | 5/2013 | Wang et al. |
| 2013/0190701 A1 | 7/2013 | Kirn |
| 2013/0267891 A1 | 10/2013 | Malhi et al. |
| 2013/0310845 A1 | 11/2013 | Thor et al. |
| 2014/0005699 A1 | 1/2014 | Bonnette et al. |
| 2014/0012226 A1 | 1/2014 | Hochman |
| 2014/0147246 A1 | 5/2014 | Chappel et al. |
| 2014/0155931 A1 | 6/2014 | Bose et al. |
| 2014/0276920 A1 | 9/2014 | Hendrick et al. |
| 2014/0309589 A1 | 10/2014 | Momose et al. |
| 2014/0323906 A1 | 10/2014 | Peatfield et al. |
| 2015/0094748 A1 | 4/2015 | Nash et al. |
| 2015/0283309 A1 | 10/2015 | Look et al. |
| 2017/0136212 A1 | 5/2017 | Garrison et al. |
| 2017/0281204 A1 | 10/2017 | Garrison et al. |

FOREIGN PATENT DOCUMENTS

| | | |
|---|---|---|
| EP | 726466 B1 | 4/2002 |
| EP | 1488748 A1 | 12/2004 |
| WO | WO199005493 A1 | 5/1990 |
| WO | WO1996001079 A1 | 1/1996 |
| WO | WO1996035469 A1 | 11/1996 |
| WO | WO9918850 A1 | 4/1999 |
| WO | WO2001037916 A1 | 5/2001 |
| WO | WO2004100772 A2 | 11/2004 |
| WO | WO2007002154 A2 | 1/2007 |
| WO | WO2007143633 A2 | 12/2007 |
| WO | WO2008097993 A2 | 8/2008 |
| WO | WO2015100178 A1 | 7/2015 |
| WO | WO 2015/189354 A1 | 12/2015 |

OTHER PUBLICATIONS

PCT International Search Report and Written Opinion for PCT/US2015/024773, Applicant: Incuvate, LLC, Forms PCT/ISA/220, 210, and 237 dated Jul. 8, 2015 (10 pages).

(56) References Cited

OTHER PUBLICATIONS

Meritrans, Merit Medical Systems, Inc., 400545002/B ID 120606, Date unknown (2 pages).
Merit Mentor Simulator/Tester Instructions for Use, Merit Medical Systems, Inc. 460101002 ID 062696, Date unknown (12 pages).
Extended European Search Report dated Oct. 11, 2017, in EP App. No. 15777313.6 filed Apr. 7, 2015 (12 pages).
"Comparison of Dimensions and Aspiration Rate of the Pronto V3, Pronto LP, Export XT, Export AP, Fetch, Xtract, Diver C.E. and QuickCat Catheter", Vascular Solutions, Inc., downloaded from internet Oct. 22, 2014.
Frölich, G., Meier, P., White, S., Yellon, D., Hausenloy, D., "Myocardial reperfusion injury: looking beyond primary PCI", European Heart Journal Jun. 2013, pp. 1714-1722, vol. 34, No. 23, Elsevier, Amsterdam, The Netherlands.
Gousios, A., Shear, M, "Effect of Intravenous Heparin on Human Blood Viscosity", Circulation, Dec. 1959, pp. 1063-1066, vol. 20, American Heart Association, Dallas, USA.
"Infusion Liquid Flow Sensors—Safe, Precise and Reliable", Sensirion, downloaded from internet Apr. 3, 2015.
"Makes even the most difficult intervention a Fast and Smooth Run." GuideLiner brochure. Vascular Solutions, Inc., downloaded from internet Apr. 9, 2015.
Parikh, A., Ali, F., "Novel Use of GuideLiner Catheter to Perform Aspiration Thrombectomy in a Saphenous Vein Graft" Cath Lab Digest, Oct. 2013, downloaded from internet Oct. 22, 2014.
Prasad, A., Stone, G., Holmes, D., Gersh, B., Peperfusion Injury, Microvascular Dysfunction, and Carioprotection: The "Dark Side" of Reperfusion, Circulation, Nov. 24, 2009, pp. 2105-2112, vol. 120, American Heart Association, Dallas, USA.
Rodriquez, R., Condé-Green, A., "Quantification of Negative Pressures Generated by Syringes of Different Calibers Used for Liposuction", Plastic & Reconstructive Surgery, Aug. 2012, pp. 383e-384e, vol. 130, No. 2, Lippicott Williams & Wilkins, Philadelphia, USA.
Stys, A., Stys, T., Rajpurohit, N., Khan, M. "A Novel Application of GuideLiner Catheter for Thrombectomy in Acute Myocardial Infarction: A Case Series", Journal of Invasive cardiology, Nov. 2013, pp. 620-624, vol. 25, No. 11, King of Prussia, USA.

\* cited by examiner

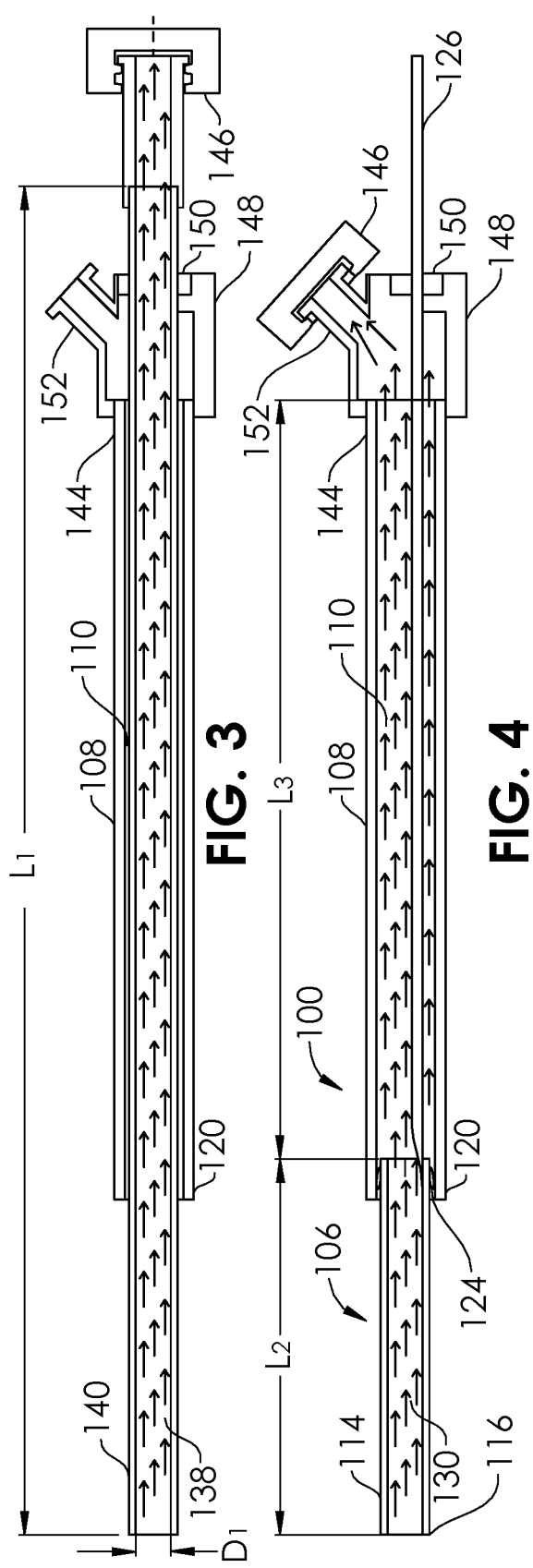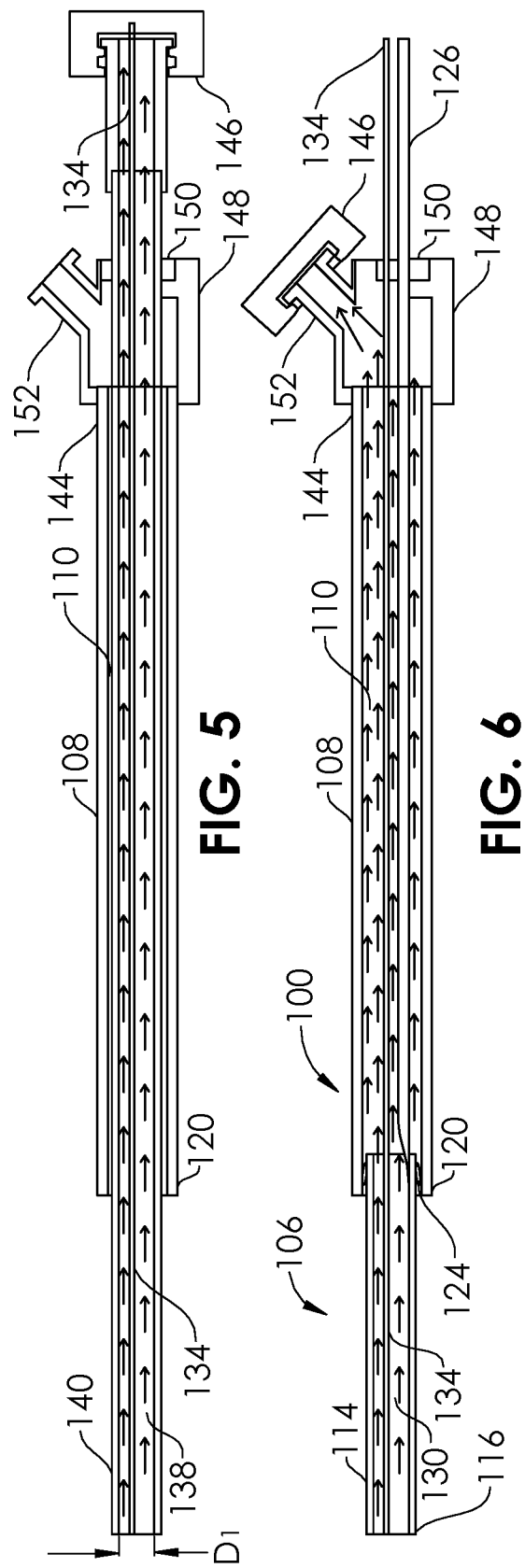

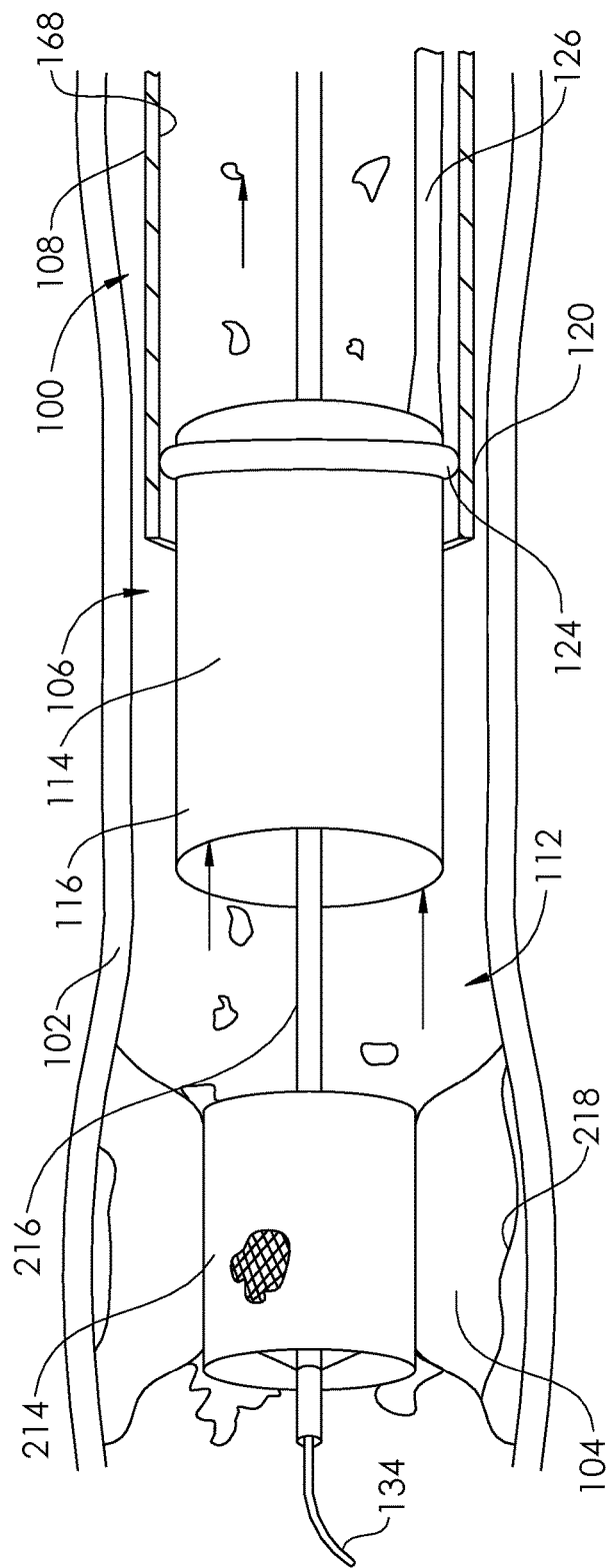
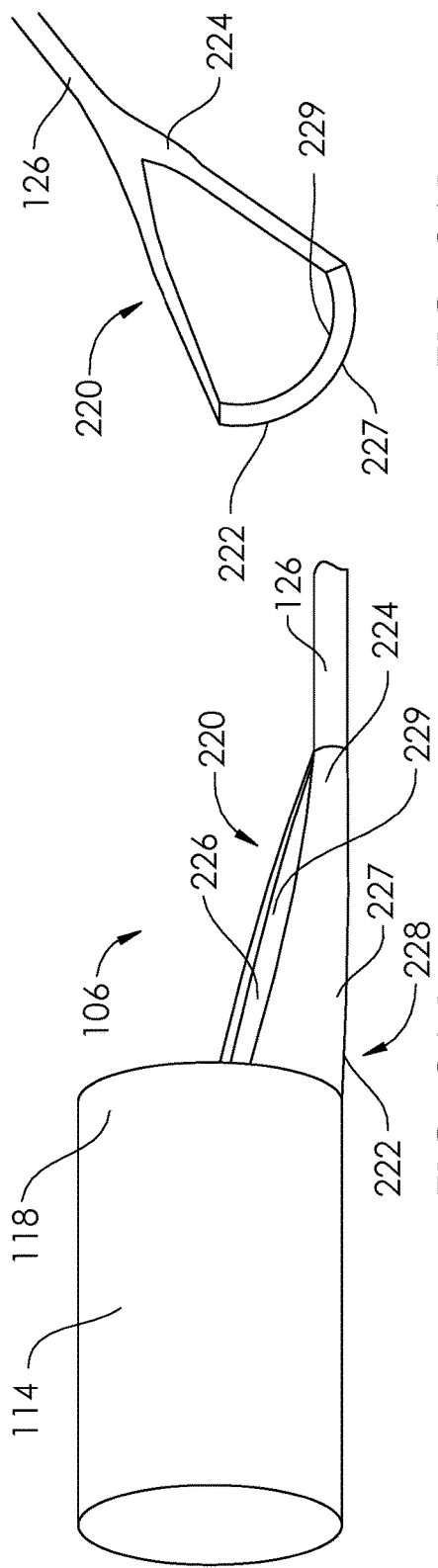
FIG. 25
FIG. 26A
FIG. 26B

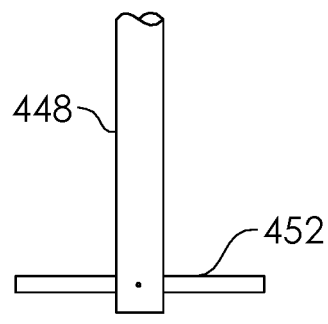
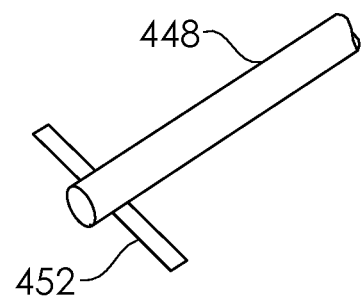
FIG. 39  FIG. 40
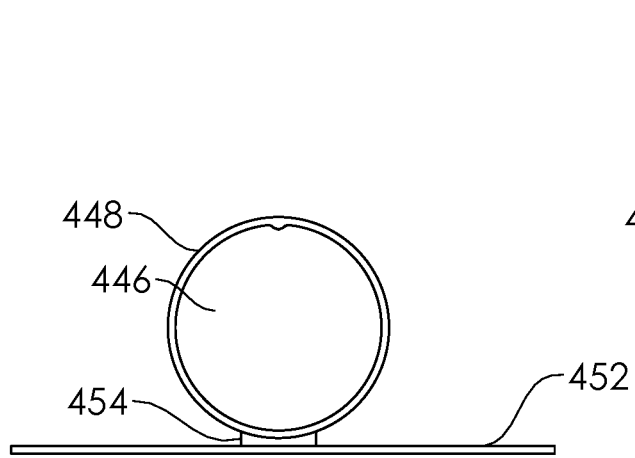
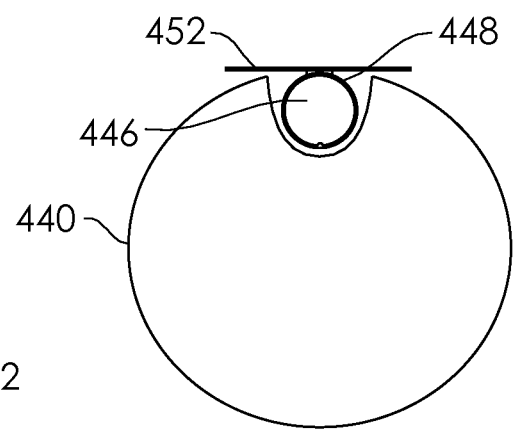
FIG. 41  FIG. 42

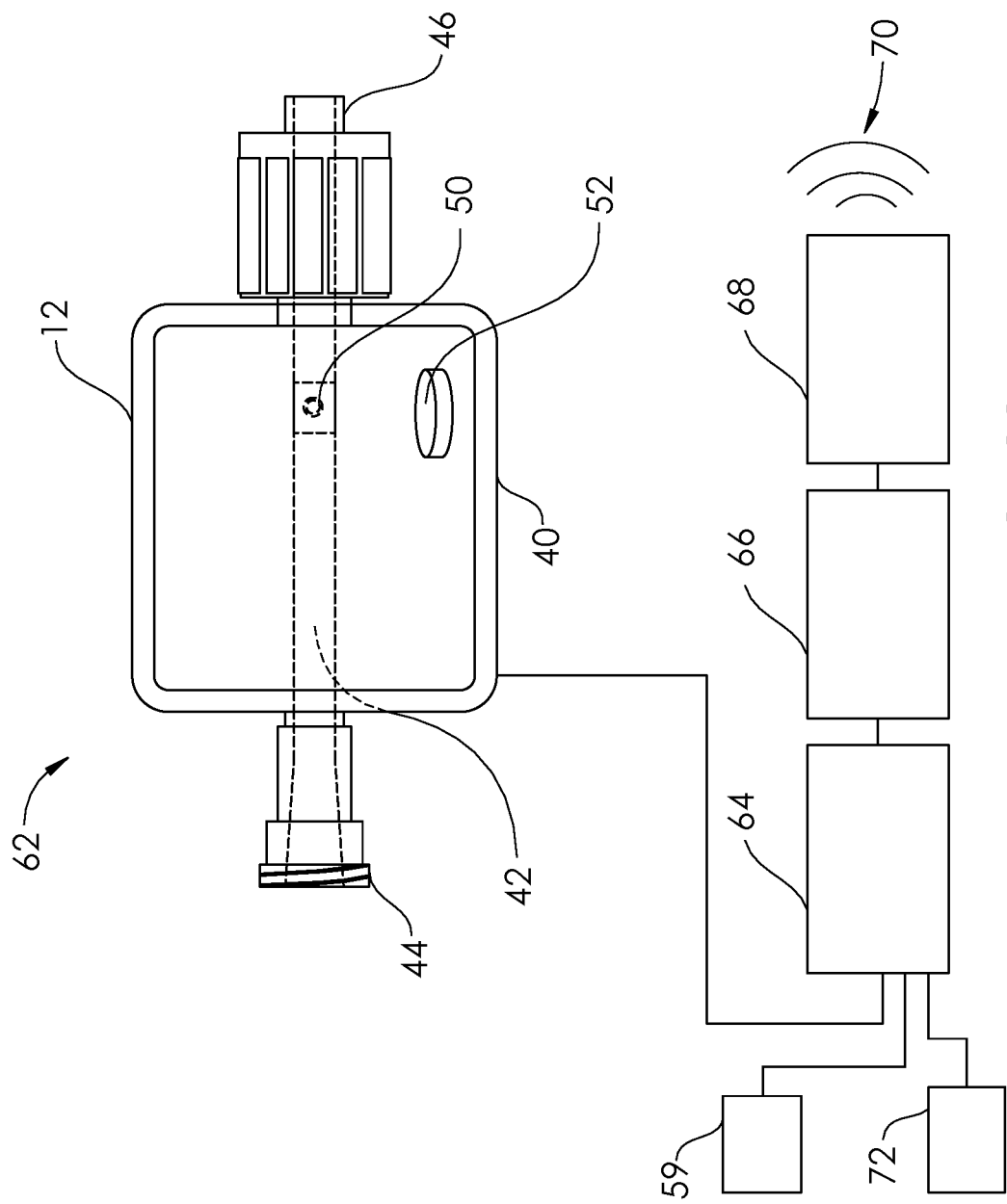

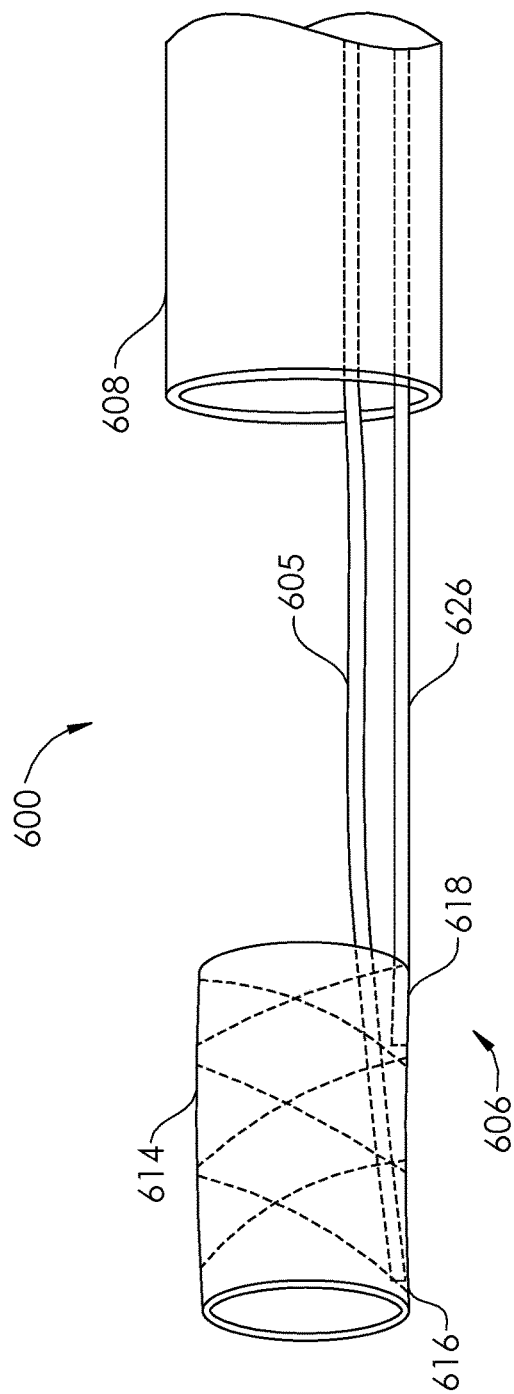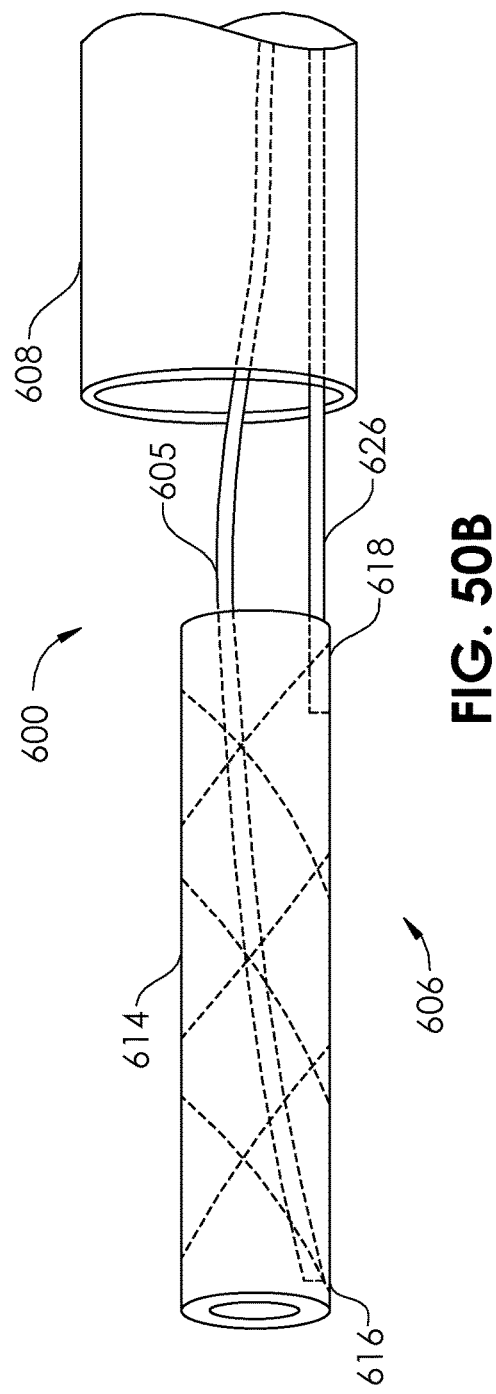

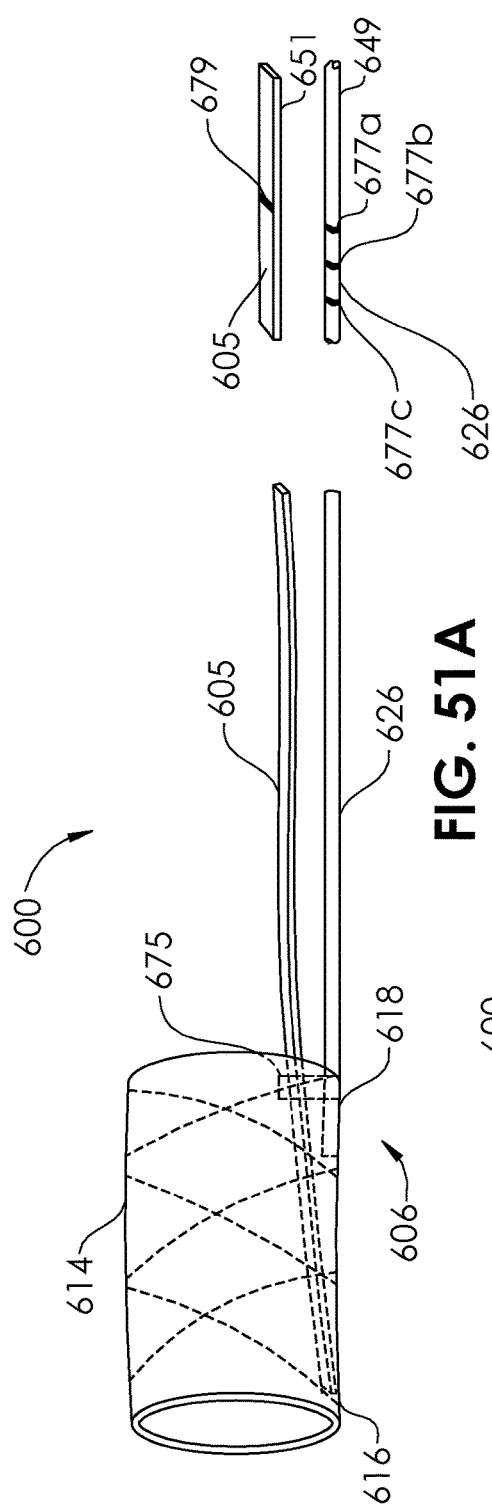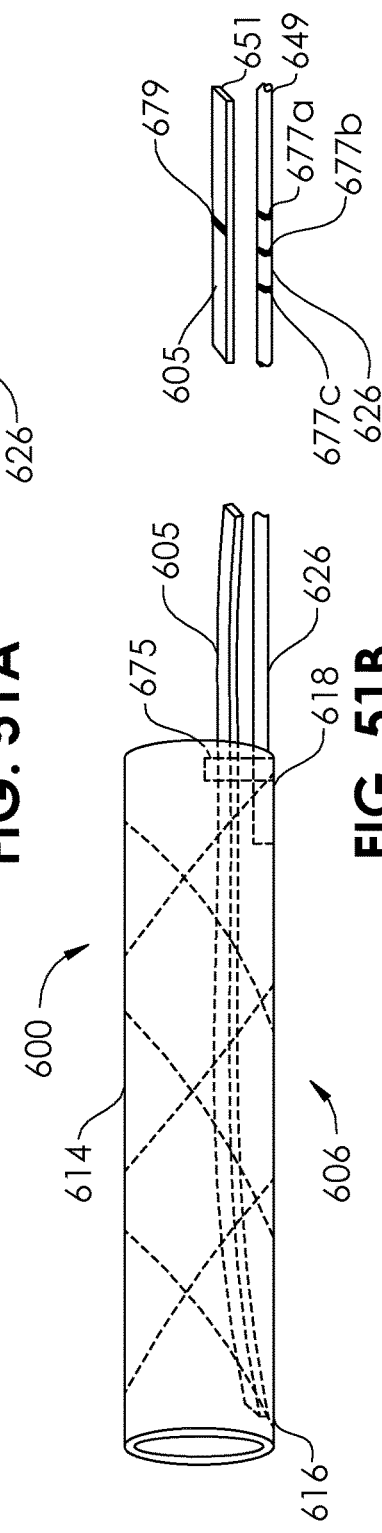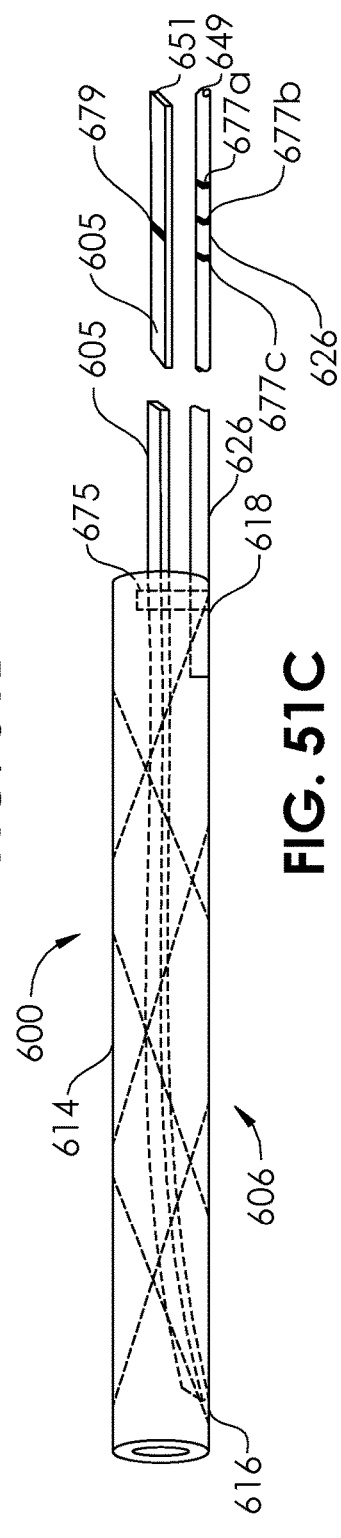

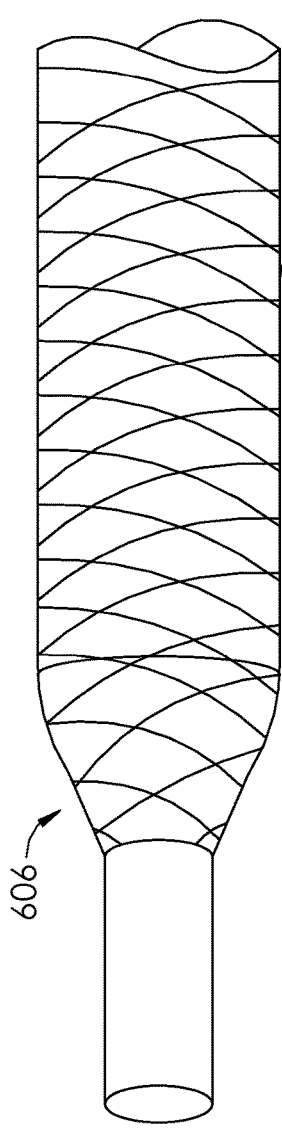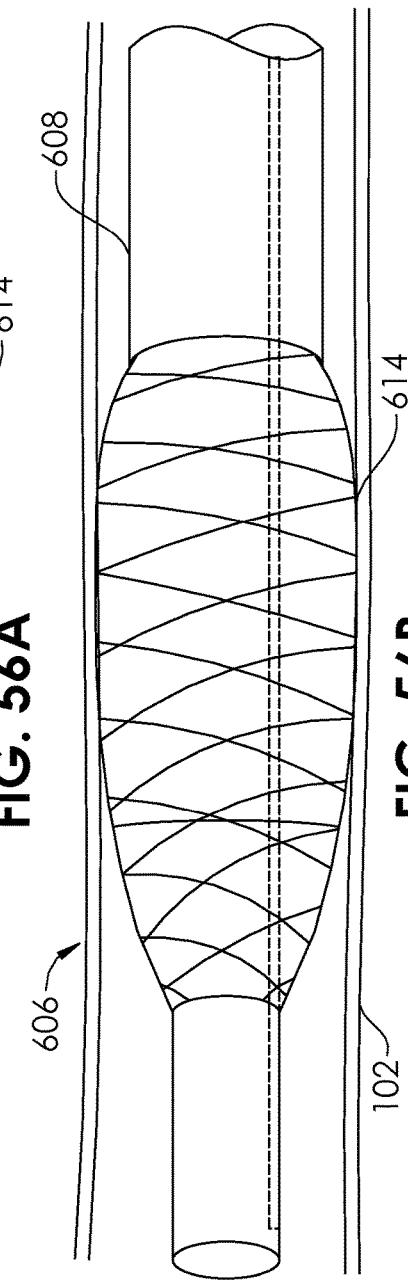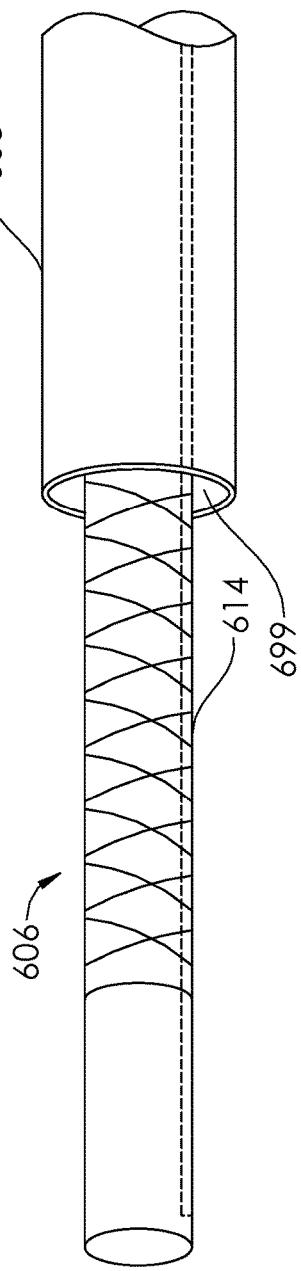

SYSTEMS AND METHODS FOR MANAGEMENT OF THROMBOSIS

INCORPORATION BY REFERENCE TO ANY PRIORITY APPLICATIONS

This application is a continuation of U.S. patent application Ser. No. 16/215,289, filed Dec. 10, 2018, now U.S. Pat. No. 10,922,704, which is a continuation of U.S. patent application Ser. No. 15/881,529, filed on Jan. 26, 2018, now U.S. Pat. No. 10,192,230, which is a continuation of U.S. patent application Ser. No. 15/209,989, filed on Jul. 14, 2016, now U.S. Pat. No. 9,913,936, which is a continuation of U.S. patent application Ser. No. 14/680,017, filed on Apr. 6, 2015, now U.S. Pat. No. 9,433,427, which claims the benefit of priority to U.S. Provisional Application No. 61/976,975, filed on Apr. 8, 2014, U.S. Provisional Application No. 62/069,817, filed on Oct. 28, 2014, and U.S. Provisional Application No. 62/090,822, filed on Dec. 11, 2014, all of which are incorporated herein by reference in their entireties for all purposes. Priority is claimed pursuant to 35 U.S.C. § 120 and 35 U.S.C. § 119.

FIELD OF THE INVENTION

The field of the invention generally relates to an aspiration system for removing, by aspiration, undesired matter such as a thrombus from a fluid carrying cavity, duct, or lumen of the body, such as a blood vessel.

BACKGROUND

Thrombosis is managed by pharmacologic means and by interventional means. These include thrombectomy, and combinations of thrombectomy with pharmacologic agents. Thrombectomy methods include breaking up and in many cases removing thrombus from a patient having thrombosis. Thrombectomy may be mechanical or non-mechanical, and may use catheter-based cutting or macerating elements, saline jets or aspiration of the thrombus.

A treatment method for removing undesired matter such as thrombus from a blood vessel of a patient involves use of an aspiration catheter having elongate shaft formed with an aspiration lumen extending therein. An aspiration catheter may also include a guidewire lumen for placement of a guidewire, which is used to guide the aspiration catheter to a target site in the body. By applying a vacuum (i.e. negative pressure) to a proximal end of the aspiration lumen, for example, with a syringe having a hub that is connected to the proximal end of the aspiration catheter, the matter can be aspirated into an aspiration port at the distal end of the aspiration catheter, into the aspiration lumen, and thus be removed from the patient.

SUMMARY OF THE INVENTION

In one embodiment, an aspiration system includes an elongate tubular member for insertion into the vasculature of a patient, the elongate tubular member having a proximal end, a distal end, a lumen extending from the proximal end to the distal end, and an inner surface defined by the lumen; an aspiration catheter having a proximal end and a distal end and configured to be inserted through the lumen of the elongate tubular member, the aspiration catheter including a tubular aspiration member having a proximal end, a distal end, and a lumen, and configured to at least partially extend out of the lumen of the elongate tubular member at the distal end of the elongate tubular member and into the vasculature of the patient; an elongate support member coupled to the tubular aspiration member and extending between the proximal end of the aspiration catheter and the proximal end of the tubular aspiration member; and an annular seal comprising at least one annular sealing member coupled to the tubular aspiration member; a vacuum source configured for coupling to the proximal end of the elongate tubular member; and wherein the at least one annular sealing member is configured to create a seal against the inner surface of the elongate tubular member, substantially preventing liquid having a viscosity of about 0.0025 Pascal-seconds from passing through an annular space between the elongate tubular member and the tubular aspiration member in a distal to proximal direction and into the lumen of the elongate tubular member proximal to the at least one annular sealing member when a vacuum sufficient to cause aspiration of the liquid through the lumen of the tubular aspiration member and the lumen of the elongate tubular member from the distal end of the tubular aspiration member to the proximal end of the elongate tubular member is actively applied to the lumen of the elongate tubular member at the proximal end of the elongate tubular member.

BRIEF DESCRIPTION OF THE DRAWINGS

FIG. 3 is a sectional view of a standard aspiration system during aspiration.

FIG. 4 is a sectional view of the embodiment of FIGS. 1 and 2 during aspiration.

FIG. 5 is a sectional view of a standard aspiration system during aspiration, with a guidewire in place through the lumens.

FIG. 6 is a sectional view of the embodiment of FIGS. 1 and 2 during aspiration, with a guidewire in place through the lumens.

FIG. 25 is a perspective view of an aspiration system according to an embodiment of the present invention in use within a blood vessel.

FIG. 26A is a perspective view of an embodiment of a catheter joint.

FIG. 26B is a perspective view of a component of the catheter joint of FIG. 26A.

FIG. 39. is a top view of a marker band during an assembly process according to an embodiment of the present invention.

FIG. 40. is a perspective view of a marker band during an assembly process according to an embodiment of the present invention.

FIG. 41. is an end view of a marker band during an assembly process according to an embodiment of the present invention.

FIG. 42. is an end view of a marker band during an assembly process using the slotted mandrel of FI. 37 according to an embodiment of the present invention.

FIG. 44B is a view of an aspiration monitoring system according to a second embodiment.

FIG. 50A is a perspective view of an aspiration system according to an embodiment of the present invention in a first configuration.

FIG. 50B is a perspective view of the aspiration system of FIG. 50A in a second configuration.

FIGS. 51A-51C are perspective views of an aspiration catheter according to an embodiment of the present invention in three different configurations.

FIGS. 56A-56C are perspective views of an aspiration system according to an embodiment of the present invention in multiple configurations.

DETAILED DESCRIPTION

Figure 1:
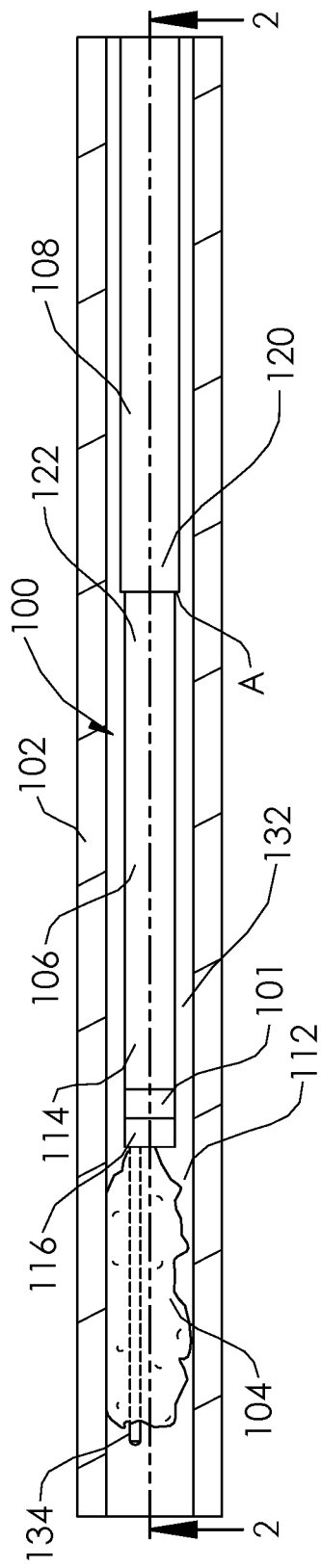
FIG. 1 is a side elevation view of an aspiration system according to an embodiment of the present invention.
Figure 2:
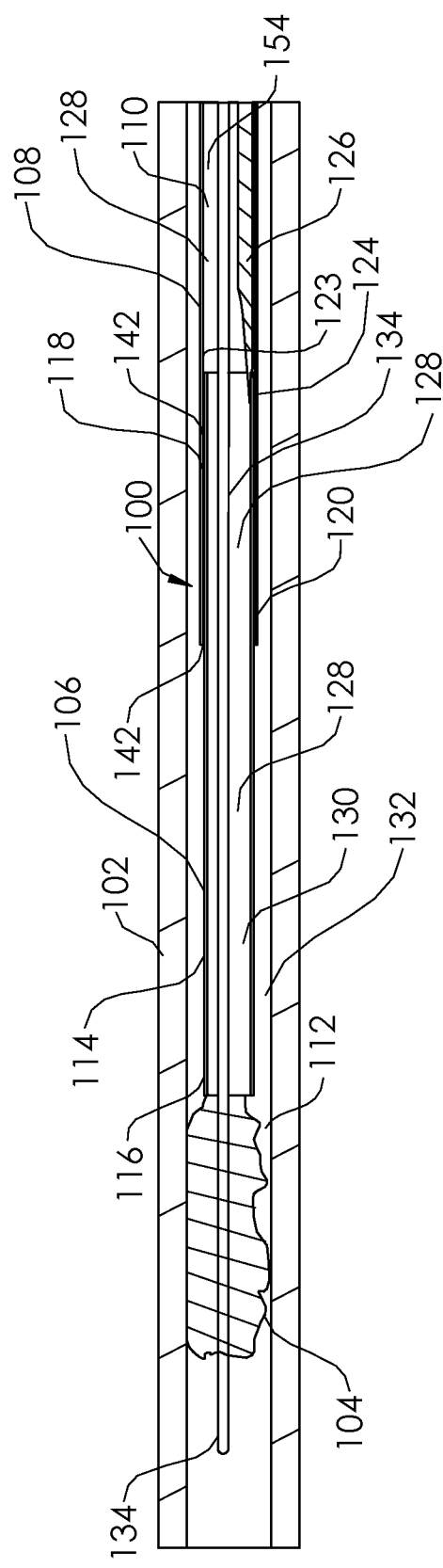
FIG. 2 is a cross-sectional view taken along line 2-2 of FIG. 1.

Referring first to FIGS. 1 and 2, the distal portion of an aspiration or thrombectomy system 100 is shown within a blood vessel 102 of a patient with thrombosis, including at least one thrombus 104. The blood vessel 102 may comprise a vein or an artery. For example, the blood vessel 102 may comprise one or more veins of the legs, including, but not limited to the femoral or iliac veins, or one or more veins of the upper extremities, including, but not limited to the subclavian, internal jugular or axillary veins. The blood vessel 102 may also comprise the inferior vena cava or superior vena cava. The blood vessel 102 may comprise an artery including, but not limited to a pulmonary artery, a coronary artery, a cerebral artery, an internal carotid artery, a femoral artery, an iliac artery, or a renal artery. The thrombectomy system 100 comprises a thrombectomy catheter 106 and a guiding catheter 108. The guiding catheter 108 may, for example, have an outer diameter of 6 French, an inner lumen diameter of approximately 0.183 cm (0.072 inches), and have a total length of approximately 100 cm. The thrombectomy catheter 106 is configured to be placed through the inner lumen 110 of the guiding catheter 108. The guiding catheter 108 may comprise a composite extruded and braided tubular structure, which has sufficient flexibility and pushability to reach a target area 112. The guiding catheter 108 may also have a pre-shaped tip. For example the tip shape may aid in cannulating coronary arteries. The thrombectomy catheter 106 comprises a distal tube 114 which is configured to be extendable out of the inner lumen 110 of the guiding catheter 108, such that a distal end 116 of the distal tube 114 can be advanced a desired length into the blood vessel 102 so that it can be placed adjacent the target area 112. The proximal end 118 of the distal tube 114 is configured to remain within the inner lumen 110 of the guiding catheter 108, for example, at a region near the distal end 120 of the guiding catheter 108. In some embodiments, the thrombectomy catheter 106 includes a radiopaque marker 101, which may comprise a band secured to the thrombectomy catheter, and made from radiodense material, such as platinum, gold, or other similar materials. In some embodiments, the distal tube 114 may be formed of polymeric materials containing radiopaque material, such as titanium dioxide ($TiO_2$).

A sealing member 124 is carried by the proximal end 118 of the distal tube 114, and may comprise, for example, an annular seal attached to an outer cylindrical surface 122 of the distal tube 114. The thrombectomy catheter 106 also comprises a support member 126, for example a wire, a hypo tube, or a composite shaft, which is secured to the distal tube 114 by adhesive, mechanical attachment or other manners described herein. The support member 126 may be relatively stiff and may have a relatively small outer diameter so that it does not block the lumen 130 of the distal tube 114. The sealing member 124 is configured to seal off an annulus 142 between the distal tube 114 and an inner surface 123 defined by the inner lumen 110 of the guiding catheter 108 so that an extended lumen 128 is created, at least when a negative pressure gradient is placed between the proximal end 144 (FIGS. 4 and 6) of the guiding catheter 108 and the distal end 116 of the distal tube 114. The negative pressure gradient may result by coupling a vacuum source 146 to the proximal end of the guiding catheter 108. For example, a y-connector 148 may be sealingly coupled to the proximal end 144 of the guiding catheter 108, and the support member 126 may extend through the y-connector 148 and be sealed by the proximal seal 150 (e.g. hemostatic valve) of the y-connector 148. The vacuum source 146 may be coupled to the side port 152 (e.g. luer) of the y-connector 148. In some embodiments, the vacuum source 146 may comprise a 20 ml syringe, 30 ml syringe, or a larger syringe, that is lockable in its evacuated condition. An example is the VacLok® syringe sold by Merit Medical Systems, Inc. of South Jordan, Utah. In some embodiments, the syringe may be attached to the side port 152 of the y-connector 148 via extension tubing known in the art. In use, when the distal end 116 of the distal tube 114 is extended out of the distal end 120 of the guiding catheter 108 into the vasculature and adjacent a thrombus 104, and the sealing member 124 is sealingly located within the inner lumen 110 of the guiding catheter 108, the negative pressure gradient caused by the application of the vacuum source 146 causes the thrombus 104, or at least a portion thereof, to be aspirated through the extended lumen 128. While being aspirated, the thrombus 104, or a portion thereof, first enters the lumen 130 of the distal tube 114 and then enters the lumen cross-section 154a, 154b of the inner lumen 110 of the guiding catheter 108, not already taken up by the support member 126 (FIG. 8), or by the support member 126 and a guidewire 134 (FIG. 10), if a guidewire is left in place within the lumens 110, 130. The seal created by the sealing member 124 assures that blood 132 (FIGS. 1 and 2) will not enter into the extended lumen 128 (the combination of lumen 130 and the lumen cross-section 154 of the inner lumen 110) through location A.

Blood has a non-Newtonian viscosity, which is known to vary depending on the shear rate the blood experiences. The mean viscosity of blood can also be varied by factors including the amount of heparinization, or anti-coagulation, employed during an interventional procedure, which may include a thrombectomy procedure. Viscosities of around 0.0025 pascal-seconds (2.5 centipoise) have been measured in heparinized blood, and as heparinization may lower normal blood viscosity, embodiments of a sealing member 124 presented herein substantially prevent a liquid having a viscosity as low as 0.0025 pascal-seconds from passing through the annular space between the guiding catheter 108 and the distal tube 114 in a distal to proximal direction and into the inner lumen 110 of the guiding catheter 108 proximal to the sealing member 124 when a sufficient vacuum pressure is applied to the inner lumen 110 of the guiding catheter 108 to cause at least some aspiration. In some embodiments, the sufficient vacuum pressure may be about −34,474 pascal (−5 pounds per square inch) or lower. In some embodiments, the sufficient vacuum pressure may be about −46,662 pascal (−6.8 pounds per square inch) or lower. In some embodiments, the sufficient vacuum pressure may range between about −82,737 pascal (−12 pounds per square inch) and about −95,526 pascal (−14 pounds per square inch). In some embodiments, the sufficient vacuum pressure may be about −89,631 pascal (−13 pounds per square inch).

Figure 11:
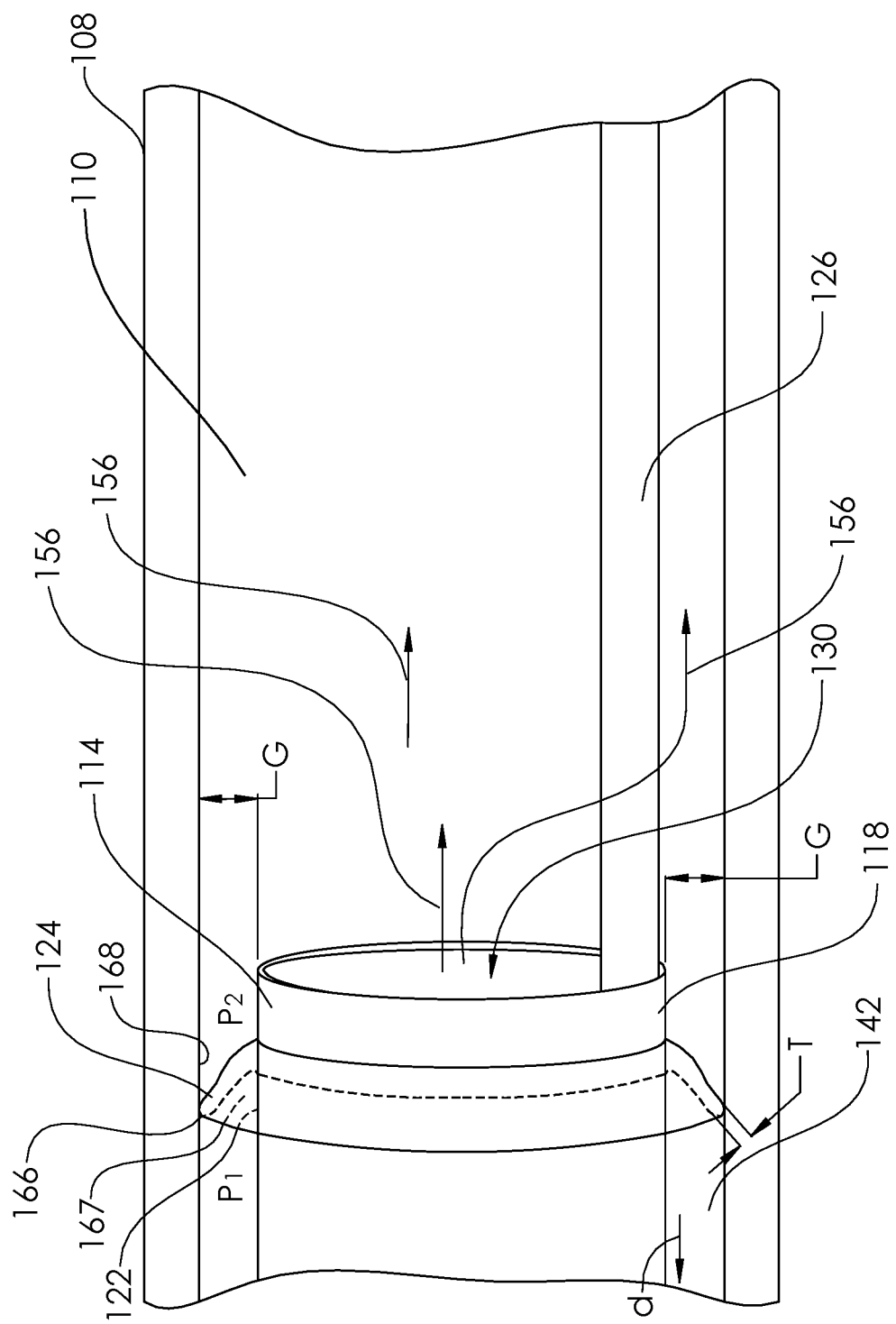
FIG. 11 is a view of an aspiration system according to an embodiment of the present invention during aspiration.
Figure 12:
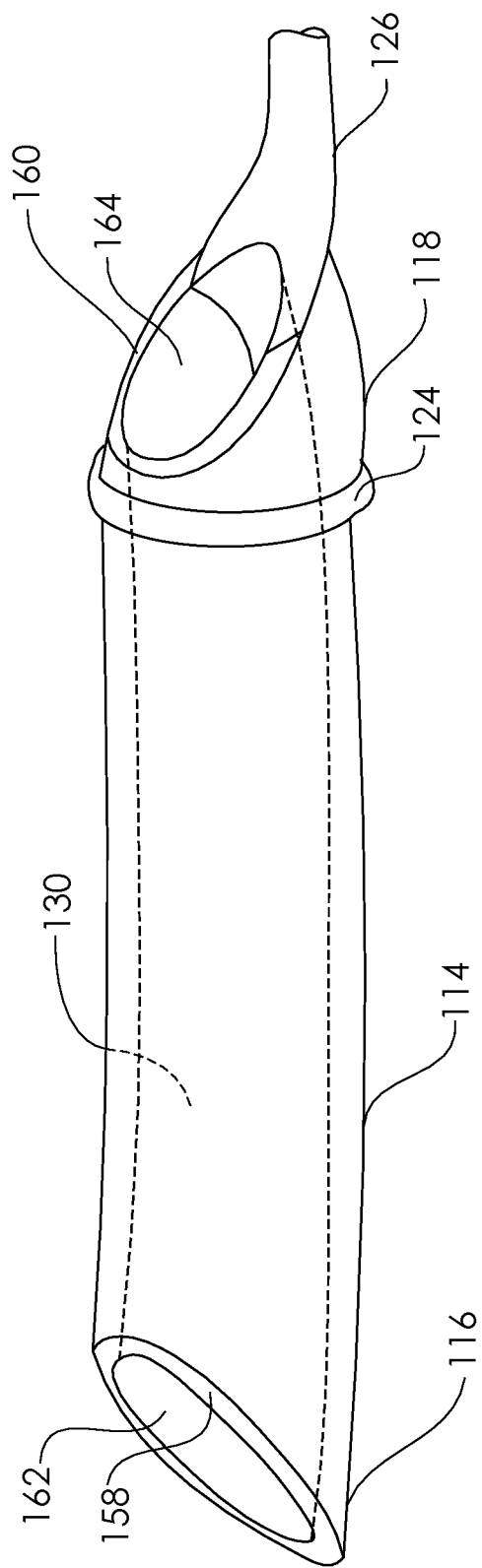
FIG. 12 is a perspective view of a distal section of an aspiration (thrombectomy) catheter according to an embodiment of the present invention.

FIG. 11 illustrates the fluid flow 156 (e.g. blood, thrombus, macerated thrombus) out of the proximal end 118 of the distal tube 114 (lumen 130) and through the inner lumen 110 of the guiding catheter 108. In the embodiment of the thrombectomy system 100 illustrated in FIGS. 1 and 2, the distal tube 114 has a lumen 130 configured for tracking over the guidewire 134. The guidewire 134 (e.g. 0.014" coronary guidewire) may be used to guide the thrombectomy catheter 106 through the blood vessel 102, with the lumen 130 of the distal tube 114 acting as a single-operator exchange lumen. In some embodiments, the length of this lumen 130 may be between 5 cm and 35 cm. In some embodiments, it may be between 10 cm and 30 cm. In some embodiments, it may be between 15 cm and 25 cm. In some embodiments, it may be about 25 cm. As illustrated in FIG. 12, the distal tube 114 may have a skive 158 at its distal end 116 and/or a skive 160 at its proximal end 118. The skives 158, 160 may serve at least two purposes. First they aid in the tracking of the distal tube 114 and thus the thrombectomy catheter 106 through the blood vessel 102, including any thrombus 104 or atherosclerotic plaque (not shown), past the distal end 120 of the guiding catheter 108, and in and out of the y-connector 148, including the proximal seal 150. Second, the skives 158, 160 increase the cross-section area at the entry (or exit) points of the lumen 130 of the distal tube 114, thus lowering resistance to flow, and allowing, for example, relatively larger pieces or portions of thrombus to enter the lumen 130. The distal tube 114 in FIG. 12 is depicted in a slightly curved state so that the openings 162, 164 at either end of the lumen 130 face the viewer, so that the skives 158, 160 may be better appreciated.

Returning to FIG. 11, the sealing member 124 is shown as an annular seal with a distally facing lip 166. An annular concavity 167 extends circumferentially around the distal tube 114 between the distally facing lip 166 and the outer cylindrical surface 122 of the distal tube 114. In some embodiments, the sealing member 124 may be made from a number of elastomeric materials including silicone, EPDM, polyurethane, or thermoplastic elastomers, such as PEBAX or Santoprene®. The thin-walled construction of the distal tube 114 allows a finite gap G between the distal tube 114 and the inner lumen 110 of the guiding catheter 108, while still maintaining a relatively large lumen 130 in the distal tube 114, in some embodiments as large as about 0.152 cm (0.060 inches) or larger (for a 6F guiding catheter compatible thrombectomy catheter 106). In some embodiments, the gap G is 0.003" or more on each side, and the thin lip 166 may have a thickness T of about 0.000635 cm (0.00025 inches) to about 0.00508 cm (0.0020 inches). In other embodiments, the thickness T may be between about 0.0019 cm (0.00075 inches) and about 0.0038 cm (0.0015 inches). On other embodiments, the thickness T may be between about 0.00254 cm (0.001 inches) and about 0.00317 cm (0.00125 inches). With a gap G on the order of 0.0076 cm (0.003 inches) or more per side, there would be a risk of some movement of thrombus or macerated thrombus through the annulus 142 in direction d, due to agitation, and perhaps into the blood vessel 102, creating a risk of embolization of a loose thrombus. However, the addition of the distally facing lip 166 allows the annulus 142 to be completely sealed whenever the vacuum source 146 (FIGS. 4 and 6) is applied, causing suction within the inner lumen 110 of the guiding catheter, and thus a pressure $P_2$ proximal to the distally facing lip 166 that is less than the pressure $P_1$ distal to the distally facing lip 166. Because the distally facing lip 166 is made from a flexible material, and/or has a relatively small thickness T, the positive pressure gradient from the $P_1$ (distal) side to the $P_2$ (proximal side) ($P_1-P_2>0$) will cause the distally facing lip 166 to be forced against the inner wall 168 of the guiding catheter 108, thus sealing it.

Figure 13:
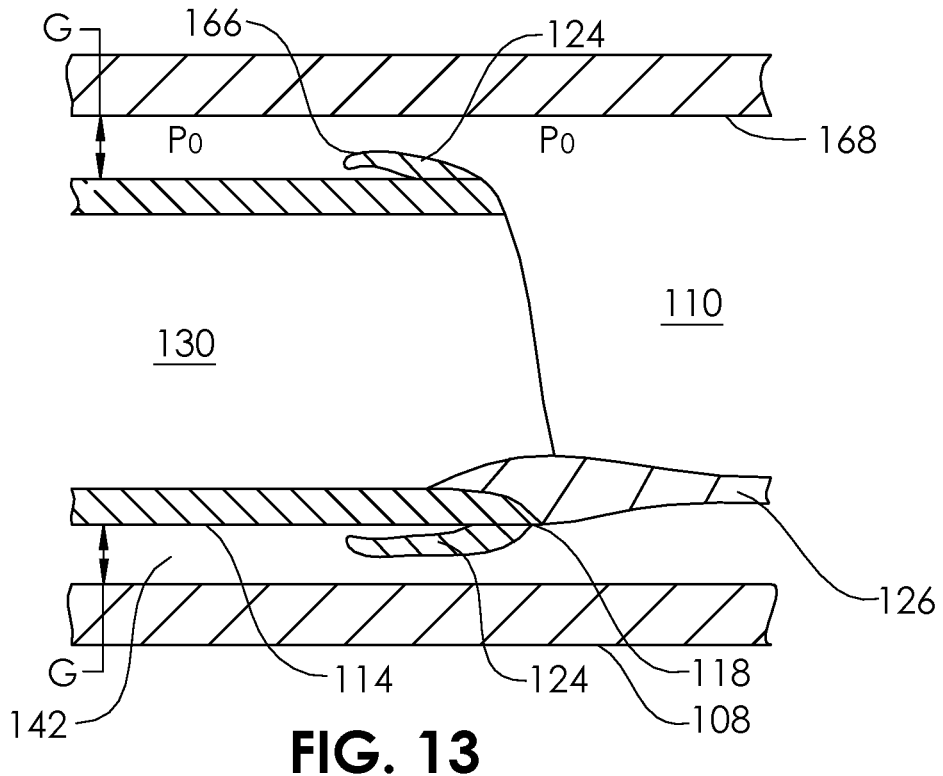
FIG. 13 is a sectional view of an aspiration system according to an embodiment of the present invention prior to aspiration.
Figure 14:
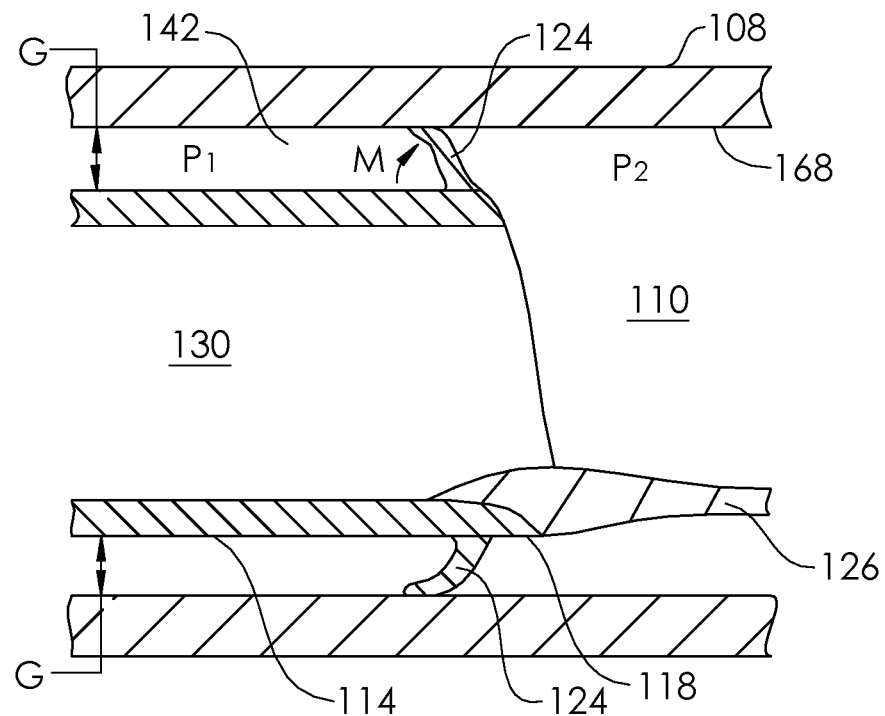
FIG. 14 is a sectional view of an aspiration system according to an embodiment of the present invention during aspiration.

The maximum outer diameter of the distally facing lip 166 may actually be smaller than the inner diameter of the inner lumen 110 of the guiding catheter 108, because it will flex (e.g., by moment M) from a first configuration (FIG. 13) to a second configuration (FIG. 14) when activated by the positive pressure gradient ($\Delta P=P_1-P_2$), in order to seal off the annulus 142. The benefit of having a distally facing lip 166 whose maximum outer diameter is smaller than the inner diameter of the inner lumen 110 of the guiding catheter 108 (when not activated by pressure), is that during tracking of the thrombectomy catheter 106, when the vacuum source 146 is not being applied, there is no seal between the distally facing lip 166 and the inner wall 168 of the guiding catheter 108, and thus there is less axial friction, thus making it easier to track and slide the thrombectomy catheter freely (longitudinal translation), providing both low axial resistance to motion (less drag), and high precision of motion (better "feel"). Thus, the distally facing lip 166 only expands when it is needed (i.e. during aspiration). In some embodiments, the distal facing lip 166 may be made using a dipping process. In some embodiments, the dipping process may be a polyurethane dipping process. In some embodiments the distally facing lip 166 may be made from non-elastomeric materials, such polyolefins, nylon, as the pressure-activated sealing does not require elastomeric compression. In some embodiments, the distally facing lip 166 may be bonded to the distal tube 114 with adhesive, epoxy, or by thermal bonding methods. In some embodiments, the seal should be liquid tight, or water tight (saline tight), and in some embodiments need not be air tight (gas tight). In some cases liquid tight may be defined as not allowing any substantial amount of blood to pass through the annulus 142. The sealing may be aided by blood viscosity, the length of the annulus 142 (distal to the sealing member 124), and the dimension of the gap G (FIG. 11). For example, a higher blood viscosity, longer annulus 142 length, and a smaller gap G dimension each serve alone or in combination to increase the sealing capacity (decrease the possibility of fluid passage through the annulus 142).

In some embodiments, the distal facing lip 166 is configured to maintain a seal when a positive pressure gradient ($\Delta P=P_1-P_2$) of about 46,662 pascal (350 mm Hg) or higher is maintained. In some embodiments, the aspiration pressure may be maintained using a vacuum pump as the vacuum source 146. In some embodiments, the vacuum pump provides a relatively constant pressure gradient of about 46,662 pascal (350 mm Hg) to about 53,328 pascal (400 mm Hg). In some embodiments, a 20 ml to 60 ml syringe is evacuated in order to serve as the vacuum source 146. In some embodiments, a 30 ml syringe is evacuated in order to serve as the vacuum source 146. In some embodiments, the evacuated 30 ml syringe provides a plateau pressure gradient of about 75,993 pascal (570 mm Hg) to about 89,626 pascal (670 mm Hg). As described, heparinized blood tends to have a viscosity of about 0.0025 pascal-seconds (2.5 cP) or higher. In some embodiments, the distally facing lip 166 is configured to seal against the inner wall 168 of the guiding catheter 108 so that a 0.0025 pascal-seconds liquid will not significantly pass distal to proximal when a distal to proximal positive pressure gradient ($\Delta P=P_1-P_2$) of 46,662 pascal (350 mm Hg) is applied. In some embodiments, the distally facing lip 166 is configured to not seal against the inner wall 168 of the guiding catheter and thus not stop the passage of a liquid from proximal to distal (i.e. through the annulus 142) when a proximal to distal positive pressure gradient ($\Delta P=P_2-P_1$) of 46,662 pascal (350 mm Hg) is applied.

Figure 7:
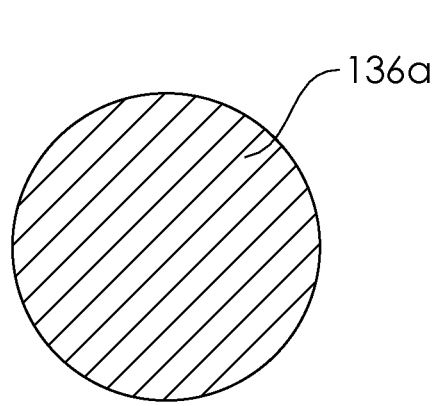
FIG. 7 is a view of the lumen cross-section in a standard aspiration catheter or in the distal tube of the embodiment of FIGS. 1 and 2.
Figure 8:
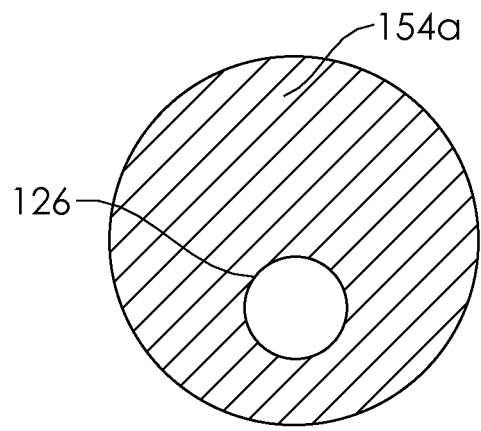
FIG. 8 is a view of the lumen cross section in a portion of a guiding catheter of the embodiment of FIGS. 1 and 2.
Figure 9:
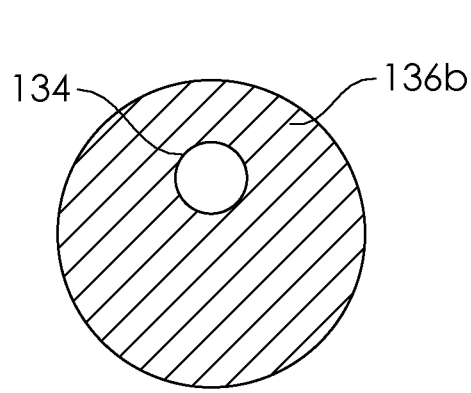
FIG. 9 is a view of the lumen cross-section in a standard aspiration catheter or in the distal tube of the embodiment of FIGS. 1 and 2, with a guidewire in place through the lumen.
Figure 10:
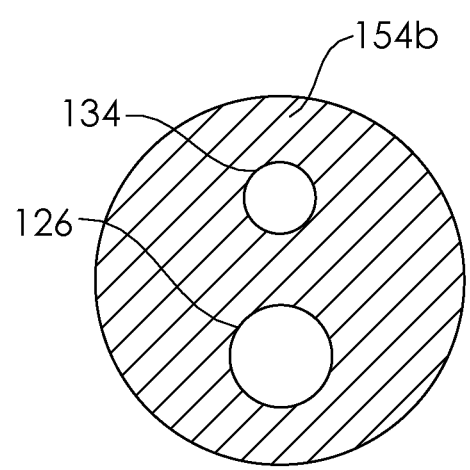
FIG. 10 is a view of the lumen cross section in a portion of a guiding catheter of the embodiment of FIGS. 1 and 2, with a guidewire in place through the lumen.

FIG. 6 illustrates the aspiration flow path and FIGS. 9 and 10 illustrate the lumen cross-sections 136b, 154b if the guidewire 134 is left in place during aspiration. FIG. 4 illustrates the aspiration flow path and FIGS. 7 and 8 illustrate the lumen cross-sections 136a, 154a if the guidewire 134 is not left in place during aspiration, for example, if it is removed. Starting with this latter "no guidewire" condition, FIG. 7 illustrates a lumen cross-section 136a, which may represented by a lumen 138 of a standard thrombectomy catheter 140 in FIG. 3, or by the lumen 130 of the thrombectomy catheter 106 of an embodiment of the present invention in FIG. 4. A comparison between the flow characteristics of the standard thrombectomy catheter 140 and the embodiment of the thrombectomy system 100 of FIGS. 1 and 2 is presented below.

The standard Hagen-Poiseuille Law flow equation used to calculate the flow of fluids (e.g. blood and/or macerated thrombus) is:

$$Q = \frac{\Delta P \pi D^4}{128 \mu L}$$

where L is the length of a particular flow path,
ΔP is the pressure gradient between one end of the flow path and the other end of the flow path,
D is the diameter of the flow path, and
μ is the viscosity of the fluid.

Because luminal cross-sectional areas are often non-circular, the term Hydraulic Diameter ($D_H$) is often substituted for diameter D. Hydraulic Diameter ($D_H$) represents the effective diameter of a circular cross-section that behaves the same as a non-circular cross-section. The Hydraulic Diameter ($D_H$) equation is:

$$H_D = \frac{4A}{p}$$

where A is the cross-sectional area of the lumen, and
p is the summation of the perimeter of all of the luminal walls on cross-section.

Combining these two equations, the standard Hagen-Poiseuille Law flow equation for a particular Hydraulic Diameter ($D_H$) is:

$$Q = \frac{\Delta P \pi D_H^4}{128 \mu L}$$

Using the Ohm's Law analogy for fluid flow, produces the equation:

$$Q = \frac{\Delta P}{R}$$

where R is the Resistance (to fluid flow), given thus by the equation:

$$R = \frac{128 \mu L}{\pi D_H^4}$$

As differing lumen cross-sections 136, 154 are arrayed serially in the systems being discussed, the serial resistance equation will be used, the equation being:

$$R_T = R_1 + R_2 + R_3$$

where $R_T$ is the total resistance, and
$R_1$, $R_2$, $R_3$, etc. are individual serial resistances.

The intention is to compare the total (flow) resistance of a first thrombectomy system ($R_{T1}$) with the total resistance of a second thrombectomy system ($R_{T2}$). Thus, the constant 128/π can be removed from the comparative term, leaving $\mu L/D_H^4$. Additionally, though blood is non-Newtonian, and thus may exhibit variance in viscosity at different shear rates, the variation of the effective viscosity of a thrombus/macerated thrombus/blood slurry is not expected to be significant among the different lumen conditions described. Therefore, the viscosity (μ) term may also be removed from the comparative term. This leaves a comparative term of:

$$\text{Comparative Flow Resistance } (R_C) = L/D_H^4$$

Comparative Flow Resistance ($R_C$) can be calculated using the units (1/cm³).

Returning to the standard thrombectomy catheter 140 of FIG. 3, the entire length $L_1$ of the catheter in some models is about 140 cm and has a circular cross-sectional diameter $D_1$ of its lumen 138 of about 0.11 cm (0.042 inches). Because the lumen 138 is circular, 0.11 cm (0.042 inches) is also the Hydraulic Diameter ($D_H$). In comparison, the embodiment of the thrombectomy system 100 of FIG. 4, includes a first length $L_2$ representing the length of the distal tube 114 of the thrombectomy catheter 106, and in one embodiment $L_2$ is about 25 cm. In this particular embodiment, the lumen 130 of the distal tube 114 may have a circular cross-sectional diameter $D_2$ of its lumen 130 of about 0.15 cm (0.060 inches) The thrombectomy system 100 is inserted through a guiding catheter 108 having a lumen inner diameter of about 0.183 cm (0.072 inches) and a length of about 100 cm, thus having a flow length $L_3$ of about 100 cm. Assuming a support member 126 embodiment comprising a substantially rectangular cross-section stainless steel wire having a minor dimension of about 0.0305 cm (0.012 inches) and a major dimension of about 0.0508 cm (0.020 inches), the Comparative Flow Resistance ($R_C$) may be calculated for the standard thrombectomy catheter 140 and the thrombectomy system 100 in their "no guidewire" configurations of FIGS. 3 and 4, respectively. Table 1 demonstrates that the Comparative Flow Resistance ($R_{C1}$) of the thrombectomy system 100 is only about 15% the Comparative Flow Resistance ($R_{C2}$) of the standard thrombectomy catheter 140.

TABLE 1

| Condition | $R_{c1}$ (1/cm³) | $R_{c2}$ (1/cm³) | $R_{c1}/R_{c2}$ |
| --- | --- | --- | --- |
| No Guidewire (FIGS. 3 and 4) | 160,822 | 1,080,926 | 0.15 |
| Guidewire (FIGS. 5 and 6) | 320,704 | 1,080,926 | 0.30 |

The standard thrombectomy catheter 140 in FIG. 5 has a guidewire 134 within the length of its lumen 138. The thrombectomy system 100 of FIG. 6 has a 0.014" diameter guidewire 134 (0.036 cm) within the length of the lumen 130 of the distal tube 114 and the inner lumen 110 of the guiding catheter 108. The thrombectomy system 100 of FIG. 6 also has a support member 126 having cross-sectional dimensions of 0.0305 cm×0.0508 cm (0.012 inches×0.020 inches) within the length of the inner lumen 110 of the guiding catheter 108. Table 1 demonstrates that the Comparative Flow Resistance ($R_{C1}$) of the thrombectomy system 100 is only about 30% the Comparative Flow Resistance ($R_{C2}$) of the standard thrombectomy catheter 140. This means that at a particular negative pressure gradient, the aspiration flow rate through the thrombectomy system 100 can be as much as 3.33 times more than the aspiration flow rate through the standard thrombectomy catheter 140.

A test was performed wherein a 30 ml vacuum was locked onto an extraction syringe, and sealed with a closed stopcock. The extraction syringe and stopcock were then attached to a catheter/catheter system and the tip of the catheter placed in a beaker of water. The stopcock was then opened and the time was measured for the 30 ml syringe to fill with water. The data is listed in Table 2.

TABLE 2

| System | Time to fill 30 ml syringe (seconds) |
| --- | --- |
| Medtronic Export AP | 25 |
| Prototype with 25 cm long, 0.147 cm (.058 inches) ID distal tube, and 0.0305 cm × 0.0508 cm (0.012 inches × 0.020 inches) support member in 0.183 cm (.072 inches) ID × 100 cm long guiding catheter - distal tube extending 25 cm from guiding catheter | 7.2 |
| Prototype with 25 cm long, 0.147 cm (.058 inches) ID distal tube, and 0.0305 cm × 0.0508 cm (0.012 inches × 0.020 inches) support member in 0.183 cm (.072 inches) ID × 100 cm long guiding catheter - distal tube extending 5 cm from guiding catheter | 6.7 |

Published data using a similar 30 ml syringe water vacuum test shows Peak Extraction Rate (ml/sec) for several thrombus aspiration catheters. The peak extraction rate ranged from 0.94 ml/second to 1.71 ml/second (Table 3). Published in "Comparison of Dimensions and Aspiration Rate of the Pronto® V3, Pronto® LP, Export® XT, Export® AP, Fetch®, Xtract™, Diver C.E.™ and QuickCat™ Catheters" (ML1623 Rev. F 12/09 c2009 Vascular Solutions, Inc.) In comparison, the prototype thrombectomy system 100 tested in the two conditions of Table 1, demonstrated an average extraction rate of 3.6 ml/second to 4.0 ml/second, 2.1 to 2.3 times the peak extraction rate of the highest performing catheter (Pronto V3) in the published data set. And it should be mentioned that the designs of the thrombus aspiration catheters of the Table 3 test data are such that there is no guidewire within their lumen (as in FIG. 3) during aspiration, and the prototype thrombectomy system 100 tested also did not have a guidewire within its lumens during testing (as in FIG. 4). In use, for aspirating body fluids and materials such as blood and thrombus, embodiments of the thrombectomy system 100 of the present invention have significantly higher potential to remove thrombus more quickly and more completely than a standard thrombectomy catheter 140, such as those represented in the published data. The amount of vacuum present at the lumen 130 at the distal end 116 of the distal tube 114 may be up to twice that (or more) of the amount of vacuum present at the distal tip of the lumen 138 of a standard thrombectomy catheter 140, which attests to larger forces pulling the thrombus 104 into the lumen 130.

TABLE 3

| System | Peak Extraction Rate (ml/sec) of water evacuated by 30 ml syringe |
| --- | --- |
| Pronto ® V3 (Vascular Solutions, Inc.) | 1.71 |
| Pronto ® LP (Vascular Solutions, Inc.) | 0.94 |
| Export ® XT (Medtronic, Inc.) | 1.27 |
| Export ® AP (Medtronic, Inc.) | 1.44 |
| Fetch ® (Medrad/Possis) | 1.55 |
| Xtract ™ (Volcano/Lumen Biomedical) | 1.24 |
| Diver C.E. ™ (Invatec) | 1.04 |
| QuickCat ™ (Spectranetics) | 1.11 |

Figure 15:
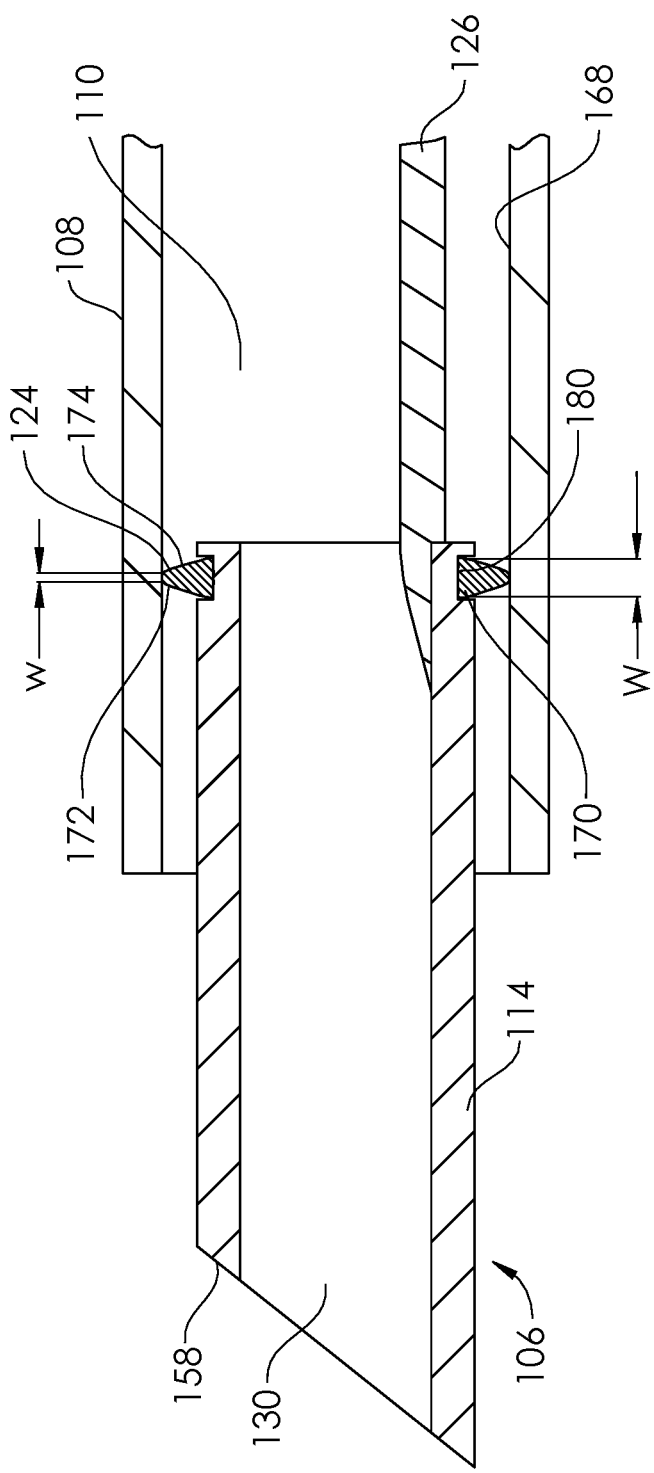
FIG. 15 is a sectional view of an aspiration system according to an embodiment of the present invention.
Figure 17:
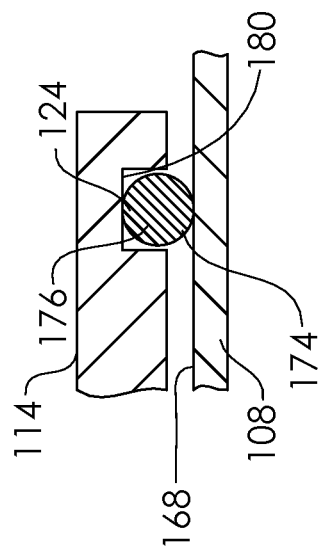
FIG. 17 is a sectional view of an aspiration system according to an embodiment of the present invention.
Figure 16:
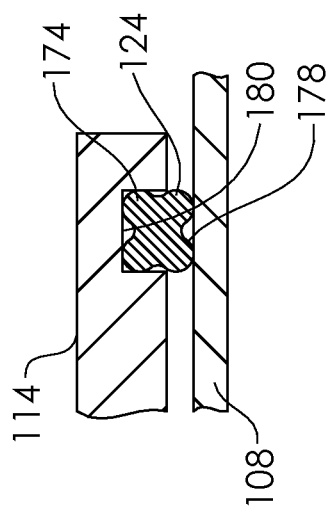
FIG. 16 is a sectional view of an aspiration system according to an embodiment of the present invention.

FIG. 15 illustrates an embodiment of the thrombectomy system 100, wherein the thrombectomy catheter 106 includes a sealing member 124 that is an o-ring 174 having a custom cross-section having a wider base portion 170 having a width W and a wiper blade portion 172 having a width w, that is smaller than width W. Though the maximum outer diameter of the o-ring 174 of this embodiment should be larger than the inner diameter of the inner lumen 110 of the guiding catheters 108 with which it is compatible (for sealable coupling), the thinner the width w of the wiper blade portion, the less drag and the greater feel is achieved. The distal tube 114 includes an annular groove 180, having a width large enough to seat the base portion 170 of the o-ring 174. In FIG. 15, the distal tube 114 of the thrombectomy catheter 106 is shown with a distal skive 158, but without a proximal skive (160 in FIG. 12). As mentioned, numerous combinations of the skives 158, 160 are contemplated and are not limiting. FIG. 16 illustrates a closeup of an embodiment of the thrombectomy system 100, wherein the thrombectomy catheter 106 includes a sealing member 124 that is an o-ring 174 having an x-shaped cross-section 178. FIG. 17 illustrates a closeup of an embodiment of the thrombectomy system 100, wherein the thrombectomy catheter 106 includes a sealing member 124 that is an o-ring 174 having a circular cross-section 176. Numerous other o-ring cross-sections are contemplated. The annular groove 180 has enough width to seat the corresponding o-ring cross-sections 176, 178 of the embodiments of FIGS. 16 and 17. A lip, such as the distally facing lip 166 of the embodiment of the thrombectomy system 100 of FIG. 11, or a seal, such as the o-ring 174 having a wiper blade portion 172 of FIG. 15, may have several optional embodiments in which their maximum outer diameter is constructed to different diameters in relation to the inner diameter of the guiding catheter 108. For example, in some embodiments, the outer diameter may be in rubbing relation to the inner diameter of the guiding catheter 108. In some embodiments, the outer diameter may be in touching relation to the inner diameter of the guiding catheter 108. In some embodiments, the outer diameter may be in close clearance relation to the inner diameter of the guiding catheter 108. In some embodiments, the outer diameter may be in a non-touching relation to the inner diameter of the guiding catheter 108. In some embodiments, there may me multiple features, having a combination of these relationships (rubbing, touching, etc.). In some embodiments, the sealing member 124 may be an inflatable balloon, whose diameter and/or inflation pressure may be controlled.

Figure 18:
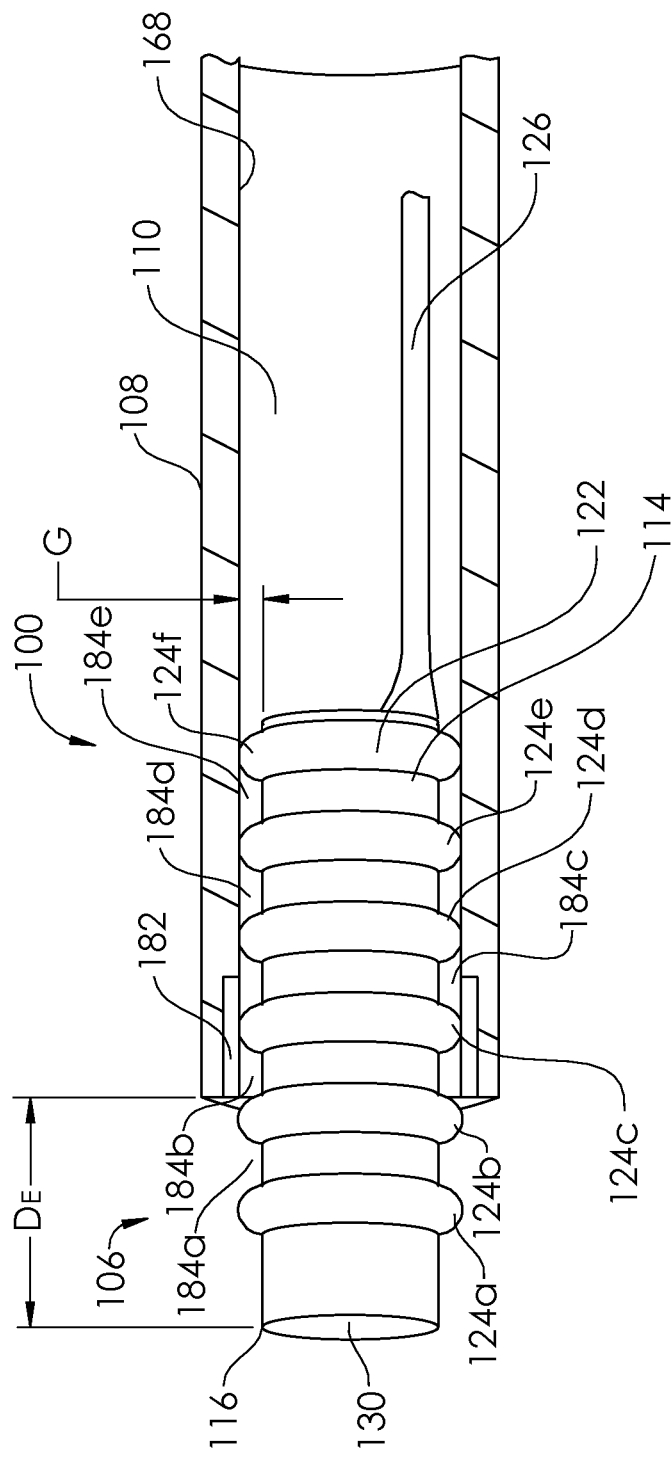
FIG. 18 is a partially sectional view of an aspiration system according to an embodiment of the present invention.

FIG. 18 illustrates an embodiment of a thrombectomy system 100 having multiple sealing members 124, denoted by 124a, 124b, 124c, 124d, 124e, and 124f. In some embodiments, the sealing members 124a-f may be annular seals, such as any of the embodiments described herein. In some embodiments, the guiding catheter 108 may be from a different or unknown supplier and it may be difficult to know the true inner diameter of the inner lumen 110 along a significant length of the distal portion of the guiding catheter 108. However, it may be possible for the user to measure the inner diameter at a distal portion 182 of the guiding catheter 108 (for example, using sterile pin or plug gauges). The multiple sealing members 124a-f make it possible to adjust the distance DE that the inner tube 114 extends from the guiding catheter 108, while assuring a sealing relationship between the particular sealing member 124a-f and the inner diameter of the guiding catheter 108 at the distal portion 182. For example, when sealing member 124a is sealingly engaged with the inner diameter of the guiding catheter 108 at the distal portion 182, DE is much shorter than when sealing member 124f is sealingly engaged with the inner diameter of the guiding catheter 108 at the distal portion 182. Thus, in use by the physician, the distal end 116 of the distal tube 114 can be brought into ideal position in relation to the thrombus 104 (FIGS. 1 and 2), for example, just proximal to the thrombus 104. Additionally, the short axial length of contact of each of the sealing members 124a-f with the inner wall 168 of the guiding catheter 108 summed together is much less than if the entire outer cylindrical surface 122 of the distal tube 114 were a cylindrical seal, and this lowers the drag and increases the feel. Multiple axial spaces 184a-e, located between the sealing members 124a-f, represent the majority of the length of the distal tube 114, and thus gap G can be large enough (e.g. 0.0076 cm (0.003 inches) or greater per side) so that even in tortuosities of the blood vessel 102, where the catheters may be curved or angled, the drag is not unacceptably increased and the feel is not unacceptably decreased.

Figure 19:
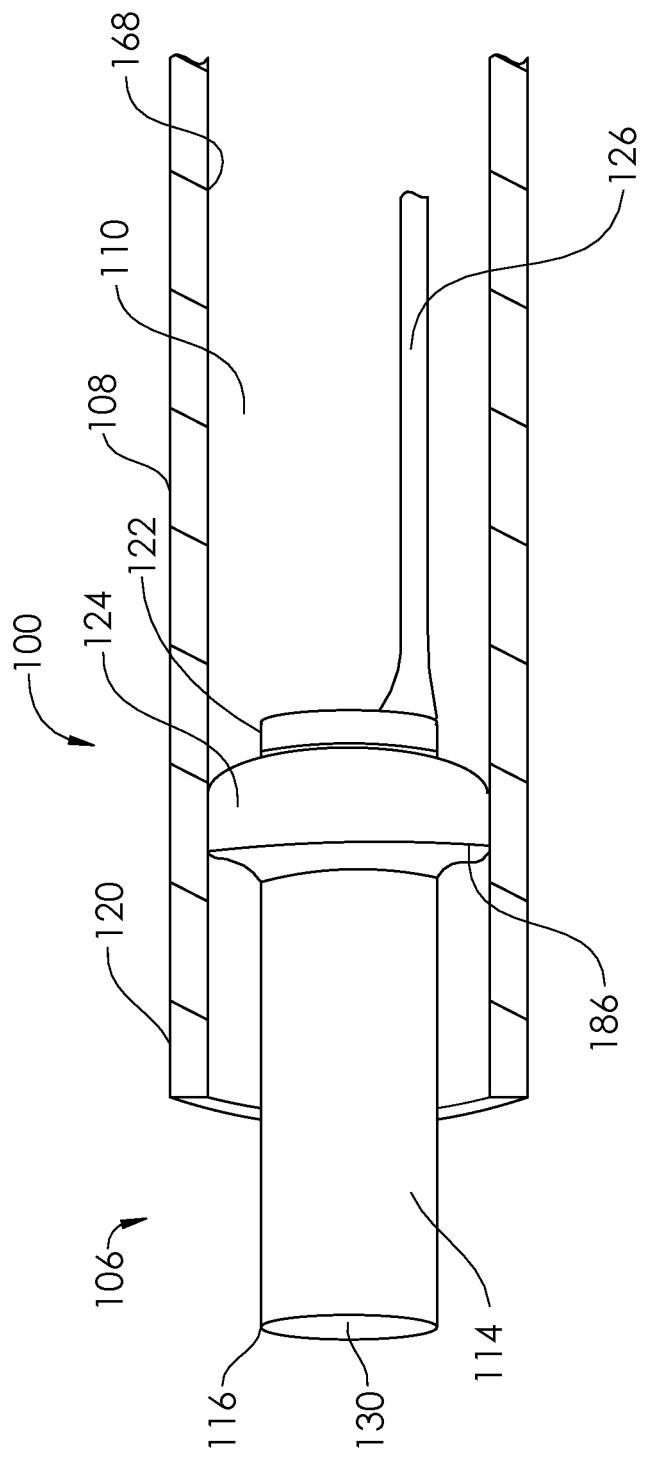
FIG. 19 is a partially sectional view of aspiration system according to an embodiment of the present invention.

FIG. 19 illustrates an embodiment of a thrombectomy system 100 having one or more sealing members 124 comprising a hydrogel 186 annularly attached around the outer cylindrical surface 122 of the distal tube 114 of the thrombectomy catheter 106. In some embodiments, the maximum outer diameter of the sealing member 124 comprising a hydrogel 186 may be less than the inner diameter of the inner lumen 110 of the guiding catheter when the hydrogel is in a non-hydrated or substantially non-hydrated state. The maximum outer diameter of the sealing member 124 comprising a hydrogel 186 may become greater than the inner diameter of the inner lumen 110 of the guiding catheter when the hydrogel is in a partially hydrated, substantially hydrated, or fully hydrated state. This feature allows the thrombectomy catheter 106 to be advanced with little drag down the guiding catheter 108 while the sealing member 124 comprising a hydrogel 186 is becoming hydrated. As the sealing member 124 comprising a hydrogel 186 becomes substantially hydrated, the sealing member 124 will likely be already placed at the location of choice in relation to the distal end 120 of the guiding catheter 108. In this position, the larger maximum outer diameter of the sealing member 124 will seal against the inner wall 168 of the inner lumen 110 of the guiding catheter. In some embodiments, the hydrogel 186 has high lubricity in order to allow movement with minimal drag while the sealing member 124 is in sealing relationship against the inner wall 168 of the inner lumen 110 of the guiding catheter. In some embodiments, the high lubricity is achieved by the hydrogel having a higher water holding capacity. In some embodiments, the hydrogel 186 has relatively lower lubricity in order to minimize accidental axial movement of the sealing member 124 in relation to the guiding catheter. In some embodiments, the high lubricity is achieved by the hydrogel having a lower water holding capacity. In some embodiments, the hydrogel comprises p-HEMA.

Figure 20:
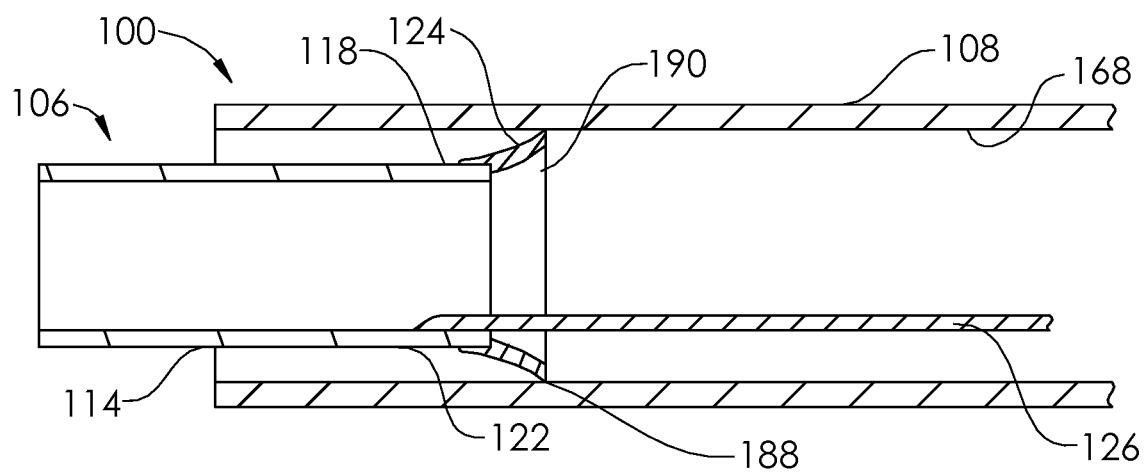
FIG. 20 is a sectional view of an aspiration system according to an embodiment of the present invention.

FIG. 20 illustrates an embodiment of a thrombectomy system 100 having one or more sealing members 124 coupled to the proximal end 118 of the distal tube 114 of the thrombectomy catheter 106. In some embodiments, the one or more sealing member 124 is secured to the outer cylindrical surface 122 of the distal tube 114. In some embodiments, the sealing member 124 is a cone-shaped or bowl-shaped membrane 190 configured to seal against the inner wall 168 of the guiding catheter 108 at the wipe end 188.

Figure 21:
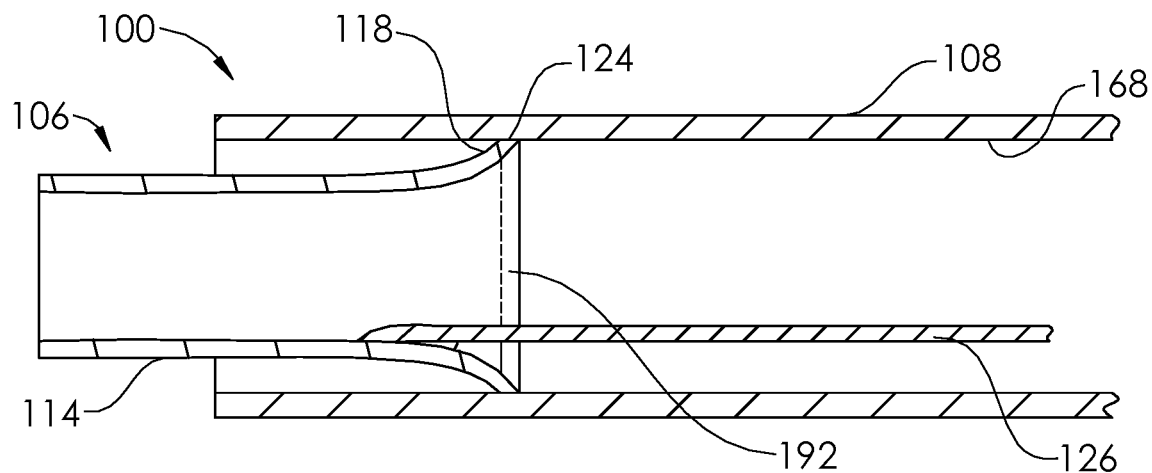
FIG. 21 is a sectional view of an aspiration system according to an embodiment of the present invention.

FIG. 21 illustrates an embodiment of a thrombectomy system 100 having a sealing member 124 which is formed from the proximal end 118 of the distal tube 114 of the thrombectomy catheter 106. In some embodiments, the sealing member 124 is formed by flaring the proximal end 118 of the distal tube 114, so that a seal ring 192 is created, for sealing against the inner wall 168 of the guiding catheter 108.

Figure 22:
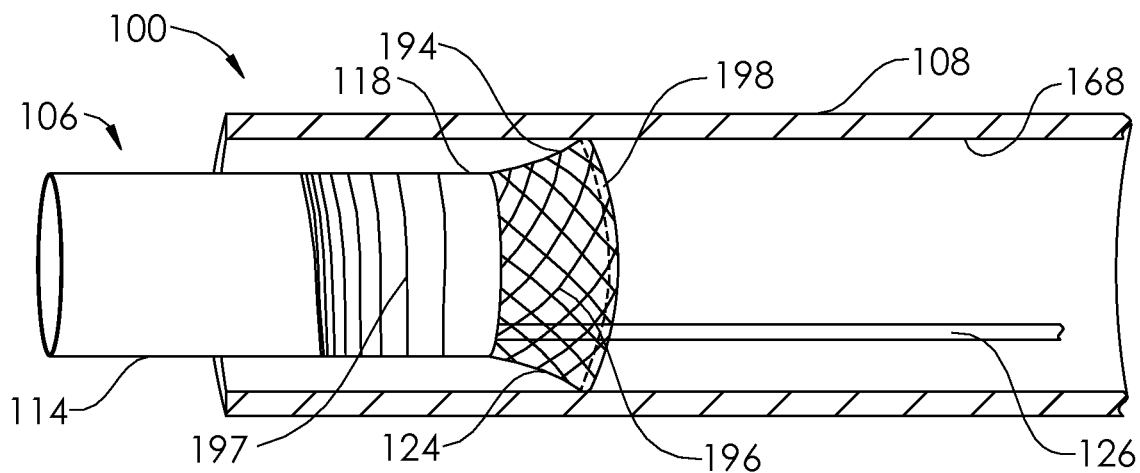
FIG. 22 is a partially sectional view of an aspiration system according to an embodiment of the present invention.

FIG. 22 illustrates an embodiment of a thrombectomy system 100 having a sealing member 124 coupled to the proximal end 118 of the distal tube 114 of the thrombectomy catheter 106. In some embodiments, the sealing member 124 may comprise a cone-shaped or bowl-shaped structure 194. In some embodiments, the structure 194 may be formed from a tubular braid 196. In some embodiments, the tubular braid 196 may be braided from metallic wires. In some embodiments, the tubular braid 196 may be braided from Nickel-Titanium wires. In some embodiments, the tubular braid 196 may be heat set into a cone shape or a bowl shape. In some embodiments, the tubular braid 196 may be dip coated. In some embodiments, the tubular braid 196 may be dip coated after having been heat set. In some embodiments, the tubular braid 196 may be dip coated with polyurethane. In some embodiments, the tubular braid 196 may be dip coated with silicone. In some embodiments, the dip coating material may form a seal ring 198 for sealing against the inner wall 168 of the guiding catheter 108. In some embodiments, the tubular braid 196 is formed so that the seal ring 198 is forced against the inner wall 168 of the guiding catheter 108. In some embodiments, the dip-coated, formed tubular braid 196 is sufficiently compressible that it can be pushed through the inner lumen 110 of a guiding catheter 108. FIGS. 20-22 illustrate embodiments of a thrombectomy catheter 106 in a condition when it is at least partially extended axially out of the inner lumen 110 of the guiding catheter 108. In some embodiments, a stiffness transition member 197 (FIG. 22) may be incorporated into the distal tube 114. In some embodiments, the stiffness transition member 197 may comprise a hypo tube that is spiral cut (e.g. laser cut) with decreasing pitch moving distally. A number of other methods known in the art may be used to create a transition in stiffness, such as use of composite materials, a transition of polymeric materials, or transitioning braids or coils.

Figure 23:
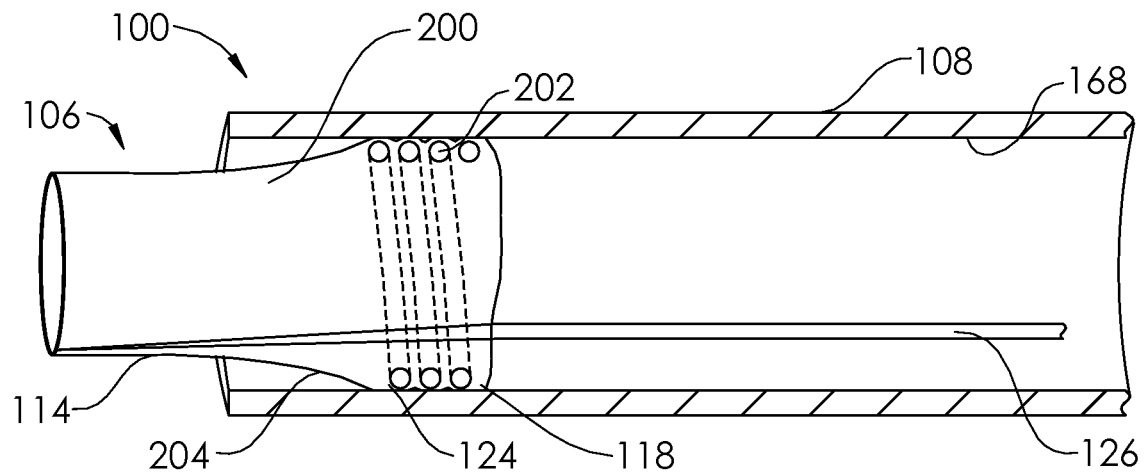
FIG. 23 is a partially sectional view of an aspiration system according to an embodiment of the present invention.

FIG. 23 illustrates an embodiment of an aspiration (thrombectomy) system 100 having a sealing member 124 which is the proximal end 118 of the distal tube 114 of the aspiration (thrombectomy) catheter 106. In some embodiments, the entire distal tube 114 comprises a windsock-like-member 200 having a tapered portion 204. The proximal end 118 has an increased diameter and is supported radially by a stent section 202. In some embodiments, the stent section 202 is a coil. In some embodiments, the stent section 202 is a laser machined metal tube. In some embodiments, the stent section 202 is a tubular braid.

Figure 24:
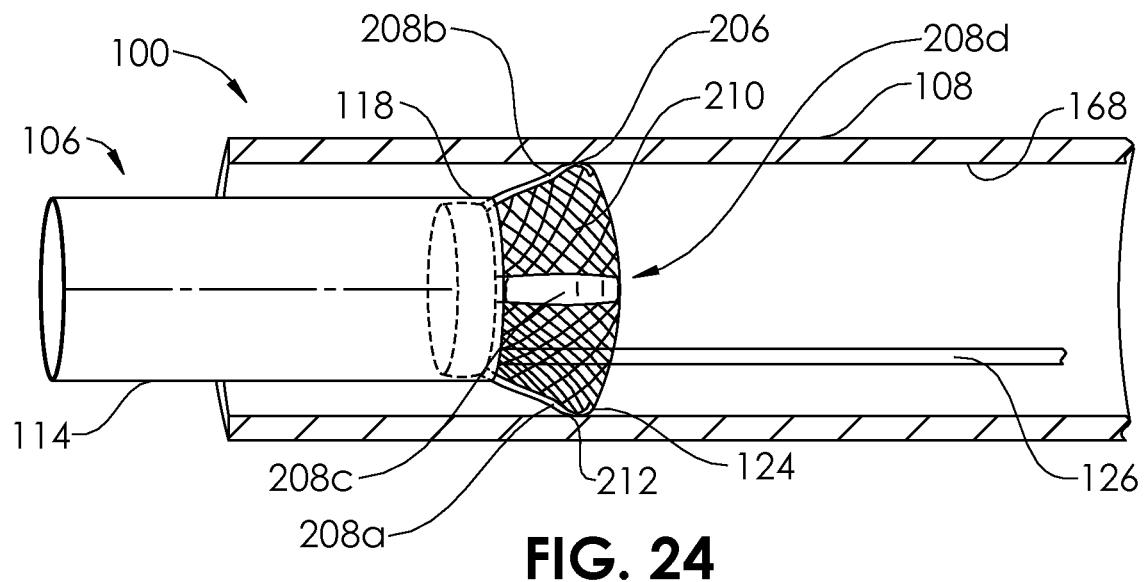
FIG. 24 is a partially sectional view of an aspiration system according to an embodiment of the present invention.

FIG. 24 illustrates an embodiment of an aspiration (thrombectomy) system 100 having a sealing member 124 which is coupled to the proximal end 118 of the distal tube 114 of the aspiration (thrombectomy) catheter 106. A structure 206 comprising two or more fingers 208*a-d* is secured to the proximal end 118 of the distal tube 114. In some embodiments, the structure 206 is welded or secured using other methods to the support member 126. In some embodiments, the structure 206 is flared outwardly towards the proximal end, leading to a sealing ring 212. In some embodiments, the structure 206 includes a covering 210 over the fingers 208*a-d*. In some embodiments, the covering 210 is a membrane.

FIG. 25 illustrates an embodiment of an aspiration (thrombectomy) system 100 of the present invention being used in conjunction with the deployment of a stent 214. In the method for performing this procedure with the aspiration (thrombectomy) system 100, the interventionalist (physician) places a guiding catheter 108 into the blood vessel 102. For example, the interventionalist may place the distal end 120 of the guiding catheter 108 into the ostium of a coronary artery. The interventionalist may next place a guidewire 134 across an atherosclerotic lesion 218, which may or may not have thrombus 104. The interventionalist next tracks an embodiment of the aspiration (thrombectomy) catheter 106 of the present invention over the guidewire 134 and through the guiding catheter 108, until the distal end 116 of the distal tube 114 exits the guiding catheter. The interventionalist the tracks the distal end 116 of the distal tube to a target area 112, for example, just proximal to the location of the atherosclerotic lesion 218. The sealing member 124 is positioned within the guiding catheter 108, so that it will be sealingly coupled to the guiding catheter at least while aspiration is being performed. The interventionalist then tracks a dilatation catheter 216 over the guidewire 134, through the guiding catheter 108, and across the atherosclerotic lesion 218. The vacuum source 146 (FIGS. 1 and 2) is coupled to the side port 152 of the y-connector 148, and the stent 214 is expanded by the dilatation balloon of the dilatation catheter 216 while the thrombectomy system performs aspiration. This lowers the possibility that residual thrombus (clot) is carried downstream, causing potential complications. It also lowers then possibility that residual thrombus remains trapped between the stent 214 and the now dilated atherosclerotic lesion 218. When the interventionalist deems the result satisfactory, the interventionalist takes final fluoroscopic (or other) images, and then removes the devices.

FIGS. 26A-26B illustrate an attachment joint 228 and method for joining/coupling the support member 126 to the distal tube of a thrombectomy catheter 106 according to an embodiment of the present invention. A tapered half-pipe member 220 comprising a partial cylinder is secured at its large end 222 to the proximal end 118 of the distal tube 114 by adhesive, epoxy, welding, soldering, embedding or other attachment methods. The small end 224 of the tapered half-pipe member 220 is secured to the support member 126 by adhesive, epoxy, welding, soldering, embedding or other attachment methods. Though the skives 158, 160 are not pictured in FIG. 26, they are compatible with this joining embodiment and method. The tapered half-pipe member 220 allows for a gradual transition that provides an open area 226, so that flow is not compromised. In some embodiments, the outer radius 227 of the tapered half pipe member 220 is configured to substantially match the inner diameter of the distal tube 114. In some embodiment, the inner radius 229 of the tapered half pipe member 220 is configured to substantially match the outer diameter of the distal tube 114. These embodiments enable a close fit and thus a relatively low profile.

Figure 27:
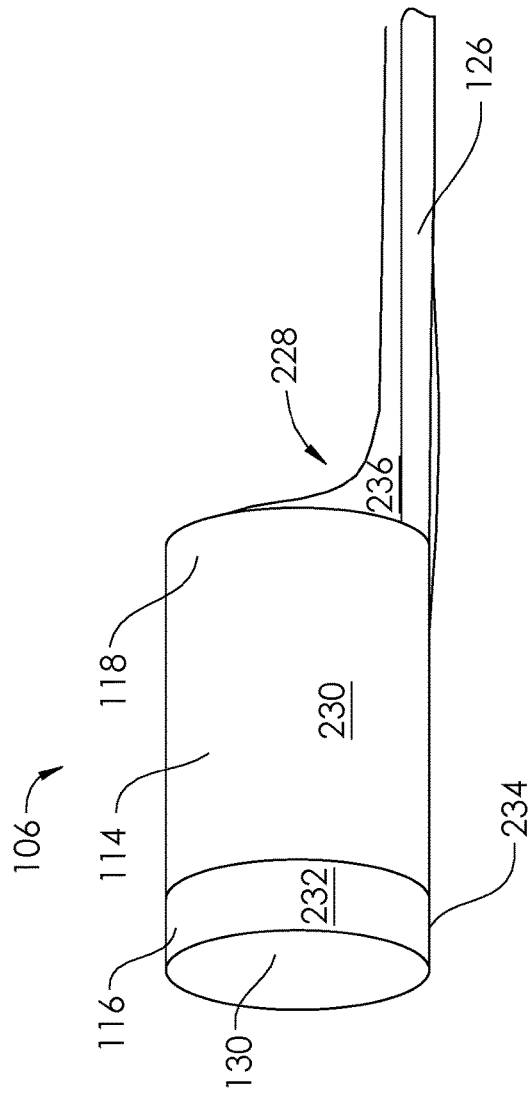
FIG. 27. is a perspective view of an aspiration catheter assembled with a dipping process according to an embodiment of the present invention.

FIG. 27 illustrates a dipping process for an attachment joint including but not limited to the attachment joint 228 of FIG. 26. After the attachment joint 228 is assembled, a first dipping step 230 is performed over the majority of the length of the distal tube 114. In some embodiments, the distal tube 114 may comprise a lubricious inner tube layer, such as PTFE, and a spring coil inner layer around the PTFE inner tube layer. In some embodiments, a medium durometer dipping material, such as polyurethane or PEBAX, is applied to the distal tube. In some embodiments, the medium durometer material may have a durometer of about 63D. A second dipping step 232 is performed with a low durometer material, such as polyurethane of PEBAX, to form a "Soft" tip 234. In some embodiments, the low durometer material may have a durometer of about 55D. A third dipping step 236 is performed with a high durometer material over the attachment joint 228. In some embodiments, the third dipping step 236 is performed over most or all of the length of the support member 126. In some embodiments, the high durometer material may have a durometer of about 72D. The result is a stiff, pushable catheter 106 that has a smooth transition at the attachment joint 228, a flexible distal tube 114 for tracking through the blood vessel 102 (FIGS. 1, 2 and 25) and a soft tip 234 for atraumatic characteristics within the blood vessel 102. A maximized lumen 130 cross-section area may be achieved in any of the embodiments resented herein by minimizing wall thickness and/or minimizing the thickness of any coating. Ultra-thin wall hypo tubes or polyimide tubes may be used in some embodiments. A dip coating of less than about 0.005 cm (0.002 inches) may be applied, and may include polyurethane. A dip coating of less than about 0.0025 cm (0.001 inches), or about 0.0018 cm (0.0007 inches) may be applied, and may include polyurethane.

Figure 28:
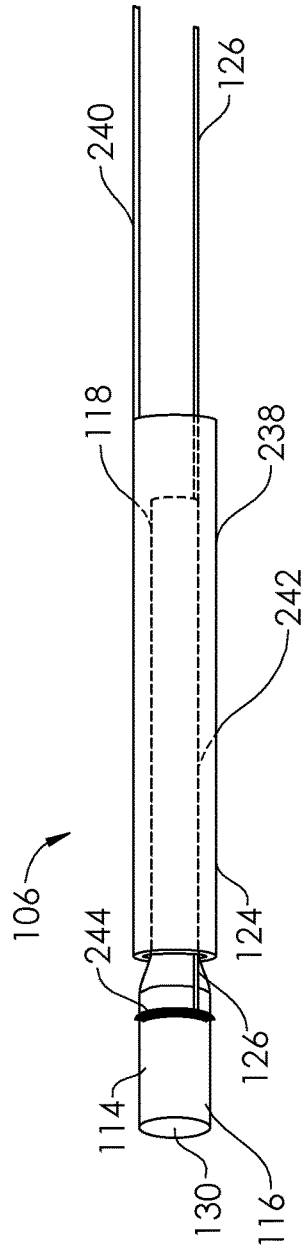
FIG. 28 is a perspective view of a distal section of an aspiration (thrombectomy) catheter according to an embodiment of the present invention.

FIG. 28 illustrates an embodiment of a thrombectomy catheter 106 of the thrombectomy system 100 having a sealing member 124 that is radially compressed over a compressible section 242 of the distal tube 114 during delivery through the guiding catheter 108 (FIG. 1). The compressible section 242 is held in a compressed state by a delivery sheath 238. In some embodiments, the delivery sheath 238 has a sheath push and pull rod 240 coupled to a portion thereof. In use, the thrombectomy catheter 106 is delivered through the guiding catheter 102 and into the blood vessel 102 by pushing the support member 126 and/or the sheath push and pull rod 240. When the distal end 116 of the distal tube 114 of the thrombectomy catheter 106 is located adjacent the target area 112 and the proximal end 118 of the distal tube 114 is within the inner lumen 110 of the guiding catheter 108 (FIG. 2), traction (tension) is applied on the sheath push and pull rod 240 while compression is applied on the support member 126, thus causing the delivery sheath 238 to be pulled proximally, and removed from the compressible section 242 of the distal tube 114, thus allowing the compressible section 242 to expand, and seal against the inner wall 168 (FIG. 15) of the guiding catheter 108. In some embodiments, the delivery sheath 238 may be retracted completely and removed completely from the guiding catheter 108. Though a guidewire 134 is not depicted in FIG. 28, this embodiment, like the other embodiments, may be used with a guidewire 134, as known in the art. In some embodiments, the support member 126 may be coupled to the distal tube 114 via a ring 244. In some embodiments, the ring 244 may be closer to the distal end 116 of the distal tube 114 than the proximal end 118.

Saline Injection Aspiration

Figure 29:
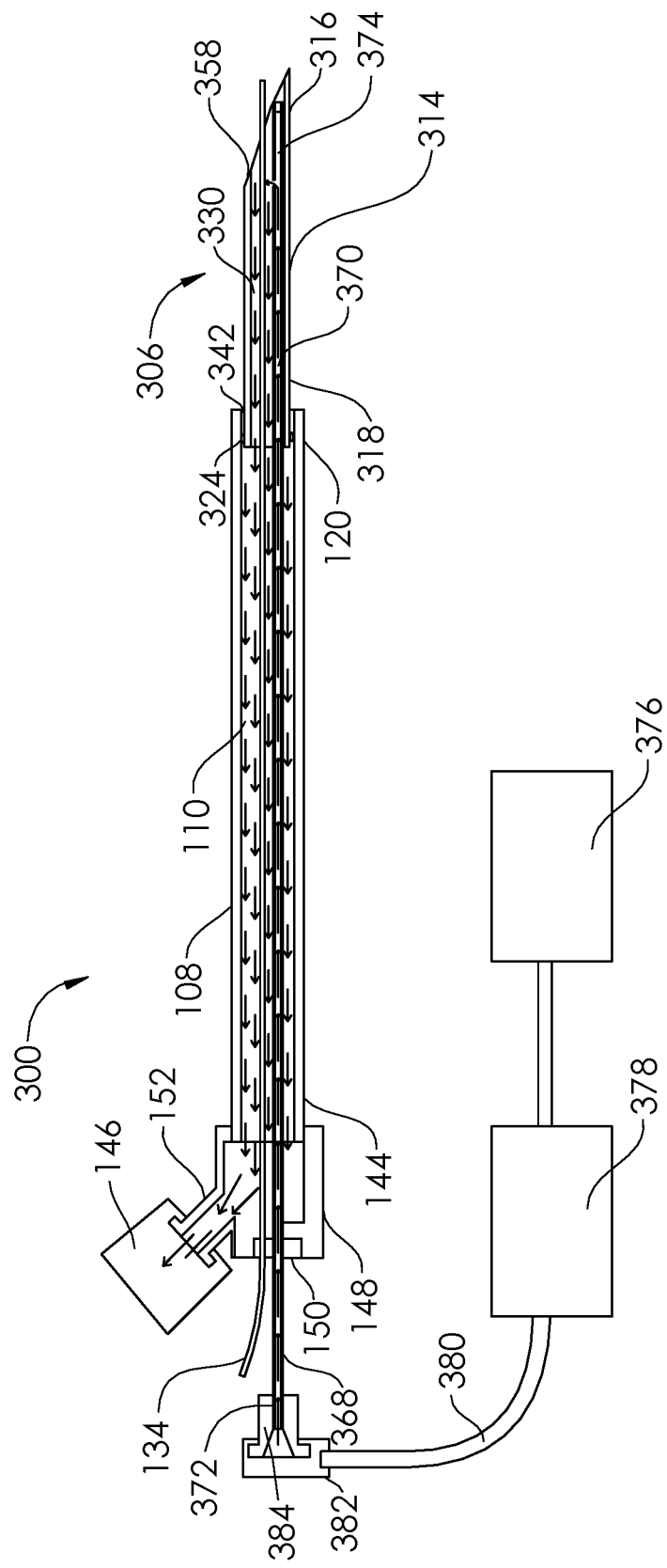
FIG. 29 is a sectional view of an embodiment of a saline injection aspiration (thrombectomy) catheter according to an embodiment of the present invention, with a guidewire in place through the lumens.

FIG. 29 illustrates a thrombectomy system 300 which incorporates the high pressure injection of a liquid, for example sterile saline solution, in order to macerate and aspirate thrombus 104 (FIG. 1). A guiding catheter 108 and a y-connector 148 having a proximal seal 150 and a sideport 152 are coupled to a vacuum source 146, as described in relation to the prior embodiments. A thrombectomy catheter 306 comprises a distal tube 314 having a distal end 316 and a proximal end 318, the proximal end 318 incorporating one or more sealing members 324 for sealing off an annulus 342 between the guiding catheter 108 and the distal tube 114, as described in relation to the prior embodiments. The distal tube 314 has an aspiration lumen 330. A support/supply tube 368, having a lumen 370, is coupled to the distal tube 314. The support/supply tube 368 serves the same purpose as the support member 126 of the prior embodiments, but is also a conduit (via the lumen 370) for high pressure saline, which is injected from the proximal end 372 to the distal end 374. The saline is supplied from a saline source 376 (e.g. saline bag, bottle) and pressurized by a pump 378, through a supply tube 380 and through a luer connector 382 which is connected to a luer hub 384 coupled to the support/supply tube 368. In some embodiments, the support/supply tube 368 comprises a hypo tube. In some embodiments, the support/supply tube 368 comprises stainless steel or nitinol.

Figure 30:
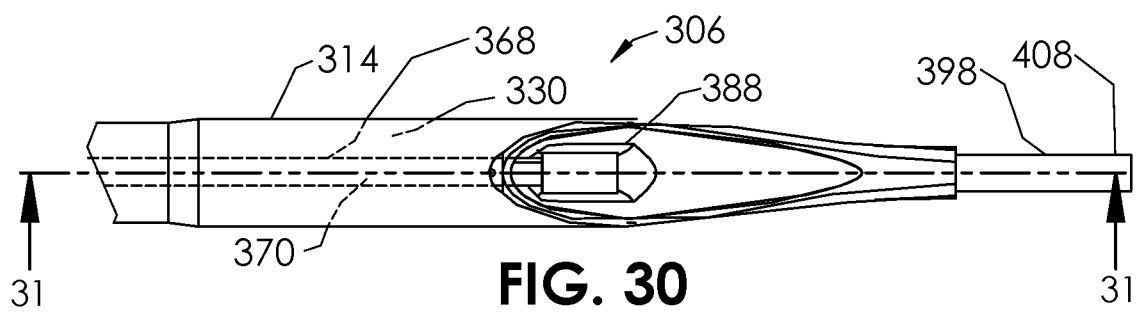
FIG. 30 is a plan view of a distal end of an alternative embodiment of the saline injection aspiration (thrombectomy) catheter of FIG. 29.
Figure 31:
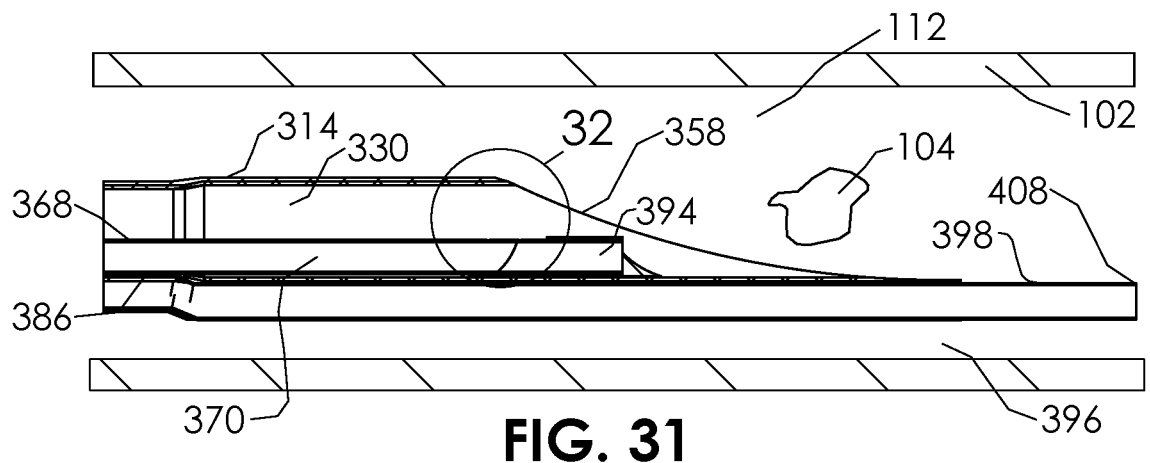
FIG. 31 is a sectional view of the saline injection aspiration (thrombectomy) catheter of FIG. 30, taken along the line 31-31.
Figure 32:
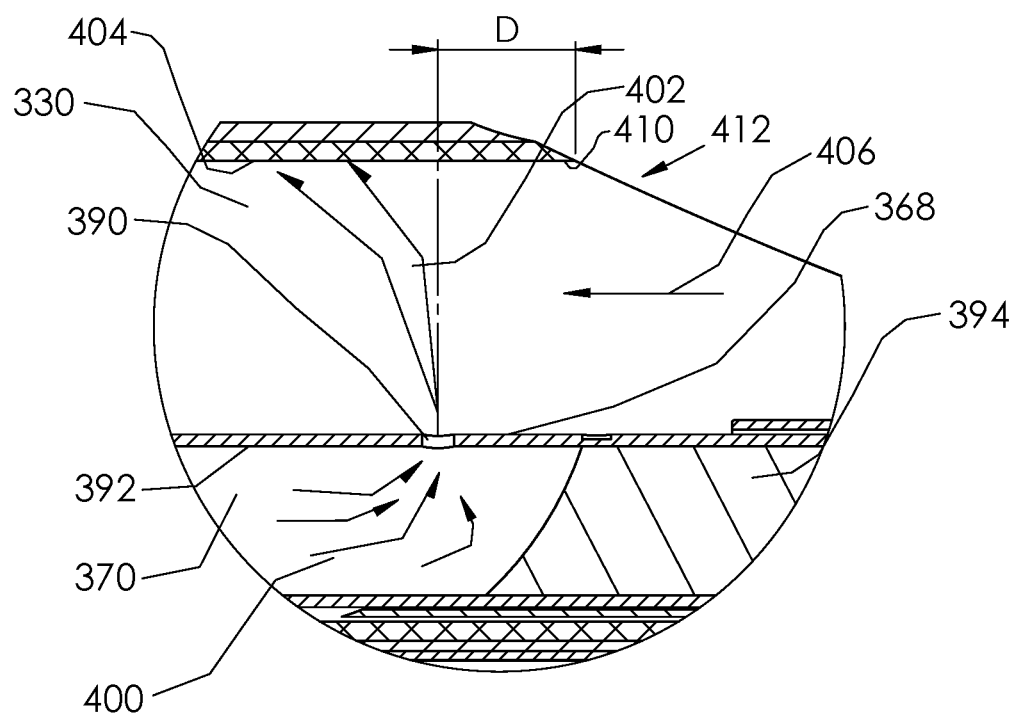
FIG. 32 is a detail view of the saline injection aspiration (thrombectomy) catheter of FIG. 31 within circle 32.

Turning to FIGS. 30-32, in some embodiments, the support/supply tube 368 may be coupled to the distal tube 314 by attachment materials 386, 388, including adhesive, epoxy, or melted/molded polymer materials. In some embodiments, the support/supply tube 368 has a closed distal end 394, and has one or more orifices 390 in its wall 392. In some embodiments, a rapid exchange tube 398 having a guidewire lumen 396 and a distal tip 408 may be coupled to the side of the distal tube 314, as seen in FIGS. 30 and 31, although the embodiment of FIG. 29 is shown with the guidewire 134 extending through the aspiration lumen 330 and the inner lumen 110.

After the user tracks the thrombectomy catheter 306 through the guiding catheter 108 and to the target area 112 in the blood vessel 102, the pump 378 is operated to inject high pressure saline through the support/supply tube 368. When the saline reaches the orifice (arrows 400), the saline is forced through the one or more orifices 390 and into the aspiration lumen 330. In some embodiments, the saline forms one or more jets 402 that impinge upon in inner wall 404 of the aspiration lumen 330, adjacent the one or more orifices 390. A high pressure is thus created in the aspiration lumen 330 adjacent the skive 358, forcing thrombus 104 into the aspiration lumen 330 in a direction generally shown by arrow 406. The thrombus 104 is then carried by the positive pressure gradient from distal to proximal from the aspiration lumen 330 into the inner lumen 110 of the guiding catheter 108 and out the sideport 152 of the y-connector 148 towards the vacuum source 146. In some embodiments, the one or more jets 402 serve to break up and macerate the thrombus 104, aiding in its subsequent passage through the lumens 330, 110. The mixing of the saline with the broken up thrombus 104 serves to lower its bulk viscosity, and thus aid in its passage through the catheter lumens with less resistance. In some embodiments, the one or more orifices 390 are located a distance D from the most proximal portion 410 of a distal opening 412 formed in the aspiration lumen 330 by the skive 358. In some embodiments, the distance D between the axial center of an orifice 390 and the most proximal portion 410 of the distal opening 412 is about 0.0508 cm (0.020 inches), or in some embodiments is 0.0508 cm±0.0076 cm (0.020 inches±0.003 inches).

Figure 33:
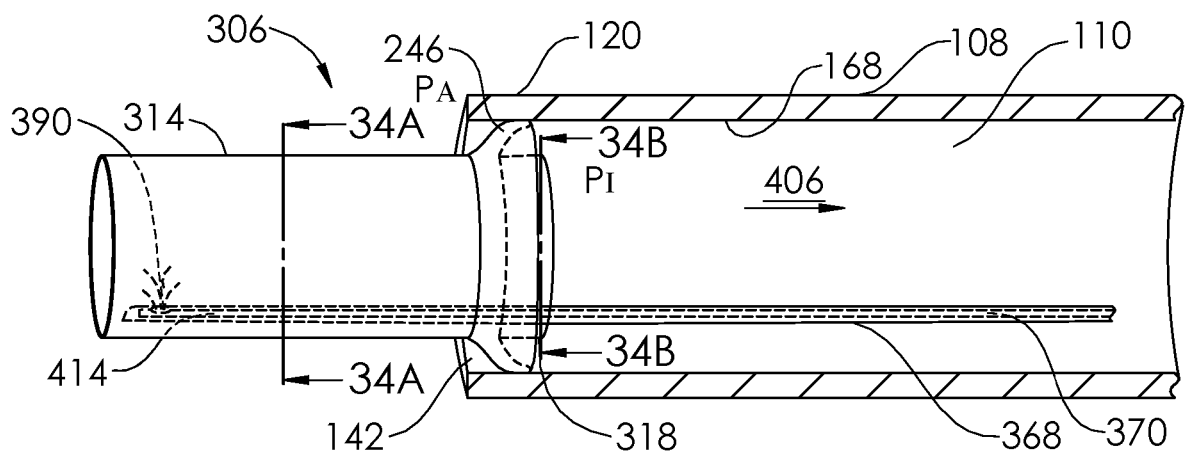
FIG. 33 is a perspective view of a distal section of a saline aspiration (thrombectomy) catheter according to an embodiment of the present invention.
Figure 34A:
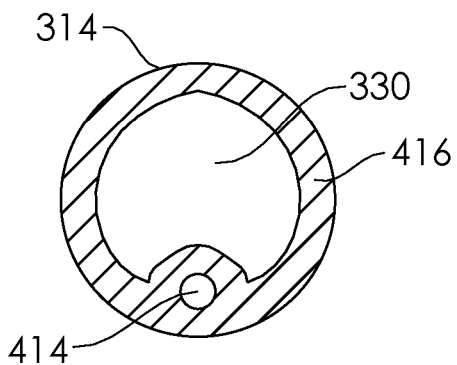
FIG. 34A is a cross-section of the saline injection aspiration (thrombectomy) catheter of FIG. 33, taken along the line 34A-34A.
Figure 34B:
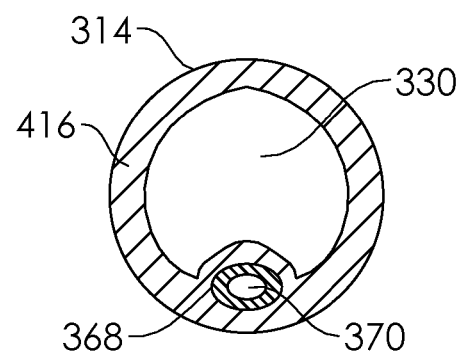
FIG. 34B is a cross-section of the saline injection aspiration (thrombectomy) catheter of FIG. 33, taken along the line 34B-34B.

FIGS. 33-34B illustrate an alternative embodiment of the support/supply tube 368, wherein the support/supply tube 368 couples to the distal tube 314 at the proximal end 318 of the distal tube 314. The distal tube 314 includes a wall 416 having a lumen 414. The support/supply tube 368 is coupled to the lumen 414 so that saline supplied through the support/supply tube 368 then passes through the lumen 414 distally, and exits the one or more orifices 390. In some embodiments, the lumen 414 may be provided by a separate polyimide tube that is embedded in the wall 416. In some embodiments, a proximally facing lip 246, for example, an annular seal extending in both a radial and proximal direction, is sealingly coupled to the distal tube 314. The high pressure saline injection through the lumen 370 of the support/supply tube 368, in combination with the vacuum source 146 (FIGS. 3-6), causes aspiration in a direction generally shown by arrow 406. The high pressure saline injection also creates an internal pressure $P_I$ within the inner lumen 110 of the guiding catheter 108 that is higher than the ambient pressure $P_A$ outside the distal end 120 of the guiding catheter 108. Because $P_I > P_A$, the proximally facing lip 246 is forced against the inner wall 168 of the inner lumen 110 of the guiding catheter 108, sealing the annulus 142. In some embodiments, the proximally facing lip 246 is thin and made from a flexible material (as in the distally facing lip 166 of FIG. 11), thus aiding is ability to be forced against the inner wall 168. In some embodiments, other embodiments of the sealing member 124 may be used, including, but not limited to, o-rings and hydrogel seals. In some embodiments, as seen in FIG. 34B, the distal end of the support/supply tube 368 may have an oval, elliptical or rectangular shape in order to allow a connection to the lumen 414 of the distal tube 314 that does not significantly compromise the size of the aspiration lumen 330 of the distal tube 314.

Figure 35:
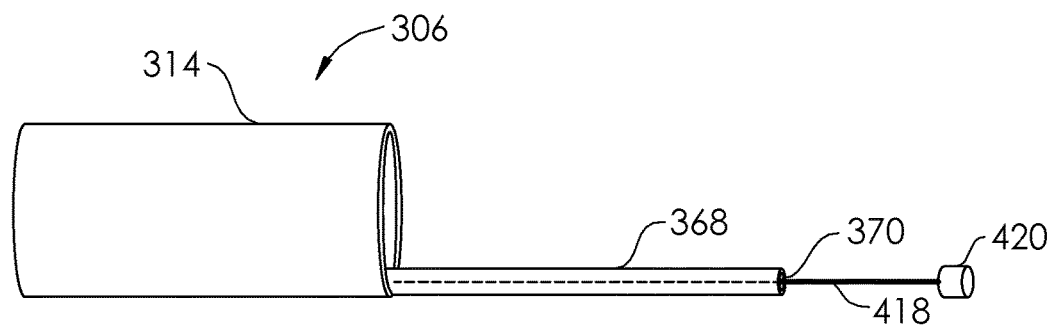
FIG. 35 is a perspective view of a proximal section of a saline aspiration (thrombectomy) catheter according to an embodiment of the present invention.

FIG. 35 illustrates an embodiment of the thrombectomy catheter 306 wherein the lumen 370 of the support/supply tube 368 may be decoupled from the luer hub 384 (FIG. 29) so that a stylet 418 may be inserted down the lumen 370 in order to impart additional stiffness and pushability. In some embodiments, the stylet 418 comprises stainless steel. In some embodiments, the support/supply tube 368 is a circular cross-section hypo tube and has an outer diameter of about 0.0549 cm (0.0216 inches) and an inner diameter of about 0.0483 cm (0.019 inches). In some embodiments, the stylet 418 has a circular cross-section and has an outer diameter of between about 0.038 cm (0.015 inches) and about 0.0457 cm (0.018 inches). In some embodiments, the sytlet 418 may have a hub 420 at its proximal end, in order to aid handling of the stylet 418 during insertion and removal.

Figure 36:
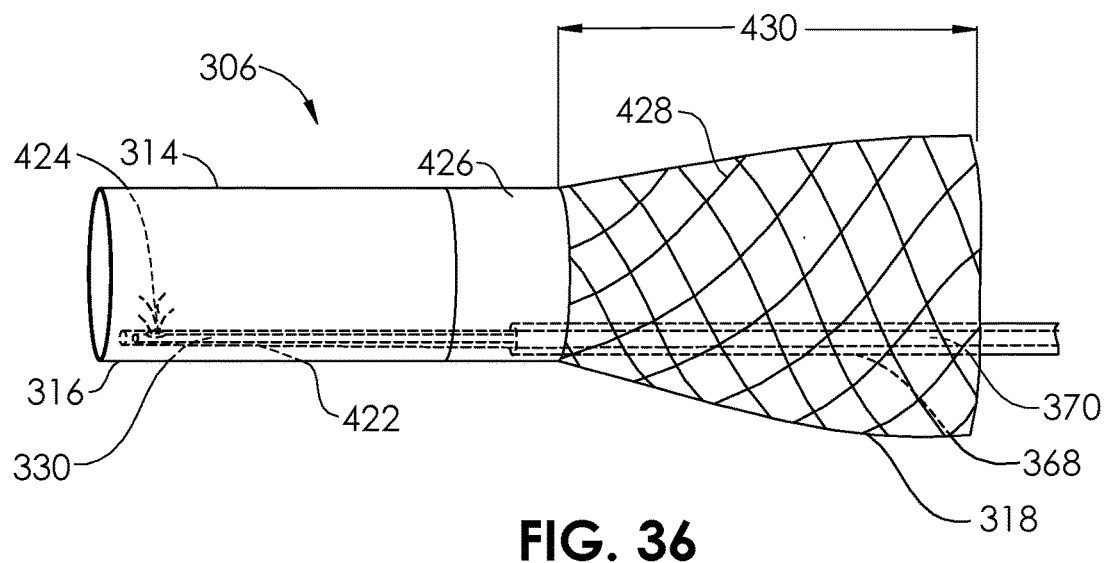
FIG. 36 is a perspective view of a distal section of a saline aspiration (thrombectomy) catheter according to an embodiment of the present invention

FIG. 36 illustrates an embodiment of the thrombectomy catheter 306 wherein the lumen 370 of the support/supply tube 368 is coupled to a smaller tube 422 within the aspiration lumen 330 of the distal tube 314. In some embodiments, the smaller tube 422 is a polyimide tube. In some embodiments, the smaller tube 422 is a tapered polyimide tube, tapering to a smaller diameter as it extends distally to its orifice 424. The support/supply tube 368 is also secured to a ring 426, which in some embodiments is closer to the distal end 316 than the proximal end 318 of the distal tube 314. The ring 426 is also secured to the distal tube 314. When the user pushes on the support/supply tube 368 at its proximal end, the force that in turn is applied to the ring 426 serves to "pull" the proximal end 318 of the distal tube 314, thus lessening the chances of compressing or deforming it.

The proximal end 318 of the distal tube 314 includes an expandable section 430 which may include a tubular mesh 428. The tubular mesh 428 may be encapsulated, for example by dipping in polyurethane of silicone, in order to create a sealed aspiration lumen 330 that extends from the distal end 316 to the proximal end 318. In some embodiments, the ring 426 may be constructed from a metal material, such as stainless steel or nitinol. In some embodiments, the ring 426 may include radiopaque material, such as platinum, for visualization on fluoroscopy or x-ray. The ring 426, and its use as the point of application of pushing or pulling, may be incorporated into one of the embodiments of the thrombectomy catheters 106 that do not have high pressure saline injection, but only aspiration. In this case, the support/supply tube 368 need not be a tube or hypo tube, but may also be a solid round wire flat wire.

Because of their use of the inner lumen 110 of the guiding catheter 108 as a portion of the extended lumen 128 (FIG. 2), any of the thrombectomy systems 100, 300 presented include the feature that one length (model) the thrombectomy catheter 106, 306 may be used on a variety of patient sizes and/or target area 112 depths. A single model of thrombectomy catheter 106, 306 may be adjusted to the desired depth in the blood vessel 102 so that it is adjacent to the target area 112, but the vacuum source 146 is still coupled at the same location, on the side port 152 of the y-connector 148. A large range of models (e.g. different lengths) of the thrombectomy catheter 106, 306 is not required. In some cases, this may mean that a single model of thrombectomy catheter 106 and/or a single model of thrombectomy catheter 306 may satisfy the majority of thrombectomy procedures performed in a particular catheterization laboratory or other health care facility, thus requiring a smaller area of shelf space.

Figure 38:
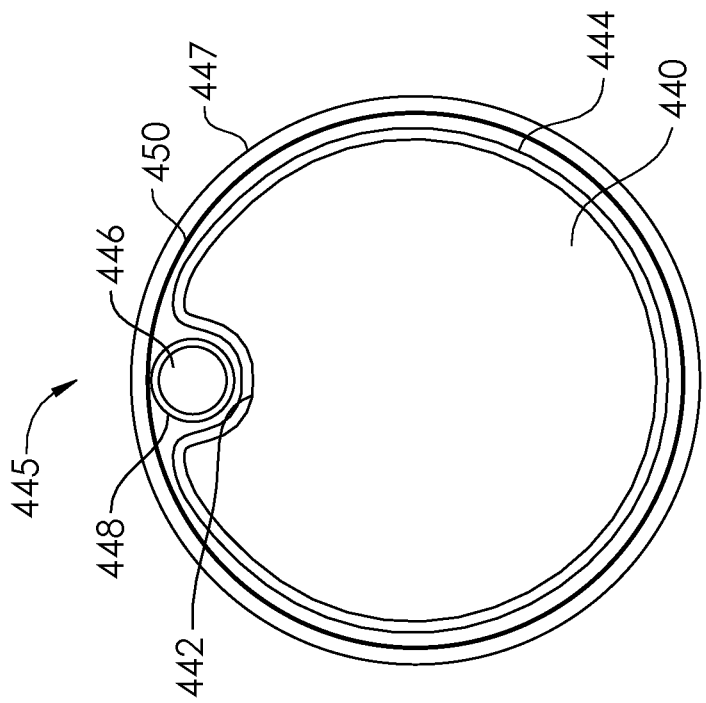
FIG. 38 is a cross-sectional view of the slotted mandrel of FIG. 37 as used in a dipping process according to an embodiment of the present invention.
Figure 37:
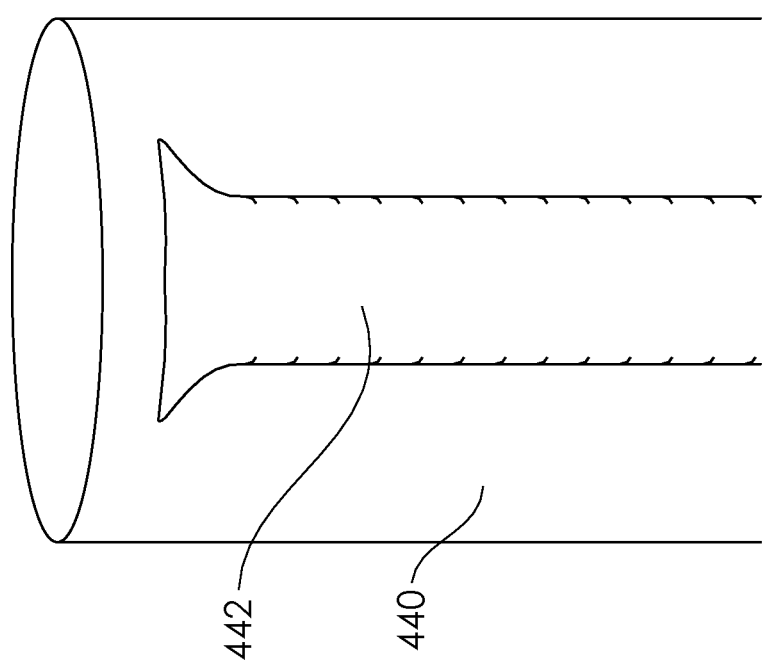
FIG. 37 is a perspective view of a slotted mandrel according to an embodiment of the present invention.

An assembly process for an embodiment of a thrombectomy catheter 306 is illustrated in FIGS. 37-42. A slotted mandrel 440 having a longitudinally extending slot 442 is shown in FIG. 37. FIG. 38 illustrates a cross-section of the slotted mandrel 440 and several components placed over it during a placement step, in the following radial order: liner tube 444, saline lumen tube 448 having a saline lumen 446, and a support layer 450. In some embodiments, the orifice may be pre-cut into the saline lumen tube 448 and may be aligned during the placement step. In some embodiments, the liner tube 444 may comprise PTFE or other fluropolymers. In some embodiments, the saline lumen tube 448 may comprise a polyimide tube. In some embodiments, the support layer 450 may comprise a tubular braid, one or more coils or a laser machined hypo tube. The slotted mandrel 440 with the components 444, 448, 450 placed over it, is dipped into a polyurethane, silicone, or other material to coat and set, during a dipping process, creating a composite structure 445 having an outer layer 447. The slotted mandrel 440 is then removed, during a removal step, and the ends of the saline lumen tube 448 may be cut clean. As seen in FIGS. 39-42, a radiopaque marker band 452 may be incorporated as part of the assembly by bonding the radiopaque marker band 452 to the saline lumen tube 448 with an adhesive 454 or epoxy, aligning the saline lumen tube 448 as in FIG. 42, and then completing the assembly and the dipping process as described in relation to FIG. 38.

Clog Detection/Clot Detection

Clogging of aspiration catheters, for example by large pieces of thrombus, is a common concern for users. Techniques to avoid clogging/choking of material within the catheter often involve rapidly, aggressively advancing the aspiration catheter or gently plucking at edges of a thrombus to insure only small pieces or portions are introduced at a time, pieces which are small enough to not clog or occlude the aspiration lumen. When a device becomes clogged during use, the potential for inadvertent dislodgment of thrombus downstream increases; this is referred to as distal embolism. As aspiration procedures of this type are often used in highly technical emergent settings, early clog detection of the aspiration catheter for the user during aspiration can contribute to the success of the procedure and clinical outcome. Some sources have reported that up to 50% of aspiration catheters used get clogged during use.

Additionally, the user may have difficulty determining whether there has been a loss of vacuum in the system, for example because of the syringe (or other vacuum source) being full of fluid or because of a leak in the system. Blood is relatively opaque and can coat the wall of the syringe, thus making it difficult to determine when the syringe becomes full. This makes it difficult to determine whether sufficient vacuum is being applied to the aspiration catheter. It is also difficult to determine whether there is an air leak in the system, which can be another cause for a loss of vacuum even before the syringe becomes full of the aspirated fluid.

During the aspiration of thrombus with an aspiration catheter, it is difficult to identify when thrombus is actively being aspirated, and when only blood is being aspirated. Typically it is desired to not aspirate sizable quantities of normal blood from blood vessels, because of the importance of maintaining normal blood volume and blood pressure. However, when tracking the tip of an aspiration catheter in proximity to a thrombus, it is difficult to know whether the aspiration catheter has actively engaged a thrombus, whether it has aspirated at least a portion of the thrombus, or whether it is not engaged with the thrombus, and is only aspirating blood. The use of aspiration catheters can therefore be inefficient, and cause more blood removal than desired, causing a user to minimize the length of the therapy and in severe cases necessitating blood transfusion. An increased volume of normal blood being aspirated also means that the vacuum source (e.g. syringe) will fill in a shorter amount of time, thus required more frequent replacement of the vacuum source. Distal embolism may occur if the vacuum pressure is not sufficient, and yet the user is not aware.

Figure 43:
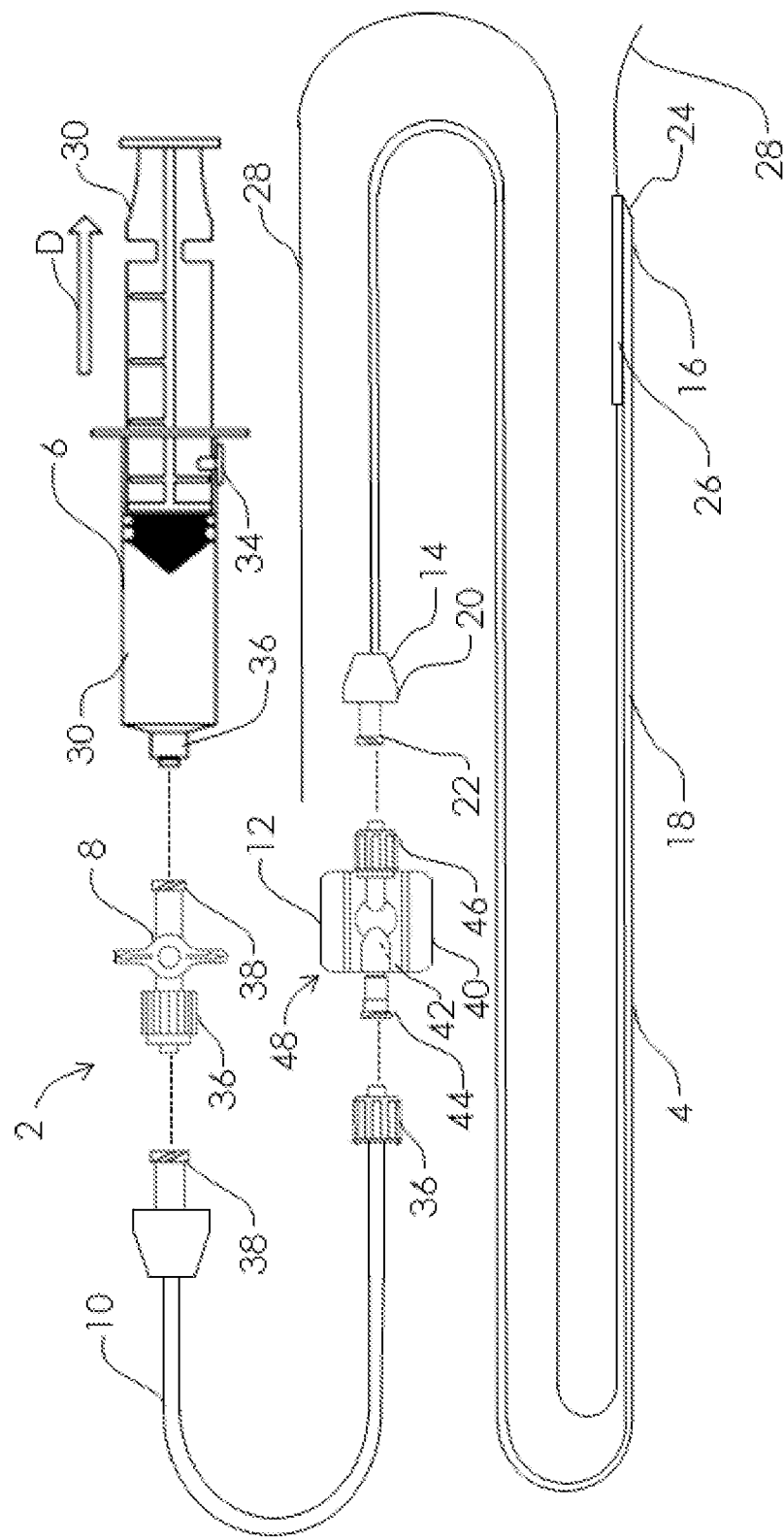
FIG. 43 is a plan view of a system for aspiration according to an embodiment.

An aspiration system 2 is illustrated in FIG. 43 and is configured to allow real time monitoring of catheter aspiration. The aspiration system 2 comprises an aspiration catheter 4, a vacuum source 6, a valve 8, extension tubing 10, and an aspiration monitoring system 48 including an in-line pressure transducer 12. The aspiration catheter 4 has a proximal end 14 and a distal end 16 and an aspiration lumen 18 extending from the proximal end 14 to the distal end 16. The aspiration lumen 18 may be sized for aspiration of thrombus, and in some embodiments may have an inner diameter of between about 0.038 cm (0.015 inches) and about 0.254 cm (0.100 inches). The aspiration catheter 4 includes a hub 20 at its proximal end which may include a female luer connector 22. The aspiration lumen 18 at the distal end 16 of the aspiration catheter 4 may include an angled orifice 24, which aids in the tracking through tortuous or occluded vasculature. In some embodiments, a guidewire lumen 26 is coupled to the distal end 16 of the aspiration catheter 4, and is configured to track over a guidewire 28. The vacuum source 6 may comprise a syringe, and may be sized between 5 ml and 100 ml, or between 20 ml and 60. The vacuum source 6 may comprise a VacLok® syringe, made by Merit Medical, Salt Lake City, Utah. The vacuum source 6 may include a barrel 30 and plunger 32, with a lock 34 which is configured to retain the plunger 32 in position in relation to the barrel 30, for example, when the plunger is pulled back in direction D to create a negative pressure (vacuum) inside the barrel 30. In some embodiments, the vacuum source 6 may comprise any other type of evacuatable reservoir, or may comprise a vacuum pump. The vacuum source 6 is connected to the aspiration lumen 18 of the aspiration catheter 4 via the extension tubing 10 and the valve 8. In some embodiments, the vacuum source 6 may be connected directly to the aspiration lumen 18 of the aspiration catheter 4. Male luer connectors 36 and female luer connectors 38 are indicated in FIG. 43. The valve 8 may be a standard two-way stopcock, as illustrated.

Figure 44A:
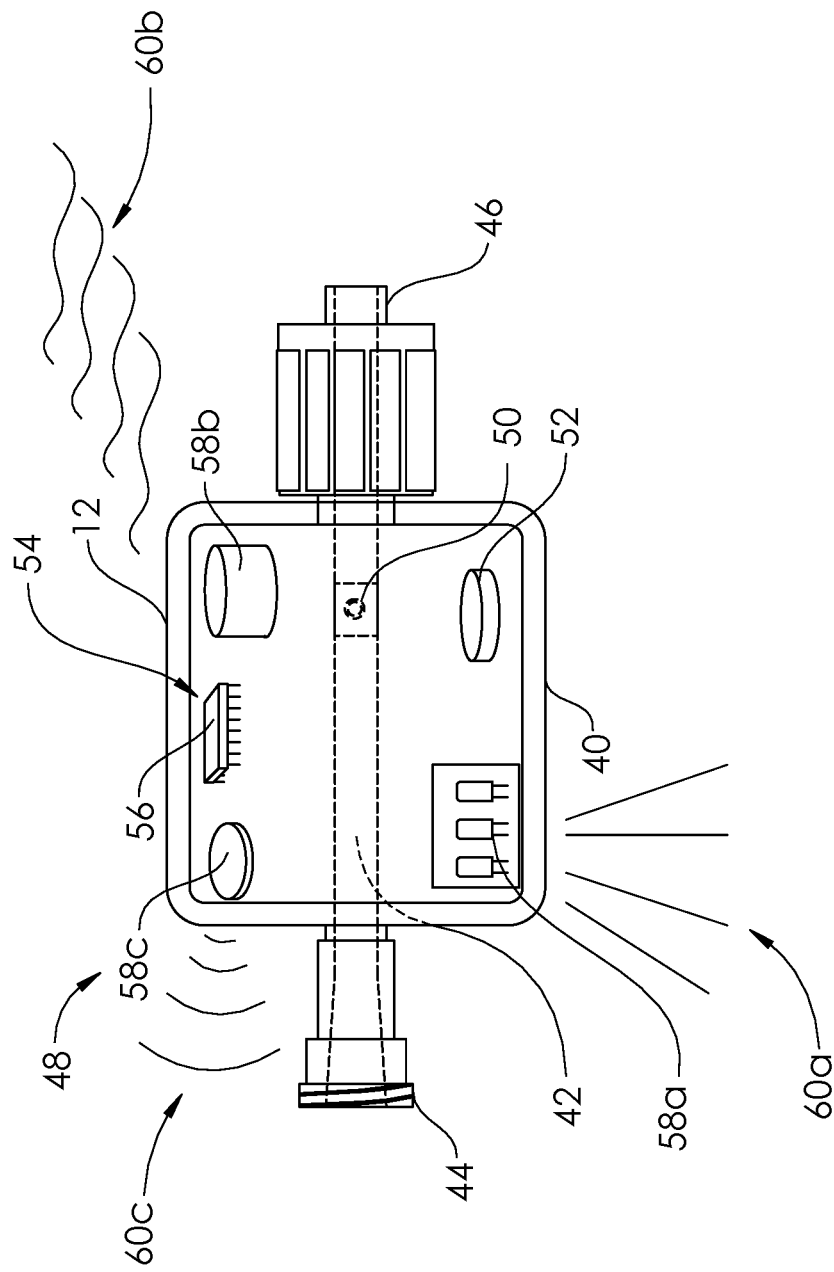
FIG. 44A is a detailed view of an aspiration monitoring system according to a first embodiment.

The pressure transducer 12 of the aspiration monitoring system 48 is configured to be fluidly coupled between the vacuum source 6 and the aspiration catheter 4. In FIG. 44A, the aspiration monitoring system 48 is illustrated as a self-contained device of a first embodiment. The pressure transducer 12 comprises a housing 40 having a cavity 42 extending between a first port 44 and a second port 46. In some embodiments, the first port 44 comprises a female luer and the second port 46 comprises a male luer. In some embodiments, the first port 44 comprises a female luer lock and the second port 46 comprises a male luer lock, each of which is attachable to and detachable from a corresponding luer lock of the opposite gender. The first port 44 is configured to be coupled to the vacuum source 6, either directly, or with the valve 8 and/or extension tubing 10 connected in between. The second port 46 is configured to be coupled to the aspiration lumen 18 of the aspiration catheter 4, for example, by coupling the second port 46 directly or indirectly to the hub 20 of the aspiration catheter 4. When the aspiration system 2 is used to aspirate body fluids and/or materials, for example blood and/or thrombus, the body fluids and/or materials are aspirated through the aspiration lumen 18 of the aspiration catheter from the angled orifice 24 at the distal end 16 to the female luer connector 22 at the proximal end 14, then pass through the second port 46 of the pressure transducer 12 first, through the cavity 42, and then through the first port 44. Depending on the amount of amount of vacuum (negative pressure) applied by the vacuum source 6, and the amount of flow resistance and resulting pressure drop along the aspiration system 2, the pressure within the cavity 42 will vary. For example, a more viscous fluid like blood, or a fluid having solid, semi-solid, or gel-like particles or portions, will cause more flow resistance through the relatively small aspiration lumen 18 of the aspiration catheter 4 than would water or normal saline solution. Thus the pressure within the cavity 42 of the pressure transducer 12 will decrease (the amount of vacuum will increase) as the flow resistance in the aspiration lumen 18 increases.

For definition purposes, when speaking of the amount of vacuum, a pressure of, for example, −15,000 pascal (−2.18 pounds per square inch, or psi) is a "larger vacuum" than −10,000 pascal (−1.45 psi). Additionally, −15,000 pascal is a "lower pressure" than −10,000 pascal. Furthermore, −15,000 pascal has a larger "absolute vacuum pressure" than does −10,000 pascal, because the absolute value of −15,000 is larger than the absolute value of −10,000. In FIG. 44A, a vacuum sensor 50 is disposed within the cavity 42 of the housing 40 and is in fluid communication with fluid that passes through the cavity 42. The vacuum sensor 50 may be a standard pressure sensor or transducer, including a pressure sensor designed primarily for measuring positive pressure. It may use any type of pressure sensing technology known in the art, including MEMS Technology. In some embodiments, the vacuum sensor 50 is configured for highest accuracy and/or precision within the range of pressures between about 0 pascal to about −101,325 pascal (−14.70 psi), or between about −45,000 pascal (−6.53 psi) and about −90,000 pascal (−13.05 psi), or between about −83,737 pascal (−12 psi) and about −96,527 pascal (−14 psi). In some embodiments, the power requirement for the vacuum sensor may range from 2.5 volts DC to 10 volts DC. In some embodiments, the vacuum sensor 50 may be an analog gauge with an output voltage. In the self-contained embodiment of the FIG. 44A, the vacuum sensor 50 is powered by one or more battery 52. Based on the power requirements of the vacuum sensor 50, and the power requirements of other components of the aspiration monitoring system 48 described herein, in some embodiments the one or more battery 52 may range between 1.5 volts and nine volts. Also contained within the housing is a measurement device 54, which in some embodiments may comprise a microprocessor. The measurement device 54 is coupled to the vacuum sensor 50 and receives signals from the vacuum sensor 50 indicative of real time measured pressure. In some embodiments, the measurement device 54 includes a memory module 56 in which information is stored that may be used by the measurement device 54, for example, in calculations.

One or more communication devices 58a, 58b, 58c are included within the aspiration monitoring system 48 and are coupled to the measurement device 54. Each of the one or more communication devices 58a-c are configured to generate a type of alert comprising an alert signal 60a-c, in response at least in part to activity and output of the measurement device 54. In some embodiments, the communication device 58a may include one or more LEDs (light emitting diodes) configured to generate a visible alert via a visible alert signal 60a, such as light that is continuously illuminated, or is illuminated in a blinking pattern. In some embodiments, lights other than LEDs may be used. In some embodiments, the communication device 58b may include one or more vibration generators configured to generate a tactile alert via a tactile alert signal 60b, which may include, but is not limited to, vibration or heat. In some embodiments, the vibration generator may comprise a piezoelectric device which is configured to vibrate when a voltage is applied. In some embodiments, the communication device 58c may include one or more sound generating devices configured to generate an audible alert via an audible alert signal 60c, such as a continuous noise, or a repeating noise. In some embodiments, the sound generating device may comprise a buzzer which is configured to sound one or more audible pitches when a voltage is applied. In some embodiments a piezoelectric device, such as that described in relation to the communication device 58b may also serve as a sound generating device, included as communication device 58c.

A user of an aspiration system 2 may desire to be notified of several conditions which may occur during use of the aspiration system 2. These potential conditions include, but are not limited to clogging, a loss of vacuum due to filling of the vacuum source 6 and or a breach, break or puncture in the aspiration system 2, and the engagement or aspiration of non-fluid, solid or semi-solid material such as thrombus. The aspiration monitoring system 48 of FIG. 44A is configured to alert users of an aspiration system 2 about real time status of the aspiration system 2, including operational conditions, which include: whether vacuum is being applied or not; flow conditions, which include whether a thrombus is engaged, whether a thrombus is being actively aspirated, whether the system is leaking air, whether the system is clogged, whether the vacuum source 6 is full and/or needs to be changed; or other potential set up issues. The real time feedback provided frees a user or operator from the need of excessive personal monitoring of the vacuum source 6, extension tubing 10, or other portions of the aspiration system 2, for improper or undesired flow or operation conditions, and thus allows the user to focus more attention on the patient being treated.

The pressure transducer 12 of the aspiration monitoring system 48 is configured to continuously measure and monitor the absolute pressure amplitude within the closed system of the aspiration system 2, and also is configured to measure and monitor the relative pressure over time to detect noteworthy flow changes within the flow circuit of the aspiration system 2. Some changes are discernible via absolute pressure measurement, while more subtle pressure deflections may be compared to a stored library in memory. Noteworthy conditions may be signaled to the user when appropriate. In some embodiments, the unfiltered signal may be amplified by an amplifier and filtered by a filter, for example, to increase the signal-to-noise ratio. Examples of the (background) noise 57 in an unfiltered signal can be seen in FIGS. 46A-46D (labeled in FIG. 46A). In some embodiments, one or more algorithms may be used, as described herein, to identify particular conditions of interest.

FIG. 44B illustrates a second embodiment of an aspiration monitoring system 62 having a pressure transducer 12 having a vacuum sensor 50 disposed within the cavity 42 of a housing 40. The vacuum sensor 50 may be powered by at least one battery 52. In some embodiments, the pressure transducer 12 may be reusable, and may be configured to allow charging of the battery 52, or of a capacitor (not shown) by direct charging methods, or by inductive power transfer methods and devices known in the art. Unlike the aspiration monitoring system 48 of FIG. 44A, the aspiration monitoring system 62 of FIG. 44B comprises a measurement device 64, memory module 66, and communication device 68 which are external to the pressure transducer 12. A power module 72, also external, may be used to power any of the measurement device 64, memory module 66, or communication device 68. The communication device 68 may be any of the communication device 58a, 58b, 58c described in relation to the aspiration monitoring system 48 of FIG. 44A, and are configured to product an alert via an alert signal 70. The communication device 68 may be portable so that it may be positioned close to the user.

Figure 44C:
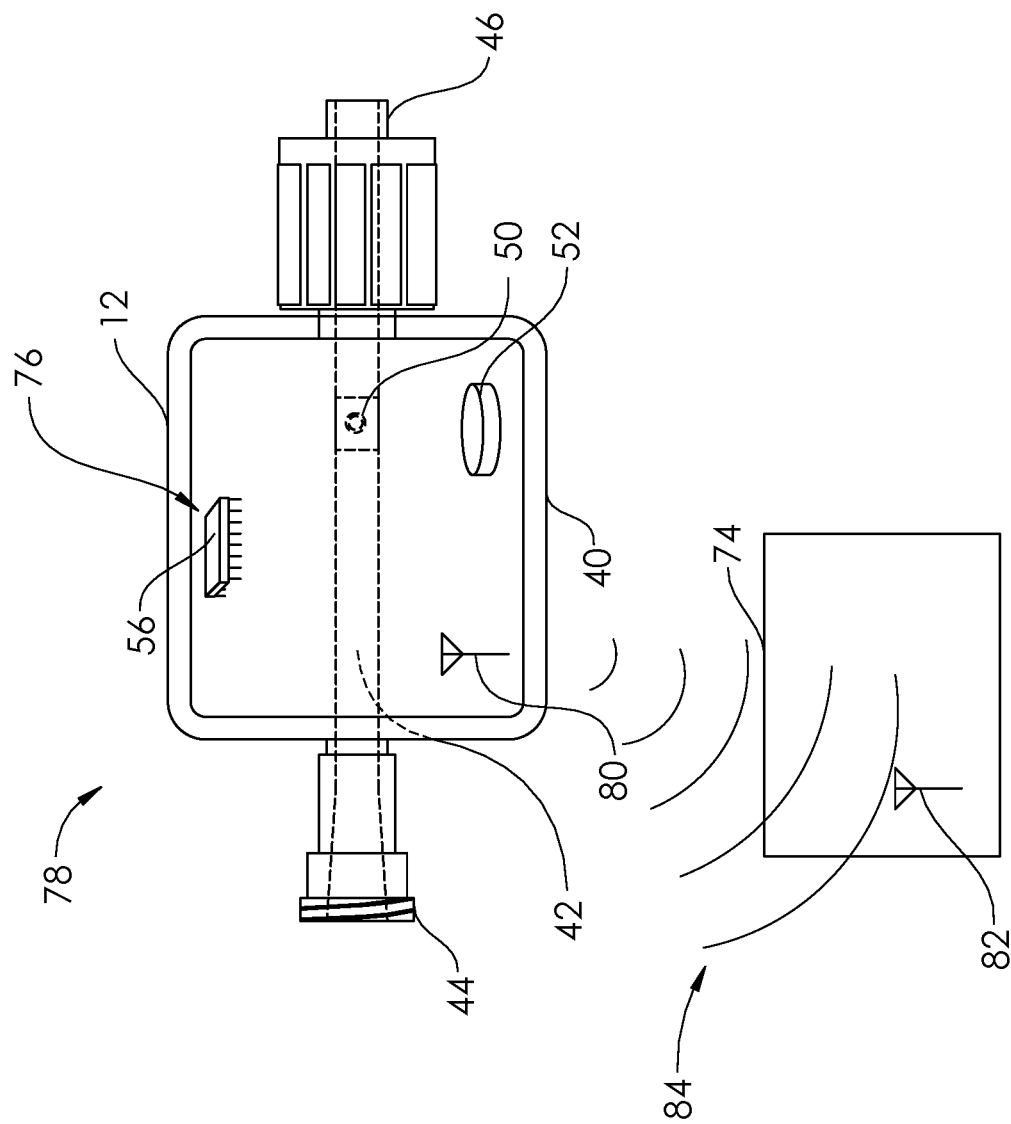
FIG. 44C is a view of an aspiration monitoring system according to a third embodiment.

In some embodiments, the communication device 68 may be wearable by the user. FIG. 44C illustrates an aspiration monitoring system 78 which includes an antenna 80 coupled to a measurement device 76. The measurement device 76 is similar to the measurement device 54 of prior embodiments, except that it wirelessly sends a communication signal 84 via the antenna 80 to a corresponding antenna 82 of a communication device 74. In some embodiments, the communication device 74 comprises a wristband which the user wears, and which may include a vibration generator or heat generator. In some embodiments, the communication device 74 comprises an audio speaker which may be attached to equipment or even to the patient or user. In some embodiments, the communication device 74 comprises an audio speaker on an earpiece or earbud that the user may wear. In some embodiments, Bluetooth® communication technology may be used.

Figure 45A:
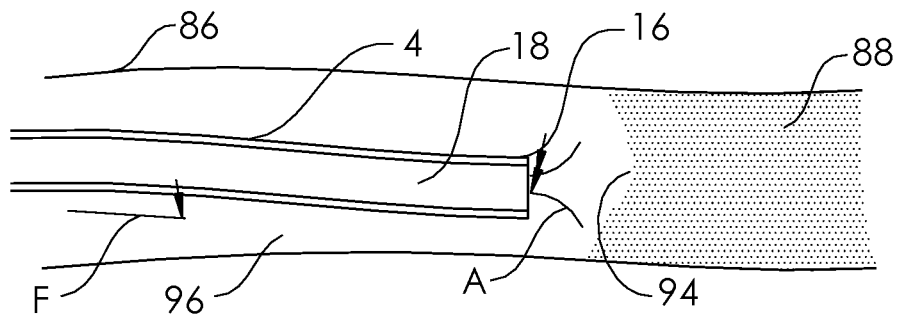
FIG. 45A is a sectional view of an aspiration catheter in a blood vessel prior to contact with a thrombus.
Figure 46A:
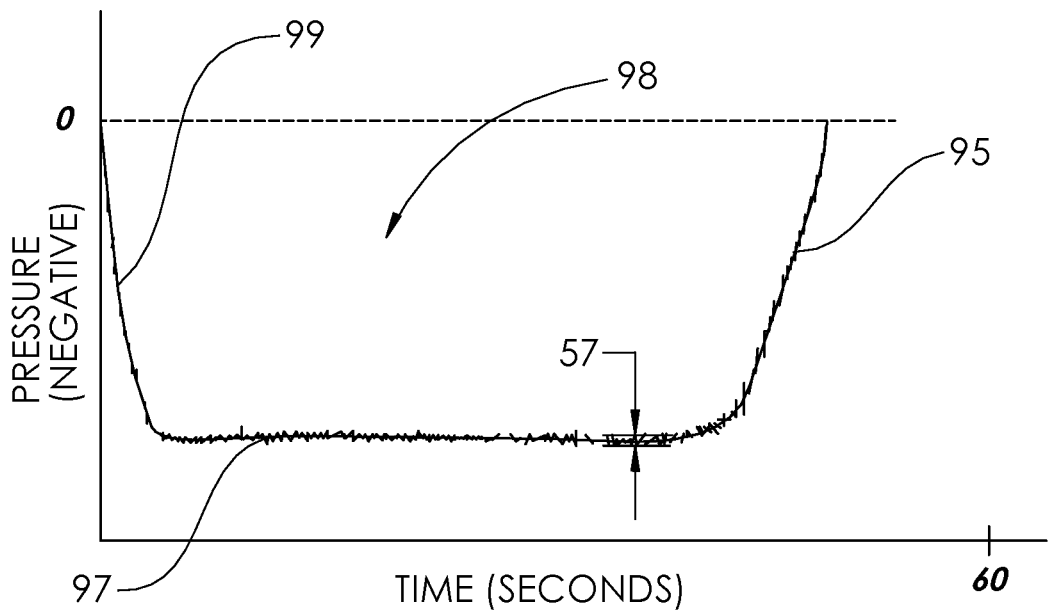
FIG. 46A is a graphic representation of pressure vs. time for the condition of FIG. 45A.

FIG. 45A illustrates the distal end 16 of an aspiration catheter 4 within a blood vessel 86 having at least one thrombus 88. The aspiration catheter 4 is being advanced in a forward direction F, but the distal end 16 of the aspiration catheter 4 has not yet reached the proximal extremity 94 of the thrombus 88. A vacuum source 6 (FIG. 43) has been coupled to the aspiration lumen 18 of the aspiration catheter 4 and activated (i.e. the valve 8 is open) causing blood 96 to be aspirated into the aspiration lumen 18 (arrows A). Turning to FIG. 46A, a corresponding curve 98 is represented for the normal fluid (e.g. blood) vacuum over time for the condition of FIG. 45A. The curve 98 represents vacuum pressure over time sensed by the vacuum sensor 50 of any of the embodiments presented. No leaks are present and no thrombus is being evacuated, and therefore the curve 98 includes a downward slope 99 when the vacuum source 6 increases the vacuum up (lowers the pressure) within the cavity 42 of the pressure transducer 12 to a relatively steady state. The steady pressure curve 97 continues while blood 96 is being aspirated. As the vacuum is decoupled from the aspiration lumen 18, for example by closing the valve 8 or by detaching any two of the ports (e.g. luers), or if the vacuum source 6 fills completely with blood 96, then an upward slope 95 is measured.

The measurement device 54, 64 is configured to compare the curve 97 with information stored in the memory module 56, 66 to identify this condition. In some embodiments, the measurement device 54, 64 uses an algorithm to make the comparison. In some embodiments, the measurement device 54, 64 then sends a signal to the communication device 58a-c, 74, and the communication device 58a-c, 74 generates an appropriate alert. Communication device 58a, for example a particular color LED, may be illuminated, or an LED may flash in a particular pattern or number of flashes. Communication device 58b may create a characteristic sound, or may generate an audio message in a number of languages. For example, the audio message may state, "Thrombus encountered," or "No thrombus encountered." Communication device 58c may vibrate or heat in a characteristic pattern, for example, a certain number of repetitions or a certain frequency between repetitions. The user may determine that an additional fluoroscopic image (e.g. angiography) or other imaging modalities may be necessary to better identify the location of the thrombus 88.

Figure 45B:
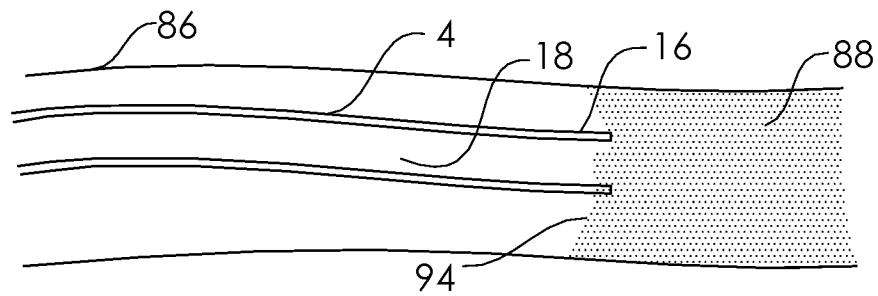
FIG. 45B is a sectional view of an aspiration catheter in a blood vessel upon contact with a thrombus.
Figure 46B:
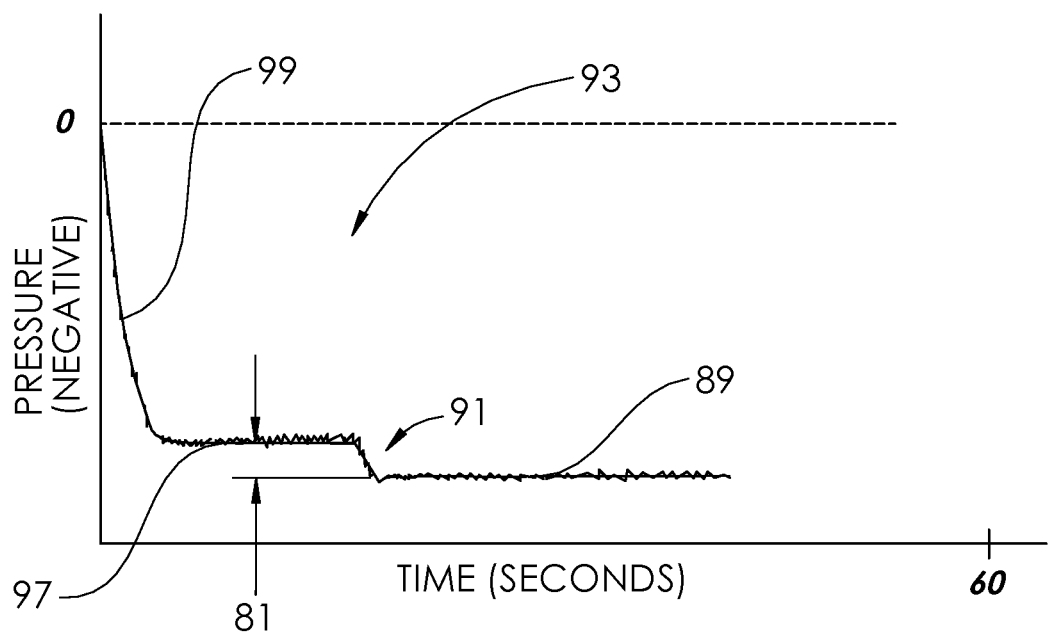
FIG. 46B is a graphic representation of pressure vs. time for the condition of FIG. 45B.
Figure 46C:
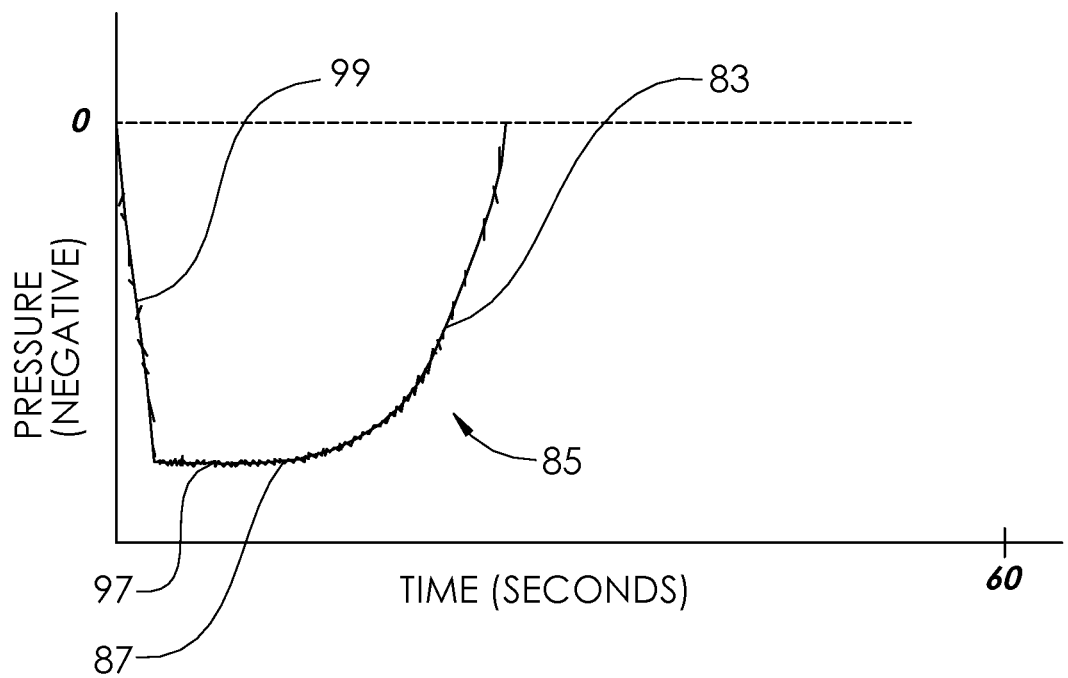
FIG. 46C is a graphic representation of pressure vs. time for the condition of FIG. 45C.

FIG. 45B illustrates the distal end 16 of an aspiration catheter 4 advanced to a position such that the distal end 16 of the aspiration catheter 4 contacts the proximal extremity 94 of the thrombus 88. The corresponding curve 93 in FIG. 46B represents vacuum pressure over time sensed by the vacuum sensor 50 of any of the embodiments presented. The curve 93 initially has a downward slope 99 followed by a steady pressure curve 97, as in the condition of FIG. 45A, graphed in FIG. 46A, however, when the distal end 16 of the aspiration catheter 4 contacts the proximal extremity 94 of the thrombus 88, if the aspiration causes a portion of the thrombus 88 (for example a large or relatively hard portion) to enter and become trapped in the aspiration lumen 18, then a clog condition occurs. A similar condition occurs if the distal end 16 of the aspiration catheter 4 is caught on the thrombus 88 by the vacuum, with virtually nothing flowing through the aspiration lumen 18. In either condition, the curve 93 includes a deviation (or disturbance) in fluid pressure 91. If the clog (or stuck condition) continues, then a flat, depressed pressure 89 is measured.

The measurement device 54, 64 is configured to compare the curve 93 with information stored in the memory module 56, 66 to identify this condition. In some embodiments, the measurement device 54, 64 uses an algorithm to make the comparison. In some embodiments, a pre-set pressure differential $\Delta P1$ may be stored in the memory module 56, 66 as a threshold, whereby the measurement of a pressure difference 81 less than this threshold does not result in the measurement device 54, 64 commanding the communication device 58a-c, 74 to send an alert signal 60a-c, 70. In some embodiments, when the pressure difference 81 is greater than (or greater than or equal to) the pre-set pressure differential ΔP1, the measurement device 54, 64 then sends a signal to the communication device 58a-c, 74, and the communication device 58a-c, 74 generates an appropriate alert. Communication device 58a, for example a particular color LED, may be illuminated, or an LED may flash in a particular pattern or number of flashes. Communication device 58b may create a characteristic sound, or may generate an audio message in a number of languages. For example, the audio message may state, "Clog Condition." Communication device 58c may vibrate or heat in a characteristic pattern, for example, a certain number of repetitions or a certain frequency between repetitions. When the user realizes that the clog condition is present, the user may pull on the aspiration catheter 4 and readvance it, in an attempt to contact a portion of the thrombus 88 that can be aspirated. If a portion of the thrombus is clogged in the aspiration lumen 18, and repositioning of the aspiration catheter 4 does not produce good results, the aspiration catheter 4 can be removed and the aspiration system 2 can be repurged, for example by a positive pressurization.

Figure 45C:
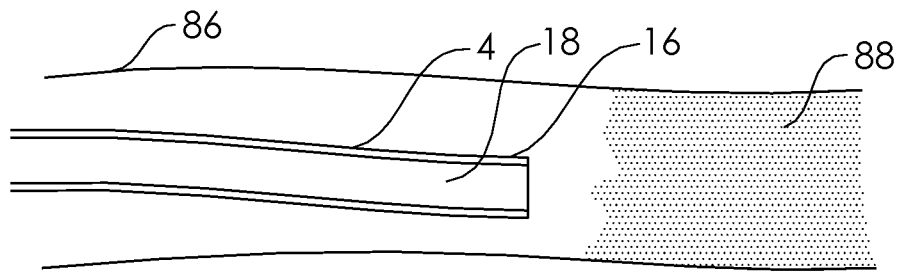
FIG. 45C is a sectional view of an aspiration catheter during a loss of vacuum.

FIG. 45C illustrates the distal end 16 of the aspiration catheter 4 in a general situation during which a breach in the aspiration system 2 has occurred. For example, a break, leak, puncture, pinhole, loosening, or disconnection may cause air to be pulled into the aspiration lumen 18 of the aspiration catheter 4, the cavity 42 of the pressure transducer 12, of the interior of the extension tubing 10, valve 8, or vacuum source 6. As graphed in the curve 85 of FIG. 46C, a downward slope 99 and a subsequent steady pressure curve 97 are measured, but at the point in time of the breach 87 an upward slope 83 begins.

The measurement device 54, 64 is configured to compare the curve 85 with information stored in the memory module 56, 66 to identify this condition. In some embodiments, the measurement device 54, 64 uses an algorithm to make the comparison. In some embodiments, the measurement device 54, 64 then sends a signal to the communication device 58a-c, 74, and the communication device 58a-c, 74 generates an appropriate alert. Communication device 58a, for example a particular color LED, may be illuminated, or an LED may flash in a particular pattern or number of flashes. Communication device 58b may create a characteristic sound, or may generate an audio message in a number of languages. For example, the audio message may state, "System Leak." Communication device 58c may vibrate or heat in a characteristic pattern, for example, a certain number of repetitions or a certain frequency between repetitions. Upon receiving the alert, the user will check the components of the aspiration system 2 and either fix the breach or replace one or more of the components of the aspiration system 2. For example, in some cases, the communication device 58a-c, 74 may alert the user when the measurement device 54, 64 confirms a loss of vacuum, allowing the user to change or recharge the vacuum source 6, which has become depleted (e.g. by filling with blood and/or thrombus).

Figure 45D:
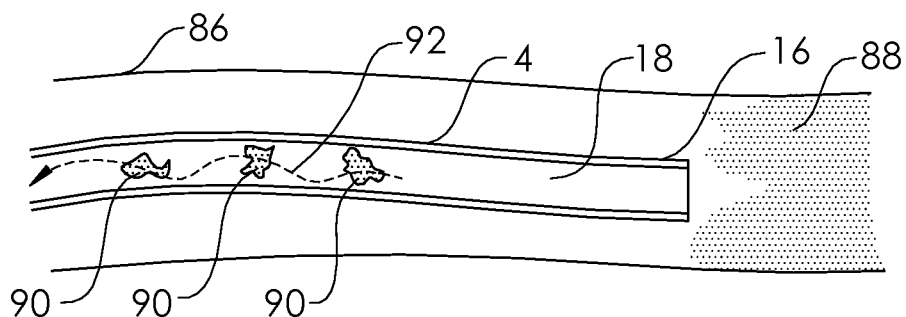
FIG. 45D is a sectional view of thrombi being aspirated through an aspiration catheter.

FIG. 45D illustrates the distal end 16 of the aspiration catheter 4 during the successful aspiration of pieces or portions 90 of the thrombus 88. In some cases, the pieces or portions 90 may follow a tortuous path 92, due to disturbances or collisions with the inner wall of the aspiration lumen 18 while being pulled through the aspiration lumen 18. In some cases, the pieces or portions 90 may catch and slip within the inner wall of the aspiration lumen 18, for example, do to variance of the inner diameter of the aspiration lumen 18 along the length. Either of these situations can cause a corresponding series of increases and decreases in the pressure being sensed by the pressure transducer 12, while the pieces or portions 90 are traveling through the aspiration lumen 18. As graphed in the curve 79 of FIG. 46D, a downward slope 99 and a subsequent steady pressure curve 97 are measured, but as the pieces or portions 90 of thrombus 88 travel down the aspiration lumen 18 of the aspiration catheter 4, a deviation 77 of fluid pressure comprising a plurality of decreases and increases in pressure (increases and decreases in vacuum pressure) is measured. As the pieces or portions 90 of thrombus 88 exit the proximal end of the aspiration lumen 18 of the aspiration catheter 4, a second steady pressure curve 75 is measured. The duration 67 of the deviation 77 is the amount of transit of the particular significant pieces or portions 90 of thrombus 88. The duration 67 can range quite a bit, but in some cases may be less than a second or up to about 30 seconds. When again additional pieces or portions 90 of thrombus 88 are aspirated into and travel down the aspiration lumen 18 of the aspiration catheter 4, another deviation 73 of fluid pressure comprising a plurality of decreases and increases in pressure (increases and decreases in vacuum pressure) is measured. At the end of the curve 79, the vacuum source 6 is shown filling completely with blood 96 and the pieces or portions 90 of thrombus 88, and so an upward slope 95 is measured.

The measurement device 54, 64 is configured to compare the curve 79 with information stored in the memory module 56, 66 to identify when the pieces or portions 90 of thrombus 88 are actively being aspirated, as in deviation 77 and deviation 73, and when the pieces or portions of thrombus 88 are not being actively, or substantially, aspirated, as in steady pressure curve 97, the steady pressure curve 75, and the steady pressure curve 71. In some embodiments, the measurement device 54, 64 uses an algorithm to make the comparison. In some embodiments, a pre-set pressure differential ΔP2 may be stored in the memory module 56, 66 as a threshold, whereby the measurement of a pressure difference 69 less than this threshold does not result in the measurement device 54, 64 commanding the communication device 58a-c, 74 to send a first type of alert via an alert signal 60a-c, 70. In some embodiments, when the pressure difference 69 is greater than (or greater than or equal to) the pre-set pressure differential ΔP2, the measurement device 54, 64 then sends a signal to the communication device 58a-c, 74, and the communication device 58a-c, 74 generates an appropriate alert. Communication device 58a, for example a particular color LED, may be illuminated, or an LED may flash in a particular pattern or number of flashes. In some embodiments, the communication device 58a may comprise a light whose intensity increases proportionally with the pressure. Communication device 58b may create a characteristic sound, or may generate an audio message in a number of languages. For example, the audio message may state, "Thrombus being aspirated." In some embodiments, communication device 58b may comprise one or more noises or beeps. In some embodiments, the communication device 58b may comprise a particular series of beeps corresponding to each different condition. For example, three short beeps may correspond to no thrombus being aspirated, while five long, loud beeps may correspond to a system leak. In some embodiments, a plurality of different tones (pitches) may be used to alert a user about different conditions. As an example, a low pitch sound may be used for a first condition (e.g. no thrombus being aspirated) and a second, higher pitch sound may be used for a second condition (e.g. a system leak). In some embodiments, a plurality of different tones may be used to alert a user about a first condition and a second plurality (e.g. in a different combination, or with additional tones) may be used to alert a user about a second condition. Communication device 58c may vibrate or heat in a characteristic pattern, for example, a certain number of repetitions or a certain frequency between repetitions. When the user realizes that the thrombus is being aspirated, the user may choose to advance (or retract) the aspiration catheter 4, for example with fluoroscopic visualization, along the length of the thrombus 88, in an attempt to continue the aspiration of the thrombus 88. In some cases, the user may choose to stop the advancement or retraction of the aspiration catheter 4 at a certain amount of time after the alert is generated, in order to allow the pieces or portions 90 of thrombus 88 to completely exit the aspiration lumen 18. When the measurement device 54, 64 identifies a subsequent steady pressure curve 75, 71 that follows a deviation 77, 73, the measurement device 54, 64 in some embodiments sends a signal that causes the communication device 58a-c, 74 to generate a second type of alert via an alert signal 60a-c, 70. For example, in some embodiments, communication device 58b may send an audio message that states, "Thrombus no longer being aspirated." When the user realizes that the thrombus is no longer being aspirated, the user may advance or retract the aspiration catheter, in an attempt to contact another portion of the thrombus 88 that can be aspirated. In some embodiments, the deviation 77 may be positively identified as a true deviation indicating thrombus being actively aspirated, pressure difference 69 is between about 700 pascal and about 1700 pascal. In some embodiments, the deviation 77 may be positively identified as a true deviation indicating thrombus being actively aspirated, pressure difference 69 is between about 1000 pascal and about 1300 pascal. In some embodiments, the deviation 77 may be positively identified as a true deviation indicating thrombus being actively aspirated, pressure difference 69 is about 1138 pascal. The pressure difference 69 may be measured by determining a baseline pressure 63 and a peak pressure 61 and determining the absolute value difference. For example:

Absolute value difference (AVD)=|(−89,631 pascal)− (−90,769 pascal)|=1138 pascal Or for example:

Absolute value difference (AVD)=|(−43,710 pascal)− (−45,102 pascal)|=1281 pascal The pressure difference 81 (FIG. 46B) may also represent a deviation that may be identified in a similar manner, after which the communication device 58a-c, 74 generates an appropriate alert, such as, "Clog condition."

Figure 46D:
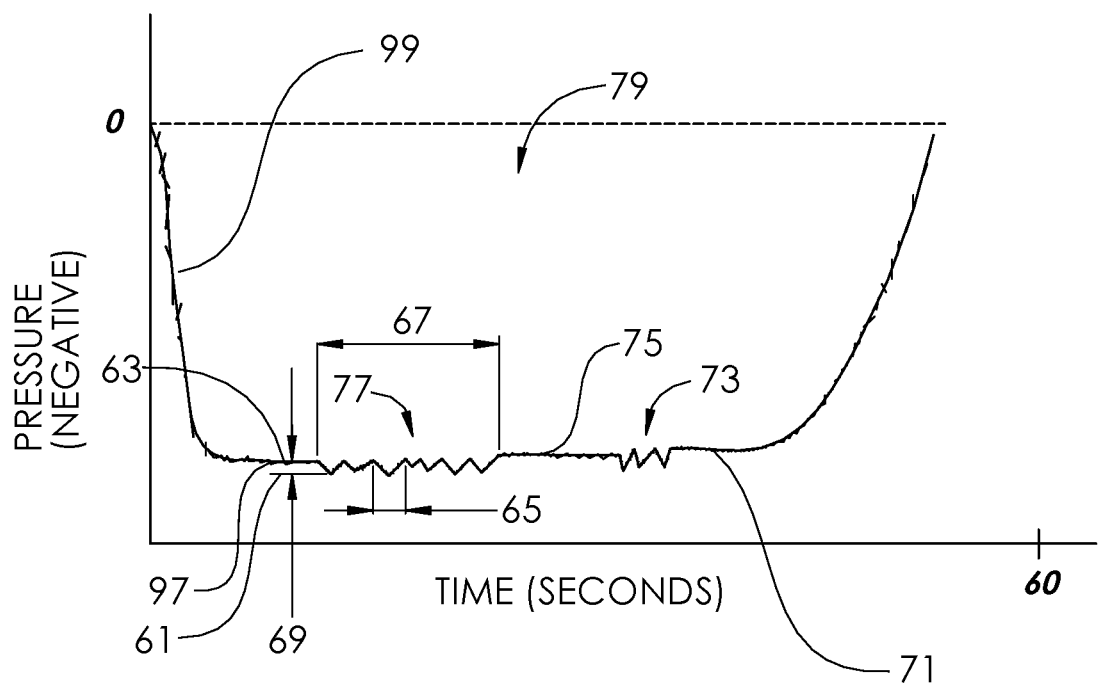
FIG. 46D is a graphic representation of pressure vs. time for the condition of FIG. 45D.

Because vacuum pressure is a negative pressure, the peak pressure 61, as shown in FIG. 46D, is actually a lower number than the baseline pressure 63. In some embodiments, the measurement device 54, 64 may also be configured to make a comparison, for example by using an algorithm, between a stored differential time t1 and a duration 65 of a single one of the plurality of decreases and increases in pressure in the deviation 77. For example, in some embodiments, the deviation may be positively identified as a true deviation indicating thrombus being actively aspirated, if the duration is between about 0.001 seconds and about 0.50 seconds. In some embodiments, the deviation may be positively identified as a true deviation indicating thrombus being actively aspirated, if the duration is between about 0.005 seconds and about 0.10 seconds. In some embodiments, the deviation may be positively identified as a true deviation indicating thrombus being actively aspirated if the duration is between about 0.05 seconds and about 0.20 seconds. In some embodiments, the measurement device 54, 64 is configured to recognize deviation 77 after two or more decreases and increases in pressure are measured. In some embodiments, the measurement device 54, 64 is configured to recognize deviation 77 after five or more decreases and increases in pressure are measured. In some embodiments, the measurement device 54, 64 is configured to recognize deviation 77 after ten or more decreases and increases in pressure are measured.

Insertion of the pressure transducer 12 in line in either the embodiment of FIG. 44A or the embodiment of FIG. 44B does not measurably change performance characteristics of the aspiration system 2, because the cavity 42 is relatively short and has a relatively large inner diameter, and thus is not a significant source of fluid flow resistance. In some embodiments, the inner diameter may be between about 2.2 mm (0.086 inches) and about 3.2 mm (0.125 inches). In some embodiments, the measurement device 54, 64, 76 need not include a microprocessor, as pre-defined set points (e.g. for certain thresholds) may be included in firmware, microcontroller, or other locations. In some embodiments, including but not limited to the embodiment of FIG. 44B, the pressure transducer 12 may be an off-the-shelf blood pressure monitor system, which is modified or augmented with other components. In some embodiments an off-the-shelf blood pressure monitor system may be used as the output of the aspiration monitoring system 48, 62, 78. In some embodiments, an aspiration catheter 4 may have a pressure transducer in the distal end 16. This pressure transducer may be used as the pressure transducer 12 of the aspiration monitoring system 48, 62, 78. In some embodiments, a pressure sensor may be located within a Tuohy-Borst valve, and introducer sheath, a guiding catheter, or another component of the system through which is in fluid communication with the aspiration lumen 18. In some embodiments, the pressure sensor may be located anywhere within the aspiration lumen of the aspiration catheter.

In some embodiments, instead of an LED, the visual alert is provided by a communication device 58a comprising a display which displays visual messages of text in a particular language, for example, "Thrombus encountered," "No thrombus encountered," "Clog condition," "System leak," "Loss of vacuum," "Thrombus being aspirated," or "Thrombus no longer being aspirated." The visual messages may be combined with any of the other alert signals 60a-c, 70 described herein. The aspiration monitoring system 48, 62, 78 described herein give real time awareness to users performing aspiration procedures, such as the removal of thrombus via an aspiration system 2. One skilled in the art will recognize that by knowing the real time condition of the aspiration system 2, the user is able to immediately make changes to the procedure in order to optimize results, increase safety for the patient and/or medical personnel, reduce costs (e.g. number of vacuum sources 6 required), and reduce procedure time (also a cost benefit). Because the user is typically performing multiple tasks during an aspiration procedure, the sensory aid provided by the aspiration monitoring system 48, 62, 78 allows the user to focus on these tasks without having to continually attempt to monitor conditions which are often difficult to visually monitor. The user may also modify and control the aspiration monitoring system 48, 62, 78 via an input 59 (FIG. 44B), which may comprise a data entry module, keyboard, or a series of buttons with a display. The input 59 may in some embodiments comprise an auditory input which accepts voice commands. Alternatively, the user may input information and control the aspiration monitoring system, 48, 62, 78 remotely. Some of the alerts which the user may select or deselect in the aspiration monitoring system 48, 62, 78 include, but are not limited to: whether the aspiration system 2 is potentially blocked or clogged, or is flowing normally; whether thrombus has been contacted or not; whether a clog has occurred; whether the vacuum source 6 is adequate, or whether it has been depleted and requires replacement; whether there is a leak in the aspiration system 2; whether setup or connection of the components of the aspiration system 2 was done correctly or incorrectly; whether to advance the catheter distally; whether to retract the catheter; whether to continue moving the catheter at the same speed; whether to increase or decrease the speed of catheter advancement; whether thrombus is actively being aspirated; and whether thrombus stops being actively aspirated.

In some embodiments, alternate power sources may be used, for example, standard AC power with or without an AC/DC convertor; direct connection to existing equipment (e.g. vacuum pumps, etc.); solar power. The aspiration monitoring system 48, 62, 78 may be packaged sterile or may be resterilizable by techniques known by those skilled in the art. In some embodiments, flow or volume gauges may be used in conjunction with or instead of the pressure gauge 12, in order to determine, for example, a clog, or a change in the amount of vacuum.

Though aspiration of thrombus has been described in detail, the aspiration monitoring system 48, 62, 78 has utility in any aspiration application wherein heterogeneous media is being aspirated. This may include the aspiration of emboli (including not thrombotic emboli) from ducts, vessels, or cavities of the body, or even from solid or semi-solid portions of the body, including, but not limited to, portions of fat, breasts, and cancerous tissue.

In some embodiments, the aspiration system 2 is be provided to the user as a kit with all or several of the components described, while in other embodiments, only the aspiration monitoring system 48 is provided. Though discussion herein includes embodiments for aspiration of thrombus and blood, the definition of the word "fluid" should be understood throughout to comprise liquids and gases.

In some embodiments, an additional or alternate sensor may be used to monitor flow conditions for the notification of the user, including, but not limited to: a Doppler sensor, an infrared sensor, or a laser flow detection device. In some embodiments, an externally-attached Doppler sensor may be employed. In some embodiments, an infrared sensor or a laser flow detection device may be employed around the extension tubing 10.

Assisted Aspiration

Figure 47:
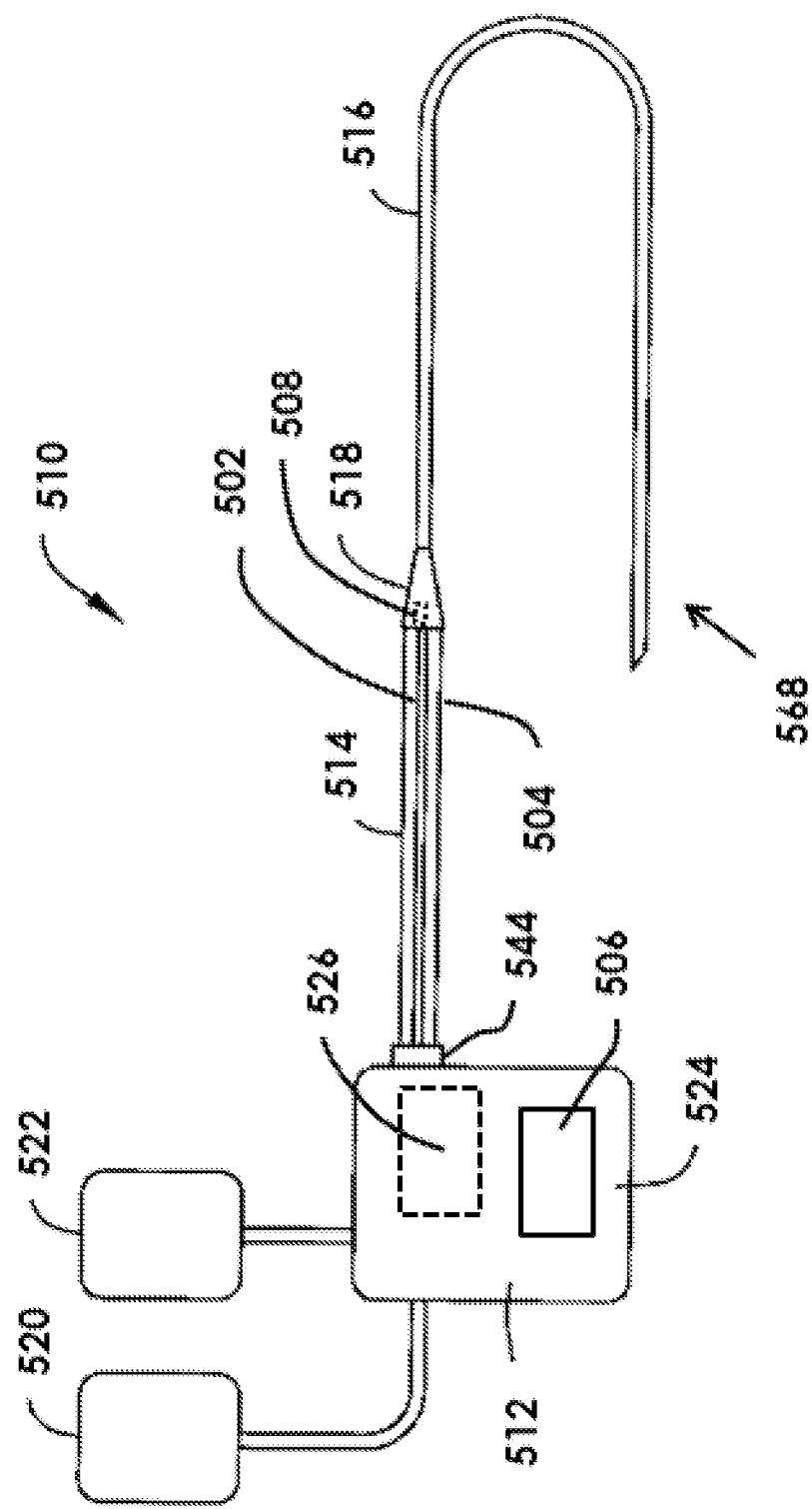
FIG. 47 is a diagrammatic view of a system for aspirating thrombus according to an embodiment of the present invention.

FIG. 47 is a diagrammatic figure depicting an assisted aspiration system 510. The aspiration system 510 includes a remote hand piece 512 that contains a fluid pump 526 and an operator control interface 506. In one contemplated embodiment, the system 510 is a single use disposable unit. The aspiration system 510 may also include extension tubing 514, which contains a fluid irrigation lumen 502 and an aspiration lumen 504, and which allows independent manipulation of a catheter 516 without requiring repositioning of the hand piece 512 during a procedure performed with the aspiration system 510. Extension tubing 514 may also act as a pressure accumulator. High pressure fluid flow from the pump 526, which may comprise a displacement pump, pulses with each stroke of the pump 526 creating a sinusoidal pressure map with distinct variations between the peaks and valleys of each sine wave. Extension tubing 514 may be matched to the pump 526 to expand and contract in unison with each pump pulse to reduce the variation in pressure caused by the pump pulses to produce a smooth or smoother fluid flow at tip of catheter 516. Any tubing having suitable compliance characteristics may be used. The extension tubing 514 may be permanently attached to the pump 526 or it may be attached to the pump 526 by a connector 544. The connector 544 is preferably configured to ensure that the extension tubing 514 cannot be attached to the pump 526 incorrectly.

Figure 49:
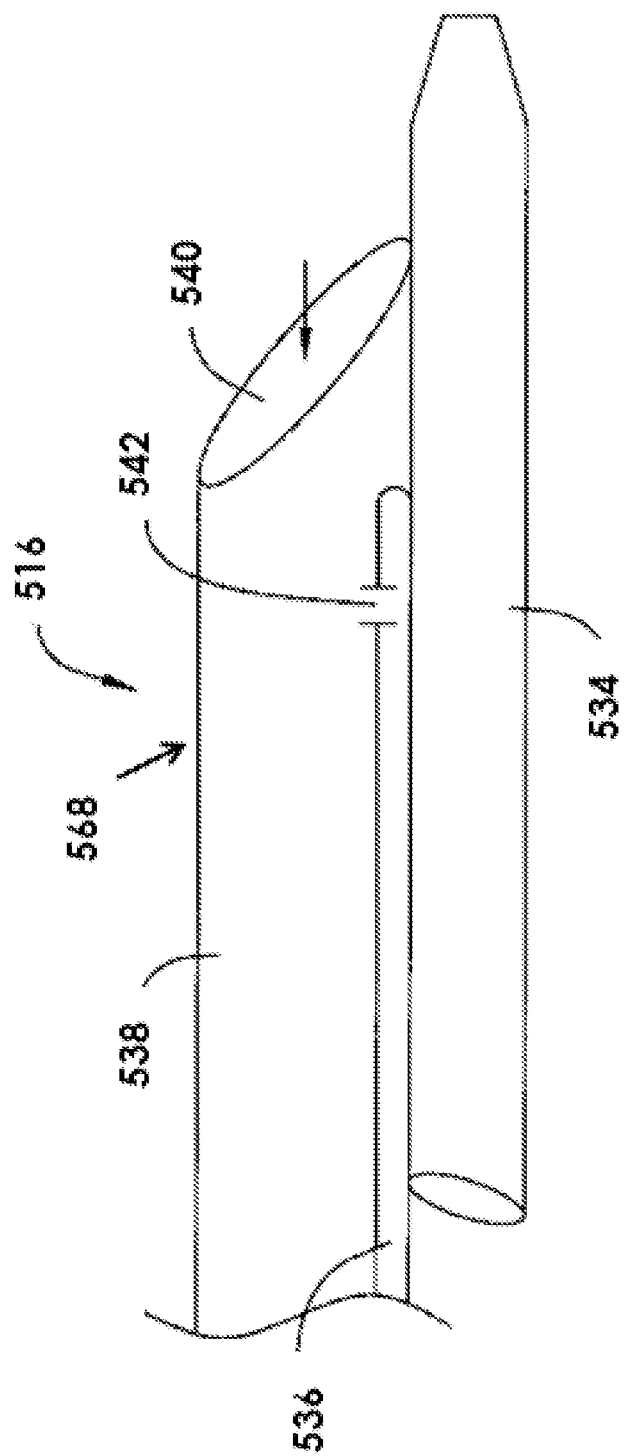
FIG. 49 is a diagrammatic view of the distal end portion of the system for aspirating thrombus of FIG. 47.

An interface connector 518 joins the extension tubing 514 and the catheter 516 together. In one contemplated embodiment, the interface connector 518 may contain a filter assembly 508 between high pressure fluid injection lumen 502 of the extension tubing 514 and a high pressure injection lumen 536 of the catheter 516 (FIG. 49). The catheter 516 and the extension tubing 514 may be permanently joined by the interface connector 518. Alternatively, the interface connector 518 may contain a standardized connection so that a selected catheter 516 may be attached to the extension tubing 514. In some embodiments, the filter assembly 508 may be removably coupled to the extension tubing 514 by a quick disconnect connection.

Attached to the hand piece 512 are a fluid source 520 and a vacuum source 522. A standard hospital saline bag may be used as fluid source 520; such bags are readily available to the physician and provide the necessary volume to perform the procedure. Vacuum bottles may provide the vacuum source 522 or the vacuum source 522 may be provided by a syringe, a vacuum pump or other suitable vacuum source. The filter assembly 508 serves to filter particulate from the fluid source 520 to avoid clogging of the high pressure injection lumen 536 and an orifice 542 (FIG. 49). As described herein, distal sections of the high pressure injection lumen 536 may be configured with small inner diameters, and to the filter assembly 508 serves to protect their continuing function. By incorporating one of a variety of catheters 516 into the assisted aspiration system 510, for example with varying lumen configurations (inner diameter, length, etc.), a variety of aspiration qualities (aspiration rate, jet velocity, jet pressure) may be applied in one or more patients. These aspiration qualities can be further achieved by adjustment of the pump 526, to modify pump characteristics (flow rate, pump pressure). In some embodiments, the catheter 516 may be used manually, for example, without the pump 526, and controlled by hand injection. The manual use of the catheter 516 may be appropriate for certain patient conditions, and may serve to reduce the cost of the procedure.

In one contemplated embodiment, the catheter 516 has a variable stiffness ranging from stiffer at the proximal end to more flexible at the distal end. The variation in the stiffness of the catheter 516 may be achieved with a single tube with no radial bonds between two adjacent tubing pieces. For example, the shaft of the catheter 516 may be made from a single length of metal tube that has a spiral cut down the length of the tube to provide shaft flexibility. Variable stiffness may be created by varying the pitch of the spiral cut through different lengths of the metal tube. For example, the pitch of the spiral cut may be greater (where the turns of the spiral cut are closer together) at the distal end of the device to provide greater flexibility. Conversely, the pitch of the spiral cut at the proximal end may be lower (where the turns of the spiral cut are further apart) to provide increased stiffness. A single jacket covers the length of the metal tube to provide for a vacuum tight catheter shaft. Other features of catheter 516 are described with reference to FIG. 49, below.

Figure 48:
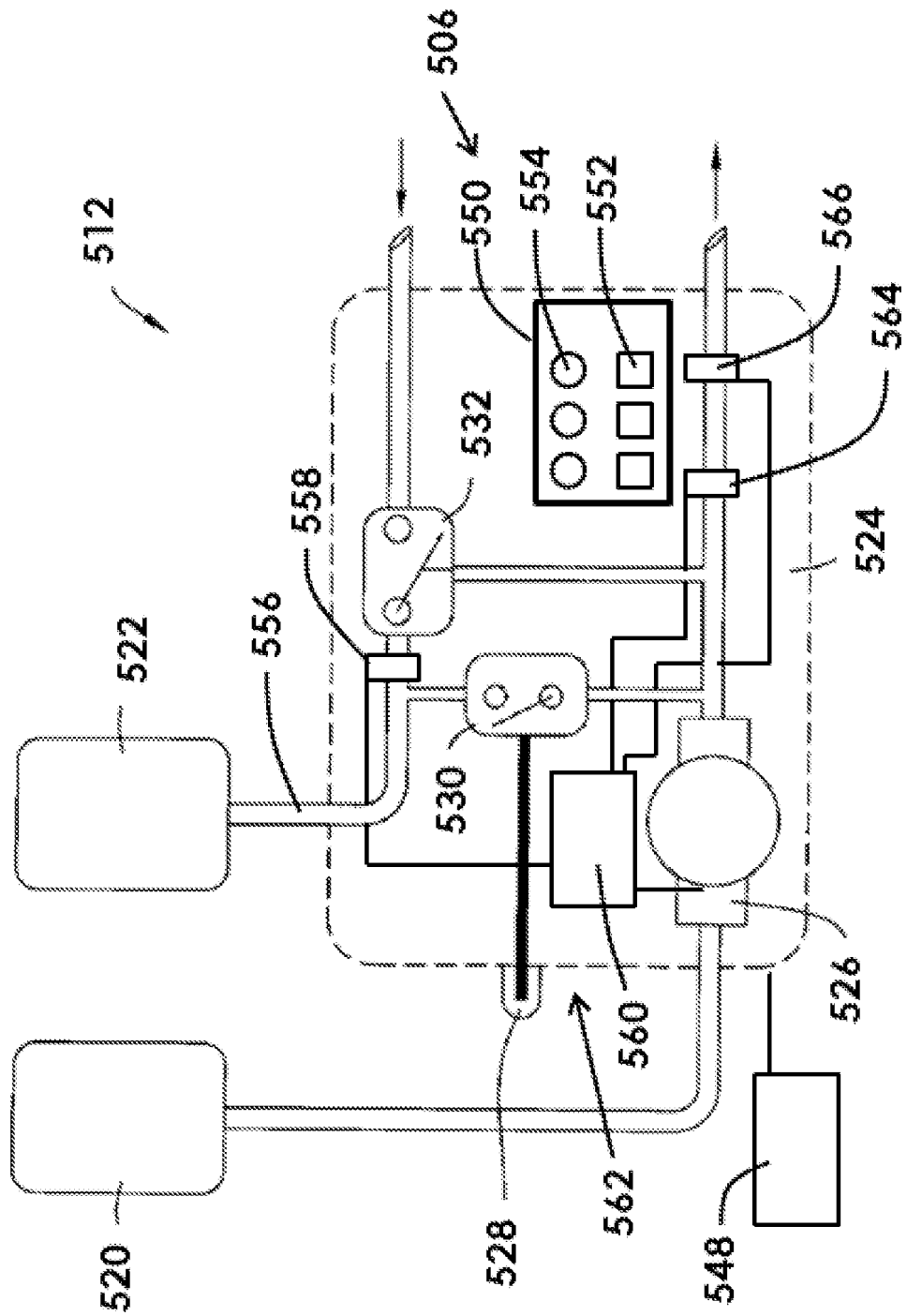
FIG. 48 is a diagrammatic view showing more detail of the proximal portion of the system for aspirating thrombus of FIG. 47.

FIG. 48 is a diagrammatic view showing more detail of the hand piece 512 and the proximal portion of assisted catheter aspiration system 510. The hand piece 512 includes a control box 524 where the power and control systems are disposed. The pump 526 may be a motor driven displacement pump that has a constant output. This pump displacement to catheter volume, along with the location of the orifice 542 (exit) of the catheter high pressure lumen 536 within the aspiration lumen 538 (FIG. 49), ensures that no energy is transferred to the patient from the saline pump as all pressurized fluid is evacuated by the aspiration lumen. A prime button 528 is mechanically connected to a prime valve 530. When preparing the device for use, it is advantageous to evacuate all air from the pressurized fluid system to reduce the possibility of air embolization. By depressing the prime button 528, the user connects the fluid source 520 to the vacuum source 522 via the pump 526. This forcefully pulls fluid (for example 0.9% NaCl solution, or "saline", no "normal saline", or heparinized saline) through the entire pump system, removing all air and positively priming the system for safe operation. A pressure/vacuum valve 532 is used to turn the vacuum on and off synchronously with the fluid pressure system. One contemplated valve 532 is a ported one way valve. Such a valve is advantageous with respect to manual or electronic valve systems because it acts as a tamper proof safety feature by mechanically and automatically combining the operations of the two primary systems. By having pressure/vacuum valve 532, the possibility of turning the vacuum on without activating the fluid system is eliminated.

The operator control interface 506 is powered by a power system 548 (such as a battery or an electrical line), and may comprise an electronic control board 550, which may be operated by a user by use of one or more switches 552 and one or more indicator lamps 554. The control board 550 also monitors and controls several device safety functions, which include over pressure and air bubble detection and vacuum charge. A pressure sensor 564 monitors pressure, and senses the presence of air bubbles. Alternatively, an optical device 566 may be used to sense air bubbles. In one contemplated embodiment, the pump pressure is proportional to the electric current needed to produce that pressure. Consequently, if the electric current required by pump 526 exceeds a preset limit, the control board will disable the pump by cutting power to it. Air bubble detection may also be monitored by monitoring the electrical current required to drive the pump at any particular moment. In order for a displacement pump 526 to reach high fluid pressures, there should be little or no air (which is highly compressible) present in the pump 526 or connecting system (including the catheter 516 and the extension tubing 514). The fluid volume is small enough that any air in the system will result in no pressure being generated at the pump head. The control board monitors the pump current for any abrupt downward change that may indicate that air has entered the system. If the rate of drop is faster than a preset limit, the control board will disable the pump by cutting power to it until the problem is corrected. Likewise, a block in the high pressure lumen 536, which may be due to the entry of organized or fibrous thrombus, or a solid embolus, may be detected by monitoring the electrical current running the pump 526. In normal use, the current fluxuations of the pump 526 are relatively high. For example, the pump may be configured so that there is a variation of 200 milliAmps or greater in the current during normal operation, so that when current fluxuations drop below 200 milliAmps, air is identified, and the system shuts down. Alternatively, current fluxuations in the range of, for example, 50 milliAmps to 75 milliAmps may be used to identify that air is in the system. Additionally, an increase in the current or current fluxuations may indicate the presence of clot or thrombus within the high pressure lumen 536. For example, a current of greater than 600 milliAmps may indicate that thrombus it partially or completely blocking the high pressure lumen 536, or even the aspiration lumen 538.

A vacuum line 556, connected to the vacuum source 522, may be connected to a negative pressure sensor 558. If the vacuum of the vacuum source 522 is low or if a leak is detected in the vacuum line 556, the control board 550 disables the pump 526 until the problem is corrected. The negative pressure sensor 558 may also be part of a safety circuit 560 that will not allow the pump 526 to run if a vacuum is not present. Thereby a comprehensive safety system 562, including the safety circuit 560, the pressure sensor 564 and/or the optical device 566, and the negative pressure sensor 558, requires both pump pressure and vacuum pressure for the system to run. If a problem exists (for example, if there is either a unacceptably low pump pressure or an absence of significant vacuum), the control board 550 will not allow the user to operate the aspiration system 510 until all problems are corrected. This will keep air from being injected into a patient, and will assure that the aspiration system 510 is not operated at incorrect parameters.

FIG. 49 is a diagrammatic view of the distal end portion 568 of the assisted catheter aspiration system 510, showing more details of the catheter 516. The catheter 516 is a single-operator exchange catheter and includes a short guidewire lumen 534 attached to the distal end of the device. The guidewire lumen 534 can be between about 1 and about 30 cm in length, or between about 5 and about 25 cm in length, or between about 5 and about 20 cm in length, or approximately 13.5 cm in length. An aspiration lumen 538 includes a distal opening 540 which allows a vacuum (for example, from vacuum source 522) to draw thrombotic material into the aspiration lumen 538. A high pressure lumen 536 includes a distal orifice 542 that is set proximally of distal opening 540 by a set amount. For example, distal orifice 42 can be set proximally of distal opening 540 by about 0.0508 cm (0.020 inches), or by 0.0508 cm±0.00762 cm (0.020 inches±0.003 inches) or by another desired amount. The orifice 542 is configured to spray across the aspiration lumen to macerate and/or dilute the thrombotic material for transport to vacuum source 522, for example, by lowering the effective viscosity of the thrombotic material. The axial placement of the fluid orifice 542 is such that the spray pattern interaction with the opposing lumen wall preferably produces a spray mist and not a swirl pattern that could force embolic material out from the distal opening 540. The system may be configured so that the irrigation fluid leaves the pump at a pressure of between about 3,447,378 pascal (500 psi) and about 10,342,135 pascal (1500 psi). In some embodiments, after a pressure head loss along the high pressure lumen 536, the irrigation fluid leaves orifice 542 at between about 4,136,854 pascal (600 psi) and about 8,273,708 pascal (1200 psi), or between about 4,481,592 pascal (650 psi) and about 5,860,543 pascal (850 psi). In some cases, it may be possible (and even desired) to use the assisted catheter aspiration system 510 without operating the pump 526, and thus use the catheter 516 while providing, for example, a hand saline injection via a syringe.

When normal blood flow is achieved after unblocking occlusions or blockages from atherosclerotic lesions and/or thrombosis, there is sometimes a risk of reperfusion injury. This may be particularly significant following thrombectomy of vessels feeding the brain for treatment of thromboembolic stroke, or following thrombectomy of coronary vessels feeding the myocardium. In the case of the revascularization of myocardium following a coronary intervention (e.g. thrombectomy). Reperfusion injury and microvascular dysfunction may be mechanisms that limit significant or full recovery of revascularized myocardium. The sudden reperfusion of a section of myocardium that had previously been underperfused may trigger a range of physiological processes that stun or damage the myocardium. Distal coronary emboli, such as small portions of thrombus, platelets and atheroma, may also play a part. Controlled preconditioning of the myocardium at risk has been proposed to limit the effect of reperfusion injury and microvascular dysfunction. The embodiments of the thrombectomy systems 100, 300 presented herein may be combined with additional features aimed at allowing flow control, in order to limit the potential dangers due to reperfusion following thrombectomy.

FIGS. 50A and 50B illustrate a thrombectomy system 600 comprising a catheter 606 and a guiding catheter 608. The catheter 606 may be an aspiration or thrombectomy catheter as previously described, and may or may not comprise a proximal sealing member. Alternatively, the catheter 606 may be used for partial or complete occlusion of the blood vessel distal of the guiding catheter 608. One purpose for this use is for flow control, as described above, wherein the distal tube 614 or another portion of the catheter 606 may be expanded to partially or completely occlude a blood vessel for a period of time. The catheter 606 may be a combination of an aspiration catheter and a catheter for flow control or occlusion. For example, the distal end of the distal tube 614 may provide some flow control in relation to the blood vessel wall, and the proximal end of the distal tube 614 may provide engagement with the guiding catheter. The guiding catheter 608 may, for example, have an outer diameter of 6 French, an inner lumen diameter of approximately 0.183 cm (0.072 inches), and have a total length of approximately 100 cm. The catheter 606 is configured to be placed through the inner lumen of the guiding catheter 608. The guiding catheter 608 may comprise a composite extruded and braided tubular structure, which has sufficient flexibility and pushability to reach a target area. The guiding catheter 608 may also have a pre-shaped tip. For example the tip shape may aid in cannulating coronary arteries. The catheter 606 comprises a distal tube 614 which is configured to be extendable out of the inner lumen of the guiding catheter 608, such that a distal end 616 of the distal tube 614 can be advanced a desired length into the blood vessel so that it can be placed adjacent the target area. The proximal end 618 of the distal tube 614 is configured to remain within the inner lumen of the guiding catheter 608, for example, at a region near the distal end of the guiding catheter 608. In some embodiments, the catheter 606 includes a radiopaque marker, which may comprise a band secured to the thrombectomy catheter, and made from radiodense material, such as platinum, gold, or other similar materials. In some embodiments, the distal tube 614 may be formed of polymeric materials containing radiopaque material, such as titanium dioxide ($TiO_2$).

The distal tube 614 comprises a tubular braided member whose diameter increases as the distal tube is made shorter (the distal end 616 and proximal end 618 are brought toward one another) and whose diameter decreases as the distal tube is made longer (the distal end 616 and proximal end 618 are moved away from one another). A tubular member of this type is sometimes referred to as a "Chinese finger trap." A stretchable material (such as silicone or urethane) may be used in some embodiments to fill in the spaces between the woven filaments in order to make a water-tight wall. As in certain other embodiments presented herein, a support member 626 is attached to the proximal end 618 of the distal tube 614 and is used to track the catheter 606 through the guiding catheter 608 and through the vasculature. A push/pull member 605 is attached to the distal end 616 of the distal tube 614 and, like the support member 626, extends proximally, and out of the proximal end of the guiding catheter 608 for access by a user. The support member 626 and the push/pull member 605 each have sufficient tensile strength and sufficient column strength such that each can be pushed and/or pulled accordingly, to cause the distal tube 614 to shorten or lengthen in length, thus changing its diameter. The support member 626 and the push/pull member 605 are each also lockable in relation to each other at their proximal ends, for example, just proximal to the proximal end of the guiding catheter, such that they are no longer able to longitudinally move independent of each other. This locks the distal tube 614 in its particular condition (diameter and length). The catheter 606 may be manipulated by the user so that support member 626 is pulled while the push/pull member 605 is pushed, thus elongating the distal tube 614 while decreasing its diameter (FIG. 50B). In this configuration, the distal tube 614 can be easily inserted through the guiding catheter 608. Once in a desired location within the vasculature, the catheter 606 may be manipulated by the user so that support member 626 is pushed while the push/pull member 605 is pulled, thus shortening the distal tube 614 while increasing its diameter (FIG. 50A). If this is done while the proximal end 618 of the distal tube 614 is within the distal tip of the inner lumen of the guiding catheter 608, an extended lumen may be made, which includes the lumen of the distal tube 614 and the inner lumen of the guiding catheter 608. If the proximal end 618 of the distal tube 614 has a ring of fill or coating material around its outer surface, for example, a stretchable material such as silicone or urethane, a seal may be created between the outer diameter of the distal tube 614 and the inner diameter of the guiding catheter 608. This is appropriate for an aspiration catheter mode. If flow control is desired, the distal tube 614 may be shortened and expanded in the same manner to that it engages the wall of the blood vessel at a desired location. In some embodiments, the push/pull member 605 and/or the support member 626 are constructed from hypo tubing, including but not limited to stainless steel hypo tubing or nitinol hypo tubing.

FIGS. 51A-51c show how the size of the distal tube 614 may be manipulated to reach different specific diameters. Longitudinally-displaced markings 677a, 677b, 677c, 679 or detents on the proximal ends 649, 651 of the support member 626 and/or the push/pull member 605, respectively, may indicate particular corresponding sizes (diameters or lengths) of the distal tube 614. For example, in FIG. 51A, an approximately 5 French diameter configuration of the distal tube 614 may be used for delivering it through the guiding catheter 608. In FIG. 51B, an approximately 6 French diameter configuration of the distal tube 614 may be used when it is tracked through the vasculature, for example, near a lesion site or target site. In FIG. 51C, an approximately 7 French diameter configuration of the distal tube 614 may be used when it is expanded towards or against the wall of a blood vessel. One or more loops 675 are configured to maintain the distance between the support member 626 and the push/pull member 605 in the radial direction (in relation to the distal tube 614). In some embodiments, the one or more loops 675 may be located near the proximal end 618 of the distal tube 614. FIGS. 51A-51C also show how in some embodiments, the push/pull member 605 may be constructed of flat wire. The support member 626 may also be constructed of flat wire.

Figure 52:
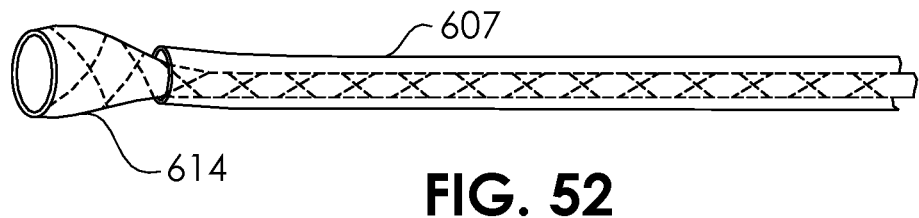
FIG. 52 is a perspective view of an aspiration catheter according to an embodiment of the present invention.
Figure 54:
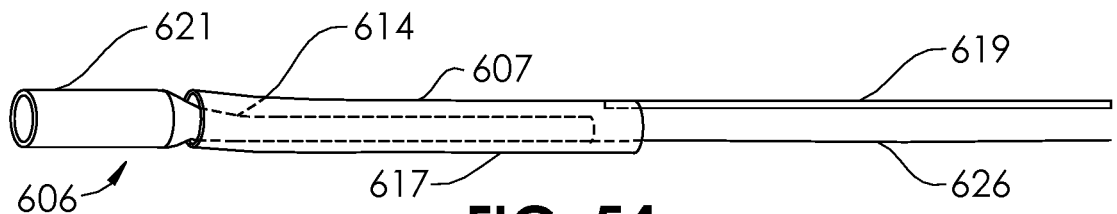
FIG. 54 is a perspective view of an aspiration catheter according to an embodiment of the present invention.

FIG. 52 shows an additional sleeve 607 which may be placed over the distal tube 614 to further constrain its diameter for delivery through the guiding catheter 608 and/or the vasculature. The sleeve 607 may extend proximally and out the proximal end of the guiding catheter 608 so that it can be pulled off in a proximal direction to allow the distal sleeve 614 to expand. The sleeve 607 may be used in addition to the push/pull member 605, or may be used in lieu of the push/pull member 605 and its utility in relation to the support member 626. In an alternative embodiment seen in FIG. 54, the sleeve 607 may comprise an elongate distal tube 617 which is coupled to a proximal wire or pusher member 619, this allowing a user to handle both the proximal wire 619 of the sleeve 607 and the support member 626 of the catheter 606 while removing the sleeve 607 from the patient. This would aid in holding the distal tube 614 at its desired location in the vasculature (and/or in the guiding catheter 608) while removing the sleeve 607. A portion 621 of the distal tube 614 which may remain distal of the sleeve 607 may comprise a non-expandable section.

Figure 53:
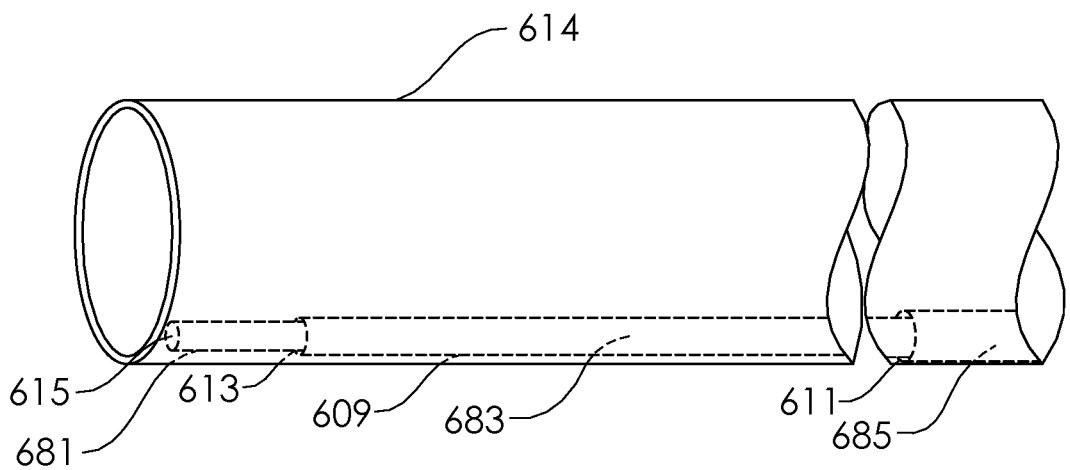
FIG. 53 is a perspective view of a thrombectomy catheter according to an embodiment of the present invention.
Figure 59:
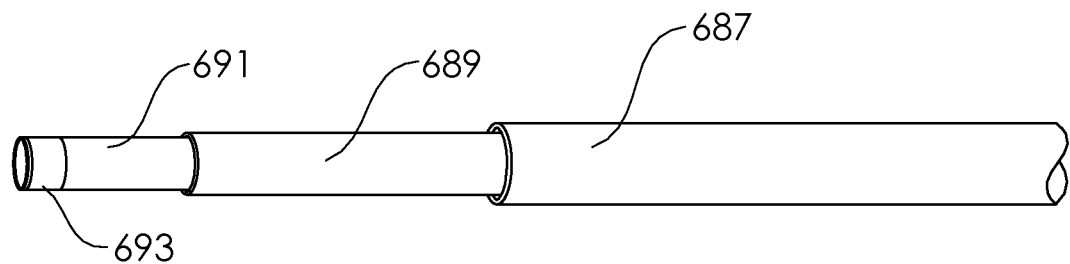
FIG. 59 is a perspective view of a component of an aspiration catheter according to an to an embodiment of the present invention.

FIG. 53 illustrates a thrombectomy catheter which may share certain elements of the embodiments of FIGS. 29-42. In this particular embodiment, a high pressure saline injection lumen 609 comprises two or more sections. As depicted, the injection lumen 609 includes a proximal portion 685, a middle portion 683 and a distal portion 681. The middle portion 683 is configured to telescope within the proximal portion 685 and the distal portion 681 is configured to telescope within the middle portion 683. Each portion may be constructed from precision tubing or hypo tubing, such as polyimide or nitinol, such that the difference in diameter between the opposing outer diameter and inner diameter of two neighboring tubes is very small, in order to create a capillary seal between the two. For example, in some embodiments the difference in diameters may be about 0.002 cm (0.0008 inches) or less, or in some embodiments about 0.001 cm (0.0004 inches) or less, or in some embodiments about 0.0005 cm (0.0002 inches) or less. This allows a section of injection lumen 609 that has a variable length, while being dynamically sealed, thus minimizing or eliminating any leakage at telescope points 611, 613, and allowing all or the vast majority of the injected saline to exit at exit port 615. In some embodiments, the capillary seal should be liquid tight, or water tight (saline tight), and in some embodiments need not be air tight (gas tight). A progressively smaller inner diameter from the proximal portion 685 to the distal portion 681 helps to maintain a high pressure jet at the exit port 615 (maximum pressure), without requiring too large of a pump head pressure. During delivery (tracking) of the catheter, a stylet may be placed within the injection lumen 609 in order to add stiffness, improve transition flexibility and protect the telescope points 611, 613 from damage. The stylet may be removed once the catheter is tracked to its desired location, and prior to the injection of saline and the aspiration of thrombus. In some embodiments, the proximal portion 685 may have an outer diameter of between about 0.0508 cm (0.020 inches) and 0.0732 cm (0.030 inches) or about 0.066 cm (0.026 inches). In some embodiments, the middle portion 683 may have an outer diameter of between about 0.0305 cm (0.012 inches) and 0.0559 cm (0.022 inches) or about 0.0406 cm (0.016 inches), In some embodiments, the distal portion 681 may have an outer diameter of between about 0.020 cm (0.008 inches) and 0.0406 cm (0.016 inches) or about 0.0305 cm (0.012 inches). In some embodiments, the proximal portion 685 may have an inner diameter of about 0.559 cm (0.022 inches), the middle portion 683 may have an inner diameter of about 0.0483 cm (0.019 inches), and the distal portion 681 may have an inner diameter of about 0.028 cm (0.011 inches). In the distal portion 681, an inner diameter of between about 0.0229 cm (0.009 inches) and about 0.0381 cm (0.015 inches) optimizes the delivery volume, while minimizing the outer diameter of the distal portion 681, thus maintaining the largest possible aspiration lumen cross-sectional area. In some embodiments, the distal tube 614 is a Chinese finger trap (braided tubular member) as previously described, and thus, the telescoping of the injection lumen 609 tubes allows the length change of the distal tube 614 freely. In this embodiment or any of the embodiments herein, the distal tube 614 may comprise a bumper of softer material at the distal end to add atraumatic characteristics. In alternative embodiments which do not require the telescoping of the injection lumen 609, the multiple layers of different diameter tubes may still be used in order to create a transition from larger diameter to smaller diameter and from stiffer to more flexible moving from the proximal end to the distal end. The tube sections may in this case be adhesively, epoxy or heat bonded together, or may be friction fit. FIG. 59 illustrates possible dimensions and assembly of an embodiment. The proximal portion 687 may comprise 0.066 cm×0.048 cm (0.026 inches×0.019 inches) stainless steel hypo tubing, for example, 304 series stainless steel. The middle portion 689 may comprise 0.066 cm×0.048 cm (0.016 inches×0.013 inches) nitinol tubing. The distal portion 691 may comprise polymeric tubing having a proximal outer diameter of about 0.028 cm (0.011 inches) tapering down distally to an outer diameter of about 0.028 cm (0.011 inches). A radiopaque marker band 693 may be carried on the distal portion having the 0.028 cm (0.011 inches) outer diameter. In some embodiments the high pressure injection lumen 609 may be secured to the inner wall of the distal tube 614, so that it will not severely flex or kink, and thus interfere with passage of a guidewire 28, 134 or cause a pinch or clog in the high pressure injection lumen 609. The high pressure injection lumen 609 may be secured with adhesive or other equivalent techniques.

Figure 55:
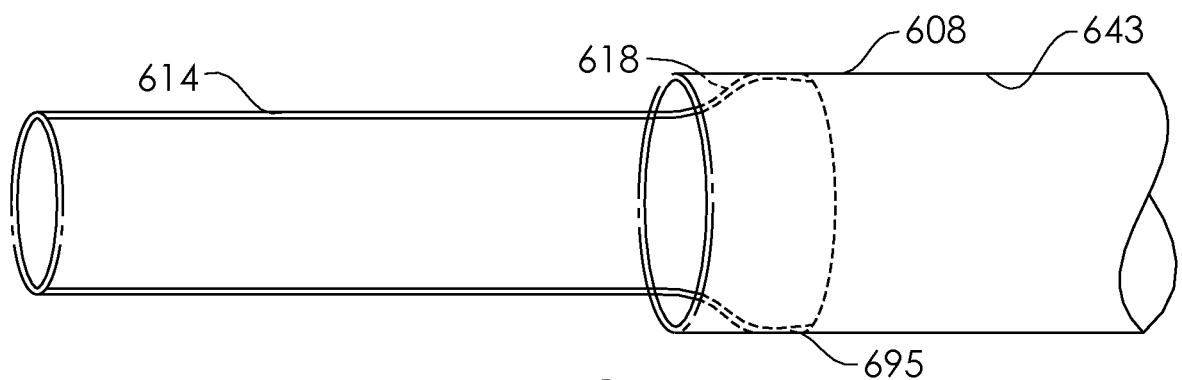
FIG. 55 is a perspective view of an aspiration system according to an embodiment of the present invention.

FIG. 55 illustrates the proximal end 618 of an embodiment of the distal tube 614 of the catheter 606 having an expanding structure 695 which seals against the inner diameter 643 of the guiding catheter 608. This may seal via the size of its formed diameter or it may be expandable by the user, for example, by using the combination of the support member 626 and the push/pull member 605 described herein.

FIGS. 56A-56C illustrate the flow control mode of the catheter 606 for approaching and/or sealing against the blood vessel wall. In some embodiments, the distal tube 614 may include a portion that has a diameter that is less than the blood vessel diameter. In these embodiments, the push/pull member 605 may be pulled and the support member 626 pushed in order to deliver the distal tube 614 against the vessel wall (while the diameter is increased and the length is shortened). In other embodiments, the distal tube 614 may include a portion that has a diameter that is about the same or larger than the blood vessel diameter. In these embodiments, the push/pull member 605 may be pushed and the support member 626 pulled in order to decrease the diameter (while increasing the length) to allow delivery down the guiding catheter 608 and through the vasculature. FIG. 56B illustrates the distal tube 614 extending from the guiding catheter 608, and expanded to seal against the wall of the blood vessel 102. FIG. 56C illustrates the distal tube 614 in a reduced diameter state configured for placement through the inner lumen 699 of the guiding catheter 608.

Figure 57:
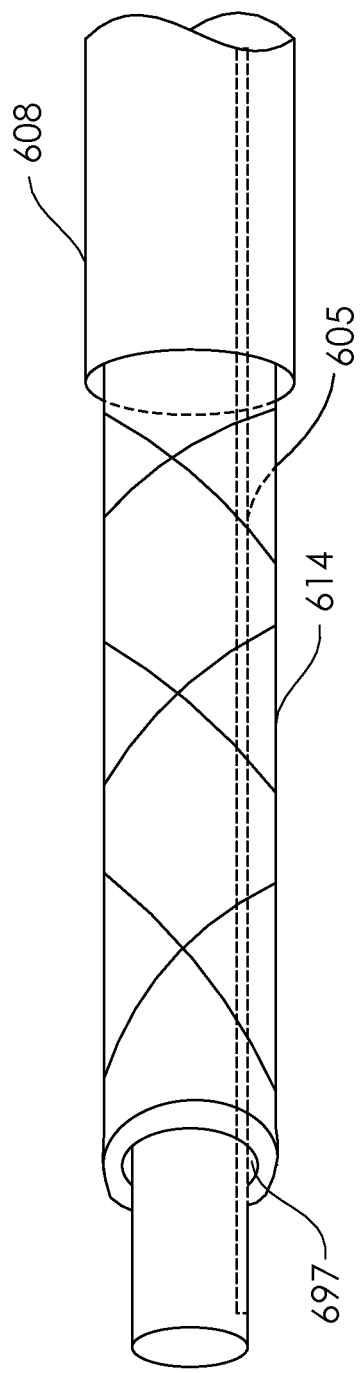
FIG. 57 is a perspective view of an aspiration system according to an embodiment of the present invention.

FIG. 57 illustrates an embodiment of the distal tube 614 with the Chinese finger trap in which pulling on the push/pull member 605 causes the distal tube 614 to invert at an inversion point 697. In some embodiments, the inversion may be done partially and may be used to cause an increase in the diameter of the distal tube 614 (for example, to perform flow control in the blood vessel). In some embodiments, the inversion may be done to remove the distal tube 614 from the vasculature and into the guiding catheter 608 or to remove the distal tube from the guiding catheter 608. By pushing on the push/pull member 605, the distal tube 614 may be delivered into a location in the blood vessel.

Figure 58A:
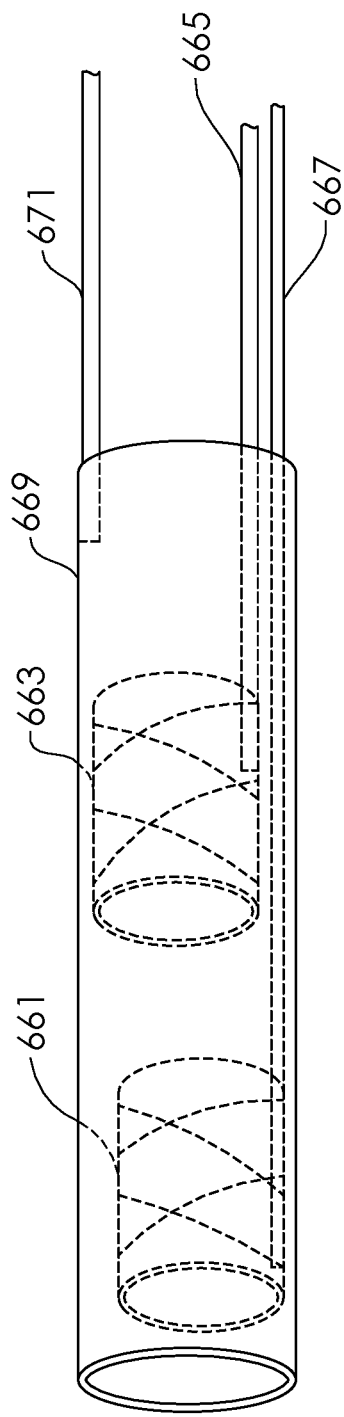
FIGS. 58A-58B are perspective views of an aspiration system according to an embodiment of the present invention.
Figure 58B:
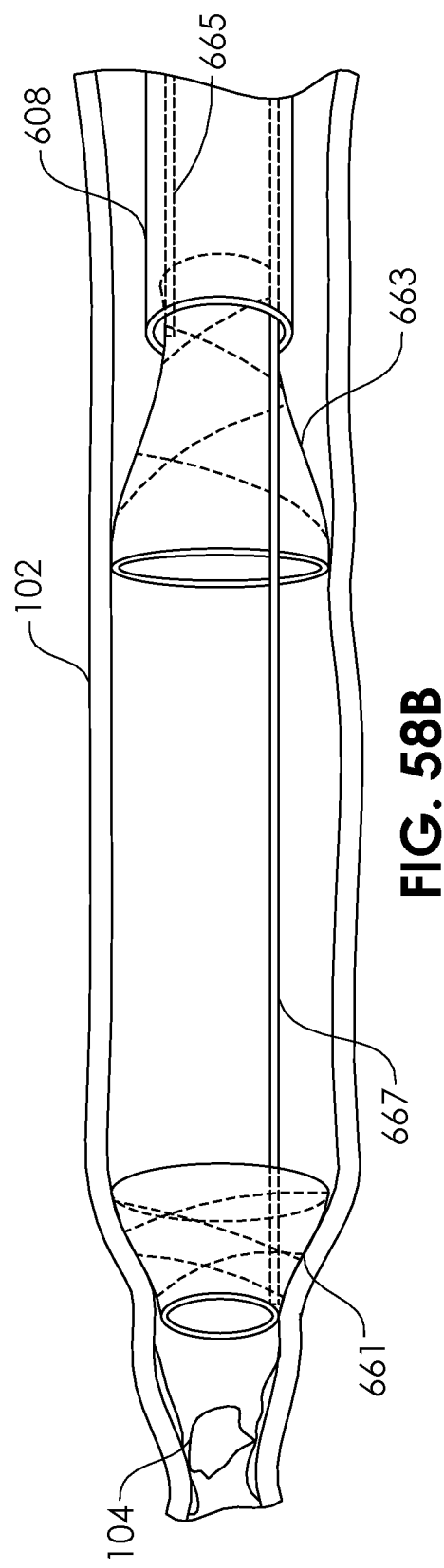

FIGS. 58A-58B illustrate how both flow control and the coupling to the guiding catheter 608 may be achieved using two different catheters, labeled in FIG. 58 as first catheter 661 and second catheter 663. The second catheter 663 (having support member 665) and the first catheter 661 (having support member 667) may each be delivered together within a larger delivery catheter 669 (having support member 671). After delivery through the guiding catheter 608 and to or near a target site (for example a clot/thrombus and/or an atherosclerotic lesion), the delivery catheter 669 is removed by pulling it proximally, and the first catheter 661 is positioned in the blood vessel 102 for flow control, and/or adjacent a thrombus 104, and the second catheter 663 is positioned in a coupling manner to the guiding catheter 608.

Figure 60:
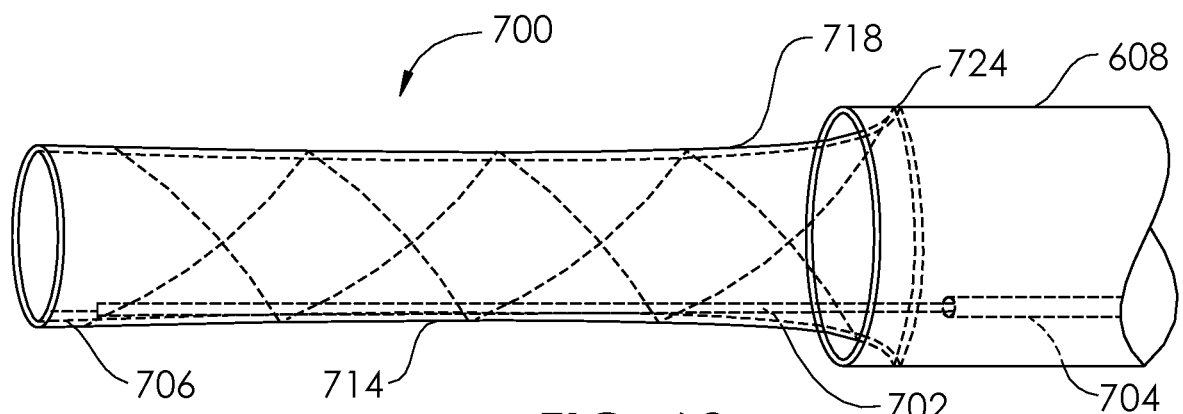
FIG. 60 is a perspective detail view of a portion of an aspiration catheter according to an embodiment of the present invention.

FIG. 60 an embodiment for a catheter 700 which also makes use of a distal tube using the Chinese finger trap braided tubular member 714. In this embodiment, a wire 702, for example a Nitinol wire, is telescopically located within a proximal 704. In some embodiments, a length of a more flexible material 706, such as polyimide is attached distal of the wire 702 for a transition of flexibility. The proximal end 718 of the distal tube 714 has a seal section 724 for engaging with the guiding catheter 608. The proximal end of the wire 702 extends proximally of the proximal end of the proximal tube 704. By pushing on the proximal tube 704 and pulling on the wire 702 at each of their respective proximal ends, a user may expand the distal tube 714 for flow control (e.g. blocking or slowing down blood flow that is coming from the right side of FIG. 60 to the left side of FIG. 60). A thrombectomy procedure may be performed through the extended lumen comprising the lumen of the distal tube and the inner lumen of the guiding catheter. Any combination of the embodiments disclosed herein may be used to create a combination flow control and thrombectomy embodiment. The thrombectomy portion may include aspiration only, or may combine aspiration and saline injection.

In one embodiment, an aspiration system includes an elongate tubular member for insertion into the vasculature of a patient, the elongate tubular member having a proximal end, a distal end, and a lumen extending from the proximal end to the distal end, the lumen having a first diameter adjacent the distal end, an aspiration catheter having a proximal end and a distal end and configured to be inserted through the lumen of the elongate tubular member, the aspiration catheter including a tubular aspiration member having a proximal end and a distal end and configured to at least partially extend out of the lumen of the elongate tubular member at the distal end of the elongate tubular member and into the vasculature of the patient, an elongate support member coupled to the tubular aspiration member and extending between the proximal end of the aspiration catheter and the proximal end of the tubular aspiration member, a plurality of annular seals linearly arrayed on an outer surface of the tubular aspiration member, each of the plurality of annular seals having an outer diameter which is greater than the first diameter of the lumen of the elongate tubular member, wherein the plurality of annular seals includes a first seal located adjacent the proximal end of the tubular aspiration member and a second seal located a distance d distally of the first seal on the tubular aspiration member, and wherein the distal end of the tubular aspiration member extends a length L from the distal end of the elongate tubular member when the first seal is engaged with the first diameter at the distal end of the elongate tubular member and the distal end of the tubular aspiration member extends a length L–d from the distal end of the elongate tubular member when the second seal is engaged with the first diameter at the distal end of the elongate tubular member, and a vacuum source configured for coupling to the proximal end of the elongate tubular member such that liquid having a viscosity of about 0.0025 pascal-seconds (2.5 cP) adjacent the distal end of the tubular aspiration member is aspirated into the distal end of the tubular aspiration member and through the elongate tubular member when either the first seal or the second seal is engaged with the first diameter at the distal end of the elongate tubular member.

In another embodiment, an aspiration system includes an elongate tubular member for insertion into the vasculature of a patient, the elongate tubular member having a proximal end, a distal end, and a lumen extending from the proximal end to the distal end, an aspiration catheter having a proximal end and a distal end and configured to be inserted through the lumen of the elongate tubular member, the aspiration catheter having a tubular aspiration member having a proximal end and a distal end and configured to at least partially extend out of the lumen of the elongate tubular member at the distal end of the elongate tubular member and into the vasculature of the patient, an elongate support member coupled to the tubular aspiration member and extending between the proximal end of the aspiration catheter and the proximal end of the tubular aspiration member, an annular sealing member having a first end, a second end and a wall, the first end coupled to the tubular aspiration member and having a first diameter and the second end having a second diameter greater than the first diameter, the second end located distally from the first end, a vacuum source configured for coupling to the proximal end of the elongate tubular member, and wherein the distal end of the annular sealing member creates a seal against the lumen of the elongate tubular member, substantially preventing liquid having a viscosity of about 0.0025 pascal-seconds (2.5 cP) from passing through space between the elongate tubular member and the tubular aspiration member in a distal to proximal direction when the vacuum source is applied to the proximal end of the elongate tubular member.

In another embodiment, an aspiration system includes an elongate tubular member for insertion into the vasculature of a patient, the elongate tubular member having a proximal end, a distal end, and a lumen extending from the proximal end to the distal end, the lumen having a first diameter adjacent the distal end, an aspiration catheter having a proximal end and a distal end and configured to be inserted through the lumen of the elongate tubular member, the aspiration catheter including a tubular aspiration member having a proximal end and a distal end and configured to at least partially extend out of the lumen of the elongate tubular member at the distal end of the elongate tubular member and into the vasculature of the patient, an elongate support member coupled to the tubular aspiration member and extending between the proximal end of the aspiration catheter and the proximal end of the tubular aspiration member, a hydrogel seal disposed on at least a cylindrical outer surface portion of the tubular aspiration member and having a non-hydrated diameter and an unconstrained hydrated diameter, the non-hydrated diameter less than the first diameter of the elongate tubular member and the unconstrained hydrated diameter greater than the first diameter of the elongate tubular member, such that the hydrogel seal is configured to seal against the first diameter of the elongate tubular member when it is hydrated, and a vacuum source configured for coupling to the proximal end of the elongate tubular member such that liquid having a viscosity of about 0.0025 pascal-seconds (2.5 cP) adjacent the distal end of the tubular aspiration member is aspirated into the distal end of the tubular aspiration member and through the elongate tubular member when the hydrogel seal is engaged with the first diameter at the distal end of the elongate tubular member.

In another embodiment, an aspiration system includes an elongate tubular member for insertion into the vasculature of a patient, the elongate tubular member having a proximal end, a distal end, and a lumen extending from the proximal end to the distal end, an aspiration catheter having a proximal end and a distal end and configured to be inserted through the lumen of the elongate tubular member, the aspiration catheter including a tubular aspiration member having a proximal end and a distal end and configured to at least partially extend out of the lumen of the elongate tubular member at the distal end of the elongate tubular member and into the vasculature of the patient, and a vacuum source configured for coupling to the proximal end of the elongate tubular member such that when the distal end of the tubular aspiration member is extended out of the distal end of the elongate tubular member at least 5 cm, liquid having a viscosity of about 0.0025 pascal-seconds (2.5 cP) adjacent the distal end of the tubular aspiration member is aspirated into the distal end of the tubular aspiration member and through the elongate tubular member at the same time that liquid having a viscosity of about 0.0025 pascal-seconds (2.5 cP) adjacent the distal end of the elongate tubular member is aspirated into space between the elongate tubular member and the tubular aspiration member and through the elongate tubular member. In some embodiments, the aspiration system is configured such that the proximal end of the tubular aspiration member is configured to extend proximally from the proximal end of the elongate tubular member when the distal end of the tubular aspiration member extends into the vasculature of the patient. In some embodiments, the aspiration system is configured such that the proximal end of the tubular aspiration member is configured reside within the elongate tubular member when the distal end of the tubular aspiration member extends into the vasculature of the patient. In some embodiments, the aspiration system further includes an elongate support member coupled to the tubular aspiration member and extending between the proximal end of the aspiration catheter and the proximal end of the tubular aspiration member.

In another embodiment, an aspiration system includes an elongate tubular member for insertion into the vasculature of a patient, the elongate tubular member having a proximal end, a distal end, and a lumen extending from the proximal end to the distal end, the lumen having a first diameter adjacent the distal end, an aspiration catheter having a proximal end and a distal end and configured to be inserted through the lumen of the elongate tubular member, the aspiration catheter including a tubular aspiration member having a proximal end, a distal end, an inner diameter and an outer diameter and configured to at least partially extend out of the lumen of the elongate tubular member at the distal end of the elongate tubular member and into the vasculature of the patient, an elongate support member coupled to the tubular aspiration member and extending between the proximal end of the aspiration catheter and the proximal end of the tubular aspiration member, the elongate support member having a distal end including a partial cylinder having an outer radius and an inner radius, one of the outer radius and inner radius configured to substantially match one of the outer diameter and inner diameter of the tubular aspiration member for joining thereto, a seal disposed on the tubular aspiration member configured to seal against the first diameter of the elongate tubular member, and a vacuum source configured for coupling to the proximal end of the elongate tubular member such that liquid having a viscosity of about 0.0025 pascal-seconds (2.5 cP) adjacent the distal end of the tubular aspiration member is aspirated into the distal end of the tubular aspiration member and through the elongate tubular member when the seal is engaged with the first diameter at the distal end of the elongate tubular member.

In another embodiment, a forced aspiration system includes an elongate tubular member for insertion into the vasculature of a patient, the elongate tubular member having a proximal end, a distal end, and a lumen extending from the proximal end to the distal end, the lumen having a first diameter adjacent the distal end, a forced aspiration catheter having a proximal end and a distal end and configured to be inserted through the lumen of the elongate tubular member, the forced aspiration catheter including, a tubular aspiration member having a proximal end, a distal end, an inner lumen, and an outer diameter and configured to at least partially extend out of the lumen of the elongate tubular member at the distal end of the elongate tubular member and into the vasculature of the patient, an elongate tubular support member coupled to the tubular aspiration member and having a lumen extending between the proximal end of the aspiration catheter and the proximal end of the tubular aspiration member, at least one orifice located adjacent the distal end of the tubular aspiration member, the at least one orifice configured to allow high pressure liquid injected through the lumen of the elongate tubular support member to be released into the inner lumen of the tubular aspiration member, and a seal disposed on the tubular aspiration member configured to seal against the first diameter of the elongate tubular member, a vacuum source configured for coupling to the proximal end of the elongate tubular member, and a pressurized liquid source configured for coupling to the proximal end of the lumen of the elongate tubular support member. In some embodiments, the forced aspiration system is configured such that the seal sealingly engages with the first diameter of the elongate tubular member when an internal pressure of the elongate tubular member immediately proximal to and adjacent the seal is increased upon coupling the elongate tubular support member to the pressurized liquid source.

In another embodiment, a method for aspirating material from a patient includes providing an elongate tubular member having a proximal end, a distal end, and a lumen extending from the proximal end to the distal end, the lumen having a first diameter adjacent the distal end, providing an aspiration catheter having a proximal end and a distal end and configured to be inserted through the lumen of the elongate tubular member, the aspiration catheter including a tubular aspiration member having a proximal end and a distal end and configured to at least partially extend out of the lumen of the elongate tubular member at the distal end of the elongate tubular member and into the vasculature of the patient, an elongate support member coupled to the tubular aspiration member and extending between the proximal end of the aspiration catheter and the proximal end of the tubular aspiration member, and an annular sealing member coupled to the tubular aspiration member and having a first diameter configured to seal against the first diameter of the elongate tubular member, placing the elongate tubular member into the vasculature of the patient, placing the aspiration catheter through the elongate tubular member so that the distal end of the tubular aspiration member extends from the distal end of the elongate tubular member and is adjacent a target area and the annular sealing member is aligned with the first diameter of the elongate tubular member, and coupling a vacuum source to the proximal end of the elongate tubular member so that material adjacent the target area is aspirated through the tubular aspiration member and the elongate tubular member.

In another embodiment, a method for treating patients includes providing a first elongate tubular member having a proximal end, a distal end, and a lumen extending from the proximal end to the distal end, the lumen having a first diameter adjacent the distal end, providing a first aspiration catheter having a proximal end and a distal end and configured to be inserted through the lumen of the first elongate tubular member, the first aspiration catheter including a first tubular aspiration member having a proximal end, a distal end, and a first length, the first tubular aspiration member configured to at least partially extend out of the lumen of the first elongate tubular member at the distal end of the first elongate tubular member and into the vasculature of a first patient, a first elongate support member coupled to the first tubular aspiration member and extending between the proximal end of the first aspiration catheter and the proximal end of the first tubular aspiration member, the first elongate support member having a first support member length, and a first annular sealing member coupled to the first tubular aspiration member and having a first diameter configured to seal against the first diameter of the elongate tubular member, placing the first elongate tubular member into the vasculature of the first patient, placing the first aspiration catheter through the first elongate tubular member so that the distal end of the first tubular aspiration member extends from the distal end of the first elongate tubular member and is adjacent a first target area and the first annular sealing member is aligned with the first diameter of the first elongate tubular member, coupling a first vacuum source to the proximal end of the first elongate tubular member so that material adjacent the first target area is aspirated through the first tubular aspiration member and the first elongate tubular member, providing a second elongate tubular member having a proximal end, a distal end, and a lumen extending from the proximal end to the distal end, the lumen having a second diameter adjacent the distal end, the second diameter substantially the same as the first diameter of the first elongate tubular member, providing a second aspiration catheter having a proximal end and a distal end and configured to be inserted through the lumen of the second elongate tubular member, the second aspiration catheter including a second tubular aspiration member having a proximal end, a distal end, and a second length, substantially the same as the first length of the first tubular aspiration member, the second tubular aspiration member configured to at least partially extend out of the lumen of the second elongate tubular member at the distal end of the second elongate tubular member and into the vasculature of a second patient, a second elongate support member coupled to the second tubular aspiration member and extending between the proximal end of the second aspiration catheter and the proximal end of the second tubular aspiration member, the second elongate support member having a second support member length, substantially the same as the first support member length, a second annular sealing member coupled to the second tubular aspiration member and having a second diameter configured to seal against the second diameter of the second elongate tubular member, placing the second elongate tubular member into the vasculature of the second patient, placing the second aspiration catheter through the second elongate tubular member so that the distal end of the second tubular aspiration member extends from the distal end of the second elongate tubular member and is adjacent a second target area and the second annular sealing member is aligned with the second diameter of the second elongate tubular member, and coupling a second vacuum source to the proximal end of the second elongate tubular member so that material adjacent the second target area is aspirated through the second tubular aspiration member and the second elongate tubular member.

Although several embodiments have been presented for breaking up or removing thrombus, general aspiration (with or without high pressure saline injection) of normal blood, or other liquids or deposits within the blood vessels, ducts or other tubular or non-tubular cavities of the body is contemplated as being within the scope of the embodiments of the present invention.

While embodiments have been shown and described, various modifications may be made without departing from the scope of the inventive concepts disclosed herein.

What is claimed is:

1. An aspiration catheter comprising:
   a proximal end;
   a distal end configured to be inserted through a lumen of a guiding catheter and into the vasculature of a patient;
   a tubular aspiration member having a proximal end, a distal end, and a lumen;
   an elongate support member coupled to the tubular aspiration member and extending between the proximal end of the aspiration catheter and the proximal end of the tubular aspiration member, the elongate support member from the proximal end of the aspiration catheter until the proximal end of the tubular aspiration member having a relatively small diameter in relation to the lumen of the tubular aspiration member; and
   an annular sealing surface coupled to the tubular aspiration member and configured to form an annular seal against the inner surface of the guiding catheter.

2. The aspiration catheter of claim 1, wherein the annular sealing surface is not on an inflatable balloon.

3. The aspiration catheter of claim 1, wherein the annular sealing surface is not expandable by a user.

4. The aspiration catheter of claim 1, wherein the annular sealing surface comprises a lip.

5. The aspiration catheter of claim 1, wherein the annular sealing surface comprises a flare.

6. The aspiration catheter of claim 1, wherein the annular sealing surface is on an elastomeric ring.

7. The aspiration catheter of claim 1, wherein the annular sealing surface comprises a hydrogel.

8. The aspiration catheter of claim 1, further comprising:
a hub coupled to the elongate support member at its proximal end.

9. The aspiration catheter of claim 1, further comprising:
a high pressure injection lumen having a proximal end and a distal end and extending along the elongate support member; and
at least one orifice at or near the distal end of the high pressure injection lumen and configured to allow high pressure liquid injected through the high pressure injection lumen to enter the lumen of the tubular aspiration member.

10. The aspiration catheter of claim 9, further comprising:
a hub coupled to the elongate support member, wherein the hub is configured to be decoupled from the high pressure injection lumen of the elongate support member.

11. An aspiration catheter comprising:
a proximal end;
a distal end configured to be inserted through a lumen of a guiding catheter and into the vasculature of a patient;
a tubular aspiration member having a proximal end, a distal end, and a lumen;
an elongate support member coupled to the tubular aspiration member and extending proximally from the proximal end of the tubular aspiration member, the elongate support member along the entirety of its length having a relatively small diameter in relation to the lumen of the tubular aspiration member, the elongate support member at the relatively small diameter configured to be sealed by a hemostatic valve of a y-connector; and
an annular sealing surface coupled to the tubular aspiration member and configured to form an annular seal against the inner surface of the guiding catheter.

12. The aspiration catheter of claim 11, wherein the annular sealing surface is not on an inflatable balloon.

13. The aspiration catheter of claim 11, wherein the annular sealing surface is not expandable by a user.

14. The aspiration catheter of claim 11, wherein the annular sealing surface comprises a lip.

15. The aspiration catheter of claim 11, wherein the annular sealing surface comprises a flare.

16. The aspiration catheter of claim 11, wherein the annular sealing surface is on an elastomeric ring.

17. The aspiration catheter of claim 11, wherein the annular sealing surface comprises a hydrogel.

18. The aspiration catheter of claim 11, further comprising:
a hub coupled to the elongate support member at its proximal end.

19. The aspiration catheter of claim 11, further comprising:
a high pressure injection lumen having a proximal end and a distal end and extending along the elongate support member; and
at least one orifice at or near the distal end of the high pressure injection lumen and configured to allow high pressure liquid injected through the high pressure injection lumen to enter the lumen of the tubular aspiration member.

20. The aspiration catheter of claim 19, further comprising:
a hub coupled to the elongate support member, wherein the hub is configured to be decoupled from the high pressure injection lumen of the elongate support member.

* * * * *